US012723270B2

(12) United States Patent
Barr et al.

(10) Patent No.: US 12,723,270 B2
(45) Date of Patent: Sep. 1, 2026

(54) GENETICALLY MODIFIED YEAST FOR THE PRODUCTION OF CANNABIGEROLIC ACID, CANNABICHROMENIC ACID AND RELATED CANNABINOIDS

(71) Applicant: BAYMEDICA, INC., Incline Village, NV (US)

(72) Inventors: Philip J. Barr, Incline Village, NV (US); Jianping Sun, Incline Village, NV (US); James T. Kealey, Incline Village, NV (US); Charles Marlowe, Incline Village, NV (US); James P. Craig, Incline Village, NV (US); Colin W. Johnson, Incline Village, NV (US)

(73) Assignee: BAYMEDICA, INC., Incline Village, NV (US)

( * ) Notice: Subject to any disclaimer, the term of this patent is extended or adjusted under 35 U.S.C. 154(b) by 717 days.

(21) Appl. No.: 17/794,210

(22) PCT Filed: Jan. 20, 2021

(86) PCT No.: PCT/US2021/014226
§ 371 (c)(1),
(2) Date: Jul. 20, 2022

(87) PCT Pub. No.: WO2021/150636
PCT Pub. Date: Jul. 29, 2021

(65) Prior Publication Data

US 2023/0063396 A1 Mar. 2, 2023

Related U.S. Application Data

(60) Provisional application No. 62/963,448, filed on Jan. 20, 2020.

(51) Int. Cl.

| | |
|---|---|
| ***C12P 7/42*** | (2006.01) |
| ***C12N 15/52*** | (2006.01) |
| ***C12N 15/81*** | (2006.01) |

(52) U.S. Cl.
CPC ................ *C12P 7/42* (2013.01); *C12N 15/52* (2013.01); *C12N 15/81* (2013.01); *C12Y 121/03007* (2015.07); *C12Y 121/03008* (2015.07); *C12Y 205/01102* (2015.07); *C12N 2800/102* (2013.01)

(58) Field of Classification Search
CPC ........ C12Y 203/01; C12N 9/10; C12N 15/81; C12N 9/1085
See application file for complete search history.

(56) References Cited

U.S. PATENT DOCUMENTS

| | | | | |
|---|---|---|---|---|
| 11,981,938 | B2 * | 5/2024 | Szamecz ............. | C12Y 203/01 |
| 2016/0053220 | A1 | 2/2016 | Peet et al. | |
| 2018/0016216 | A1 | 1/2018 | Leker et al. | |
| 2018/0334692 | A1 | 11/2018 | Barr et al. | |

FOREIGN PATENT DOCUMENTS

| | | | |
|---|---|---|---|
| WO | WO 2018/200888 | A1 | 11/2018 |
| WO | WO 2019/014490 | A1 | 1/2019 |
| WO | 2019/071000 | A1 | 4/2019 |
| WO | WO 2019/070876 | A2 | 4/2019 |
| WO | WO 2019/209885 | A2 | 10/2019 |

OTHER PUBLICATIONS

International Search Report and Written Opinion, Application No. PCT/US2021/014226, dated Jun. 8, 2021, 10 pages.

* cited by examiner

*Primary Examiner* — Tekchand Saidha
(74) *Attorney, Agent, or Firm* — Todd Lorenz

(57) ABSTRACT

The present invention relates generally to production methods, enzymes and recombinant yeast strains for the biosynthesis of clinically important cannabinoid compounds.

26 Claims, 3 Drawing Sheets

Specification includes a Sequence Listing.

1. Glucose
2. Glucose-6-phosphate
3. Fructose-6-phosphate
4. Fructose-1,6-bisphosphate
5. Glyceraldehyde-3-phosphate
6. Dihydroxyacetone phosphate
7. 1,3-bisphosphoglycerate
8. 3-phosphoglycerate
9. 2-phosphoglycerate
10. Phosphoenolpyruvate (PEP)
11. Pyruvate
12. Ethanol
13. Acetylaldehyde
14. Acetate
15. Acetyl-CoA
16. AcetoAcetyl-CoA
17. HMG-CoA
18. Mevalonate
19. Mevalonate-5-phosphate
20. Mevalonate-5-pyrophate
21. Isopentenyl pyrophosphate (IPP)
22. Dimethylallyl Pyrophosphate (DMA)
23. Geranyl diphophate (GPP)
24. Farnesyl pyrophosphate (FPP)

Biosynthetic pathway from sugar to CBCA

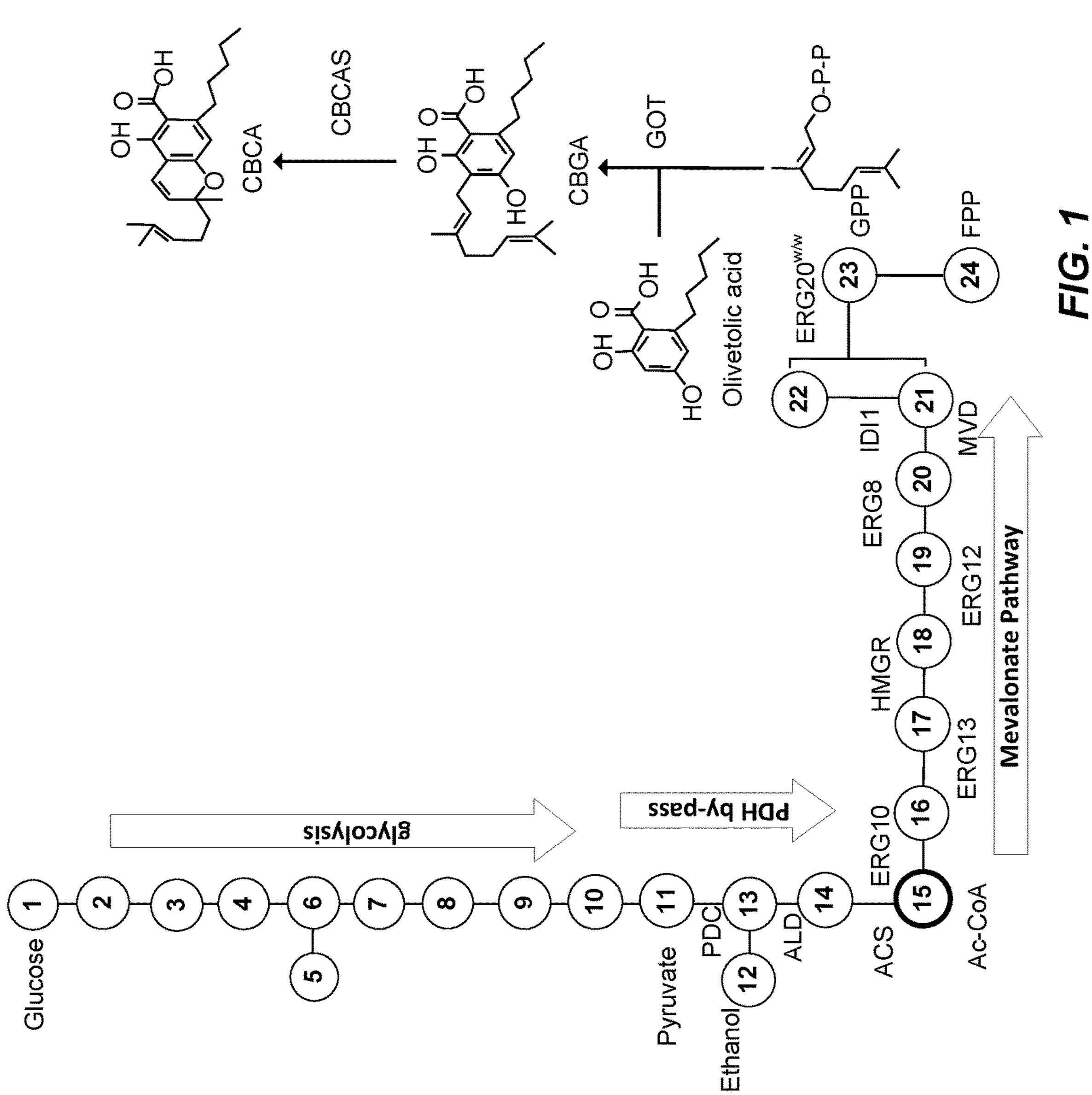

FIG. 1

Panel A, HPLC analysis of racemic, chemically-synthesized CBCA enantiomers and Panel B, 96% pure active enantiomer of CBC, following decarboxylation of CBCA biosynthesized in yeast.

Production of CBGA and minor cannabinoids (see text) in yeast cells.

SEQUENCE LISTING

<160> NUMBER OF SEQ ID NOS: 30

<210> SEQ ID NO 1
<211> LENGTH: 320
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Ser Asp Gln Ile Glu Gly Ser Pro His His Glu Ser Asp Asn Ser
1 5 10 15

Ile Ala Thr Lys Ile Leu Asn Phe Gly His Thr Cys Trp Lys Leu Gln
20 25 30

Arg Pro Tyr Val Val Lys Gly Met Ile Ser Ile Ala Cys Gly Leu Phe
35 40 45

Gly Arg Glu Leu Phe Asn Asn Arg His Leu Phe Ser Trp Gly Leu Met
50 55 60

Trp Lys Ala Phe Phe Ala Leu Val Pro Ile Leu Ser Phe Asn Phe Phe
65 70 75 80

Ala Ala Ile Met Asn Gln Ile Tyr Asp Val Asp Ile Asp Arg Ile Asn
85 90 95

Lys Pro Asp Leu Pro Leu Val Ser Gly Glu Met Ser Ile Glu Thr Ala
100 105 110

Trp Ile Leu Ser Ile Ile Val Ala Leu Thr Gly Leu Ile Val Thr Ile
115 120 125

Lys Leu Lys Ser Ala Pro Leu Phe Val Phe Ile Tyr Ile Phe Gly Ile
130 135 140

Phe Ala Gly Phe Ala Tyr Ser Val Pro Pro Ile Arg Trp Lys Gln Tyr
145 150 155 160

Pro Phe Thr Asn Phe Leu Ile Thr Ile Ser Ser His Val Gly Leu Ala
165 170 175

Phe Thr Ser Tyr Ser Ala Thr Thr Ser Ala Leu Gly Leu Pro Phe Val
180 185 190

Trp Arg Pro Ala Phe Ser Phe Ile Ile Ala Phe Met Thr Val Met Gly
195 200 205

Met Thr Ile Ala Phe Ala Lys Asp Ile Ser Asp Ile Glu Gly Asp Ala
210 215 220

Lys Tyr Gly Val Ser Thr Val Ala Thr Lys Leu Gly Ala Arg Asn Met
225 230 235 240

Thr Phe Val Val Ser Gly Val Leu Leu Leu Asn Tyr Leu Val Ser Ile
245 250 255

Ser Ile Gly Ile Ile Trp Pro Gln Val Phe Lys Ser Asn Ile Met Ile
260 265 270

Leu Ser His Ala Ile Leu Ala Phe Cys Leu Ile Phe Gln Thr Arg Glu
275 280 285

-continued

```
Leu Ala Leu Ala Asn Tyr Ala Ser Ala Pro Ser Arg Gln Phe Phe Glu
    290                 295                 300

Phe Ile Trp Leu Leu Tyr Tyr Ala Glu Tyr Phe Val Tyr Val Phe Ile
305                 310                 315                 320


<210> SEQ ID NO 2
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Pro Arg Ser Asp Gln Ile
145                 150                 155                 160

Glu Gly Ser Pro His His Glu Ser Asp Asn Ser Ile Ala Thr Lys Ile
                165                 170                 175

Leu Asn Phe Gly His Thr Cys Trp Lys Leu Gln Arg Pro Tyr Val Val
            180                 185                 190

Lys Gly Met Ile Ser Ile Ala Cys Gly Leu Phe Gly Arg Glu Leu Phe
        195                 200                 205

Asn Asn Arg His Leu Phe Ser Trp Gly Leu Met Trp Lys Ala Phe Phe
    210                 215                 220

Ala Leu Val Pro Ile Leu Ser Phe Asn Phe Phe Ala Ala Ile Met Asn
225                 230                 235                 240

Gln Ile Tyr Asp Val Asp Ile Asp Arg Ile Asn Lys Pro Asp Leu Pro
                245                 250                 255

Leu Val Ser Gly Glu Met Ser Ile Glu Thr Ala Trp Ile Leu Ser Ile
            260                 265                 270

Ile Val Ala Leu Thr Gly Leu Ile Val Thr Ile Lys Leu Lys Ser Ala
        275                 280                 285

Pro Leu Phe Val Phe Ile Tyr Ile Phe Gly Ile Phe Ala Gly Phe Ala
    290                 295                 300

Tyr Ser Val Pro Pro Ile Arg Trp Lys Gln Tyr Pro Phe Thr Asn Phe
305                 310                 315                 320

Leu Ile Thr Ile Ser Ser His Val Gly Leu Ala Phe Thr Ser Tyr Ser
```

```
                325                 330                 335

Ala Thr Thr Ser Ala Leu Gly Leu Pro Phe Val Trp Arg Pro Ala Phe
            340                 345                 350

Ser Phe Ile Ile Ala Phe Met Thr Val Met Gly Met Thr Ile Ala Phe
        355                 360                 365

Ala Lys Asp Ile Ser Asp Ile Glu Gly Asp Ala Lys Tyr Gly Val Ser
    370                 375                 380

Thr Val Ala Thr Lys Leu Gly Ala Arg Asn Met Thr Phe Val Val Ser
385                 390                 395                 400

Gly Val Leu Leu Leu Asn Tyr Leu Val Ser Ile Ser Ile Gly Ile Ile
                405                 410                 415

Trp Pro Gln Val Phe Lys Ser Asn Ile Met Ile Leu Ser His Ala Ile
            420                 425                 430

Leu Ala Phe Cys Leu Ile Phe Gln Thr Arg Glu Leu Ala Leu Ala Asn
        435                 440                 445

Tyr Ala Ser Ala Pro Ser Arg Gln Phe Phe Glu Phe Ile Trp Leu Leu
    450                 455                 460

Tyr Tyr Ala Glu Tyr Phe Val Tyr Val Phe Ile
465                 470                 475


<210> SEQ ID NO 3
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Phe Pro Ser Ile Phe Thr Thr Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Asn Pro Gln Glu Asn Phe Leu Lys Cys Phe
                85                  90                  95

Ser Glu Tyr Ile Pro Asn Asn Pro Ala Asn Pro Lys Phe Ile Tyr Thr
            100                 105                 110

Gln His Asp Gln Leu Tyr Met Ser Val Leu Asn Ser Thr Ile Gln Asn
        115                 120                 125

Leu Arg Phe Thr Ser Asp Thr Thr Pro Lys Pro Leu Val Ile Val Thr
    130                 135                 140

Pro Ser Asn Val Ser His Ile Gln Ala Ser Ile Leu Cys Ser Lys Lys
145                 150                 155                 160

Val Gly Leu Gln Ile Arg Thr Arg Ser Gly Gly His Asp Ala Glu Gly
                165                 170                 175

Leu Ser Tyr Ile Ser Gln Val Pro Phe Ala Ile Val Asp Leu Arg Asn
            180                 185                 190

Met His Thr Val Lys Val Asp Ile His Ser Gln Thr Ala Trp Val Glu
        195                 200                 205
```

-continued

```
Ala Gly Ala Thr Leu Gly Glu Val Tyr Tyr Trp Ile Asn Glu Met Asn
    210                 215                 220

Glu Asn Phe Ser Phe Pro Gly Gly Tyr Cys Pro Thr Val Gly Val Gly
225                 230                 235                 240

Gly His Phe Ser Gly Gly Gly Tyr Gly Ala Leu Met Arg Asn Tyr Gly
                245                 250                 255

Leu Ala Ala Asp Asn Ile Ile Asp Ala His Leu Val Asn Val Asp Gly
            260                 265                 270

Lys Val Leu Asp Arg Lys Ser Met Gly Glu Asp Leu Phe Trp Ala Ile
        275                 280                 285

Arg Gly Gly Gly Gly Glu Asn Phe Gly Ile Ile Ala Ala Trp Lys Ile
    290                 295                 300

Lys Leu Val Val Val Pro Ser Lys Ala Thr Ile Phe Ser Val Lys Lys
305                 310                 315                 320

Asn Met Glu Ile His Gly Leu Val Lys Leu Phe Asn Lys Trp Gln Asn
                325                 330                 335

Ile Ala Tyr Lys Tyr Asp Lys Asp Leu Met Leu Thr Thr His Phe Arg
            340                 345                 350

Thr Arg Asn Ile Thr Asp Asn His Gly Lys Asn Lys Thr Thr Val His
        355                 360                 365

Gly Tyr Phe Ser Ser Ile Phe Leu Gly Gly Val Asp Ser Leu Val Asp
    370                 375                 380

Leu Met Asn Lys Ser Phe Pro Glu Leu Gly Ile Lys Lys Thr Asp Cys
385                 390                 395                 400

Lys Glu Leu Ser Trp Ile Asp Thr Thr Ile Phe Tyr Ser Gly Val Val
                405                 410                 415

Asn Tyr Asn Thr Ala Asn Phe Lys Lys Glu Ile Leu Leu Asp Arg Ser
            420                 425                 430

Ala Gly Lys Lys Thr Ala Phe Ser Ile Lys Leu Asp Tyr Val Lys Lys
        435                 440                 445

Leu Ile Pro Glu Thr Ala Met Val Lys Ile Leu Glu Lys Leu Tyr Glu
    450                 455                 460

Glu Glu Val Gly Val Gly Met Tyr Val Leu Tyr Pro Tyr Gly Gly Ile
465                 470                 475                 480

Met Asp Glu Ile Ser Glu Ser Ala Ile Pro Phe Pro His Arg Ala Gly
                485                 490                 495

Ile Met Tyr Glu Leu Trp Tyr Thr Ala Thr Trp Glu Lys Gln Glu Asp
            500                 505                 510

Asn Glu Lys His Ile Asn Trp Val Arg Ser Val Tyr Asn Phe Thr Thr
        515                 520                 525

Pro Tyr Val Ser Gln Asn Pro Arg Leu Ala Tyr Leu Asn Tyr Arg Asp
    530                 535                 540

Leu Asp Leu Gly Lys Thr Asn Pro Glu Ser Pro Asn Asn Tyr Thr Gln
545                 550                 555                 560

Ala Arg Ile Trp Gly Glu Lys Tyr Phe Gly Lys Asn Phe Asn Arg Leu
                565                 570                 575

Val Lys Val Lys Thr Lys Ala Asp Pro Asn Asn Phe Phe Arg Asn Glu
            580                 585                 590

Gln Ser Ile Pro Pro Leu Pro Pro Arg His His
        595                 600
```

<210> SEQ ID NO 4
<211> LENGTH: 606
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 4

```
Met Arg Phe Pro Ser Ile Phe Thr Thr Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Asn Pro Gln Glu Asn Phe Leu Lys Cys Phe
                85                  90                  95

Ser Glu Tyr Ile Pro Asn Asn Pro Ala Asn Pro Lys Phe Ile Tyr Thr
            100                 105                 110

Gln His Asp Gln Leu Tyr Met Ser Val Leu Asn Ser Thr Ile Gln Asn
        115                 120                 125

Leu Arg Phe Thr Ser Asp Thr Thr Pro Lys Pro Leu Val Ile Val Thr
    130                 135                 140

Pro Ser Asn Val Ser His Ile Gln Ala Ser Ile Leu Cys Ser Lys Lys
145                 150                 155                 160

Val Gly Leu Gln Ile Arg Thr Arg Ser Gly Gly His Asp Ala Glu Gly
                165                 170                 175

Leu Ser Tyr Ile Ser Gln Val Pro Phe Ala Ile Val Asp Leu Arg Asn
            180                 185                 190

Met His Thr Val Lys Val Asp Ile His Ser Gln Thr Ala Trp Val Glu
        195                 200                 205

Ala Gly Ala Thr Leu Gly Glu Val Tyr Tyr Trp Ile Asn Glu Met Asn
    210                 215                 220

Glu Asn Phe Ser Phe Pro Gly Gly Tyr Cys Pro Thr Val Gly Val Gly
225                 230                 235                 240

Gly His Phe Ser Gly Gly Gly Tyr Gly Ala Leu Met Arg Asn Tyr Gly
                245                 250                 255

Leu Ala Ala Asp Asn Ile Ile Asp Ala His Leu Val Asn Val Asp Gly
            260                 265                 270

Lys Val Leu Asp Arg Lys Ser Met Gly Glu Asp Leu Phe Trp Ala Ile
        275                 280                 285

Arg Gly Gly Gly Gly Glu Asn Phe Gly Ile Ile Ala Ala Trp Lys Ile
    290                 295                 300

Lys Leu Val Val Val Pro Ser Lys Ala Thr Ile Phe Ser Val Lys Lys
305                 310                 315                 320

Asn Met Glu Ile His Gly Leu Val Lys Leu Phe Asn Lys Trp Gln Asn
                325                 330                 335

Ile Ala Tyr Lys Tyr Asp Lys Asp Leu Met Leu Thr Thr His Phe Arg
            340                 345                 350

Thr Arg Asn Ile Thr Asp Asn His Gly Lys Asn Lys Thr Thr Val His
        355                 360                 365

Gly Tyr Phe Ser Ser Ile Phe Leu Gly Gly Val Asp Ser Leu Val Asp
    370                 375                 380
```

```
Leu Met Asn Lys Ser Phe Pro Glu Leu Gly Ile Lys Lys Thr Asp Cys
385                 390                 395                 400

Lys Glu Leu Ser Trp Ile Asp Thr Thr Ile Phe Tyr Ser Gly Val Val
                405                 410                 415

Asn Tyr Asn Thr Ala Asn Phe Lys Lys Glu Ile Leu Leu Asp Arg Ser
            420                 425                 430

Ala Gly Lys Lys Thr Ala Phe Ser Ile Lys Leu Asp Tyr Val Lys Lys
        435                 440                 445

Leu Ile Pro Glu Thr Ala Met Val Lys Ile Leu Glu Lys Leu Tyr Glu
    450                 455                 460

Glu Glu Val Gly Val Gly Met Tyr Val Leu Tyr Pro Tyr Gly Gly Ile
465                 470                 475                 480

Met Asp Glu Ile Ser Glu Ser Ala Ile Pro Phe Pro His Arg Ala Gly
                485                 490                 495

Ile Met Tyr Glu Leu Trp Tyr Thr Ala Thr Trp Glu Lys Gln Glu Asp
            500                 505                 510

Asn Glu Lys His Ile Asn Trp Val Arg Ser Val Tyr Asn Phe Thr Thr
        515                 520                 525

Pro Tyr Val Ser Gln Asn Pro Arg Leu Ala Tyr Leu Asn Tyr Arg Asp
    530                 535                 540

Leu Asp Leu Gly Lys Thr Asn Pro Glu Ser Pro Asn Asn Tyr Thr Gln
545                 550                 555                 560

Ala Arg Ile Trp Gly Glu Lys Tyr Phe Gly Lys Asn Phe Asn Arg Leu
                565                 570                 575

Val Lys Val Lys Thr Lys Ala Asp Asn Asn Phe Phe Arg Asn Glu Gln
            580                 585                 590

Ser Ile Pro Pro Leu Pro Pro Arg His His His Asp Glu Leu
        595                 600                 605


<210> SEQ ID NO 5
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Phe Ser Ala Gly Ala Val Leu Ser Trp Ser Ser Leu Leu Leu
1               5                   10                  15

Ala Ser Ser Val Phe Ala Gln Gln Ala Asn Pro Gln Glu Asn Phe Leu
            20                  25                  30

Lys Cys Phe Ser Glu Tyr Ile Pro Asn Asn Pro Ala Asn Pro Lys Phe
        35                  40                  45

Ile Tyr Thr Gln His Asp Gln Leu Tyr Met Ser Val Leu Asn Ser Thr
    50                  55                  60

Ile Gln Asn Leu Arg Phe Thr Ser Asp Thr Thr Pro Lys Pro Leu Val
65                  70                  75                  80

Ile Val Thr Pro Ser Asn Val Ser His Ile Gln Ala Ser Ile Leu Cys
                85                  90                  95

Ser Lys Lys Val Gly Leu Gln Ile Arg Thr Arg Ser Gly Gly His Asp
            100                 105                 110

Ala Glu Gly Leu Ser Tyr Ile Ser Gln Val Pro Phe Ala Ile Val Asp
        115                 120                 125

Leu Arg Asn Met His Thr Val Lys Val Asp Ile His Ser Gln Thr Ala
    130                 135                 140
```

-continued

```
Trp Val Glu Ala Gly Ala Thr Leu Gly Glu Val Tyr Tyr Trp Ile Asn
145                 150                 155                 160

Glu Met Asn Glu Asn Phe Ser Phe Pro Gly Gly Tyr Cys Pro Thr Val
                165                 170                 175

Gly Val Gly Gly His Phe Ser Gly Gly Gly Tyr Gly Ala Leu Met Arg
            180                 185                 190

Asn Tyr Gly Leu Ala Ala Asp Asn Ile Ile Asp Ala His Leu Val Asn
        195                 200                 205

Val Asp Gly Lys Val Leu Asp Arg Lys Ser Met Gly Glu Asp Leu Phe
    210                 215                 220

Trp Ala Ile Arg Gly Gly Gly Gly Glu Asn Phe Gly Ile Ile Ala Ala
225                 230                 235                 240

Trp Lys Ile Lys Leu Val Val Val Pro Ser Lys Ala Thr Ile Phe Ser
                245                 250                 255

Val Lys Lys Asn Met Glu Ile His Gly Leu Val Lys Leu Phe Asn Lys
            260                 265                 270

Trp Gln Asn Ile Ala Tyr Lys Tyr Asp Lys Asp Leu Met Leu Thr Thr
        275                 280                 285

His Phe Arg Thr Arg Asn Ile Thr Asp Asn His Gly Lys Asn Lys Thr
    290                 295                 300

Thr Val His Gly Tyr Phe Ser Ser Ile Phe Leu Gly Gly Val Asp Ser
305                 310                 315                 320

Leu Val Asp Leu Met Asn Lys Ser Phe Pro Glu Leu Gly Ile Lys Lys
                325                 330                 335

Thr Asp Cys Lys Glu Leu Ser Trp Ile Asp Thr Thr Ile Phe Tyr Ser
            340                 345                 350

Gly Val Val Asn Tyr Asn Thr Ala Asn Phe Lys Lys Glu Ile Leu Leu
        355                 360                 365

Asp Arg Ser Ala Gly Lys Lys Thr Ala Phe Ser Ile Lys Leu Asp Tyr
    370                 375                 380

Val Lys Lys Leu Ile Pro Glu Thr Ala Met Val Lys Ile Leu Glu Lys
385                 390                 395                 400

Leu Tyr Glu Glu Glu Val Gly Val Gly Met Tyr Val Leu Tyr Pro Tyr
                405                 410                 415

Gly Gly Ile Met Asp Glu Ile Ser Glu Ser Ala Ile Pro Phe Pro His
            420                 425                 430

Arg Ala Gly Ile Met Tyr Glu Leu Trp Tyr Thr Ala Thr Trp Glu Lys
        435                 440                 445

Gln Glu Asp Asn Glu Lys His Ile Asn Trp Val Arg Ser Val Tyr Asn
    450                 455                 460

Phe Thr Thr Pro Tyr Val Ser Gln Asn Pro Arg Leu Ala Tyr Leu Asn
465                 470                 475                 480

Tyr Arg Asp Leu Asp Leu Gly Lys Thr Asn Pro Glu Ser Pro Asn Asn
                485                 490                 495

Tyr Thr Gln Ala Arg Ile Trp Gly Glu Lys Tyr Phe Gly Lys Asn Phe
            500                 505                 510

Asn Arg Leu Val Lys Val Lys Thr Lys Ala Asp Pro Asn Asn Phe Phe
        515                 520                 525

Arg Asn Glu Gln Ser Ile Pro Pro Leu Pro Pro Arg His His
    530                 535                 540
```

<210> SEQ ID NO 6
<211> LENGTH: 549

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Gln Ser Arg Gly Ile Leu Gly Gly Val Arg Gln Leu Ile Leu
1               5                   10                  15

Val Ile Leu Val Gly Ala Tyr Leu Ser Arg Leu Ser Ala Val Asp Ala
            20                  25                  30

Asn Pro Gln Glu Asn Phe Leu Lys Cys Phe Ser Glu Tyr Ile Pro Asn
        35                  40                  45

Asn Pro Ala Asn Pro Lys Phe Ile Tyr Thr Gln His Asp Gln Leu Tyr
    50                  55                  60

Met Ser Val Leu Asn Ser Thr Ile Gln Asn Leu Arg Phe Thr Ser Asp
65                  70                  75                  80

Thr Thr Pro Lys Pro Leu Val Ile Val Thr Pro Ser Asn Val Ser His
                85                  90                  95

Ile Gln Ala Ser Ile Leu Cys Ser Lys Lys Val Gly Leu Gln Ile Arg
            100                 105                 110

Thr Arg Ser Gly Gly His Asp Ala Glu Gly Leu Ser Tyr Ile Ser Gln
        115                 120                 125

Val Pro Phe Ala Ile Val Asp Leu Arg Asn Met His Thr Val Lys Val
    130                 135                 140

Asp Ile His Ser Gln Thr Ala Trp Val Glu Ala Gly Ala Thr Leu Gly
145                 150                 155                 160

Glu Val Tyr Tyr Trp Ile Asn Glu Met Asn Glu Asn Phe Ser Phe Pro
                165                 170                 175

Gly Gly Tyr Cys Pro Thr Val Gly Val Gly Gly His Phe Ser Gly Gly
            180                 185                 190

Gly Tyr Gly Ala Leu Met Arg Asn Tyr Gly Leu Ala Ala Asp Asn Ile
        195                 200                 205

Ile Asp Ala His Leu Val Asn Val Asp Gly Lys Val Leu Asp Arg Lys
    210                 215                 220

Ser Met Gly Glu Asp Leu Phe Trp Ala Ile Arg Gly Gly Gly Gly Glu
225                 230                 235                 240

Asn Phe Gly Ile Ile Ala Ala Trp Lys Ile Lys Leu Val Val Val Pro
                245                 250                 255

Ser Lys Ala Thr Ile Phe Ser Val Lys Lys Asn Met Glu Ile His Gly
            260                 265                 270

Leu Val Lys Leu Phe Asn Lys Trp Gln Asn Ile Ala Tyr Lys Tyr Asp
        275                 280                 285

Lys Asp Leu Met Leu Thr Thr His Phe Arg Thr Arg Asn Ile Thr Asp
    290                 295                 300

Asn His Gly Lys Asn Lys Thr Thr Val His Gly Tyr Phe Ser Ser Ile
305                 310                 315                 320

Phe Leu Gly Gly Val Asp Ser Leu Val Asp Leu Met Asn Lys Ser Phe
                325                 330                 335

Pro Glu Leu Gly Ile Lys Lys Thr Asp Cys Lys Glu Leu Ser Trp Ile
            340                 345                 350

Asp Thr Thr Ile Phe Tyr Ser Gly Val Val Asn Tyr Asn Thr Ala Asn
        355                 360                 365

Phe Lys Lys Glu Ile Leu Leu Asp Arg Ser Ala Gly Lys Lys Thr Ala
    370                 375                 380
```

```
Phe Ser Ile Lys Leu Asp Tyr Val Lys Lys Leu Ile Pro Glu Thr Ala
385                 390                 395                 400

Met Val Lys Ile Leu Glu Lys Leu Tyr Glu Glu Glu Val Gly Val Gly
                405                 410                 415

Met Tyr Val Leu Tyr Pro Tyr Gly Gly Ile Met Asp Glu Ile Ser Glu
            420                 425                 430

Ser Ala Ile Pro Phe Pro His Arg Ala Gly Ile Met Tyr Glu Leu Trp
        435                 440                 445

Tyr Thr Ala Thr Trp Glu Lys Gln Glu Asp Asn Glu Lys His Ile Asn
    450                 455                 460

Trp Val Arg Ser Val Tyr Asn Phe Thr Thr Pro Tyr Val Ser Gln Asn
465                 470                 475                 480

Pro Arg Leu Ala Tyr Leu Asn Tyr Arg Asp Leu Asp Leu Gly Lys Thr
                485                 490                 495

Asn Pro Glu Ser Pro Asn Asn Tyr Thr Gln Ala Arg Ile Trp Gly Glu
            500                 505                 510

Lys Tyr Phe Gly Lys Asn Phe Asn Arg Leu Val Lys Val Lys Thr Lys
        515                 520                 525

Ala Asp Pro Asn Asn Phe Phe Arg Asn Glu Gln Ser Ile Pro Pro Leu
    530                 535                 540

Pro Pro Arg His His
545


<210> SEQ ID NO 7
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Phe Pro Ser Ile Phe Thr Thr Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Pro Ser Asn Val Ser His Ile Gln Ala Ser Ile
                85                  90                  95

Leu Cys Ser Lys Lys Val Gly Leu Gln Ile Arg Thr Arg Ser Gly Gly
            100                 105                 110

His Asp Ala Glu Gly Leu Ser Tyr Ile Ser Gln Val Pro Phe Ala Ile
        115                 120                 125

Val Asp Leu Arg Asn Met His Thr Val Lys Val Asp Ile His Ser Gln
    130                 135                 140

Thr Ala Trp Val Glu Ala Gly Ala Thr Leu Gly Glu Val Tyr Tyr Trp
145                 150                 155                 160

Ile Asn Glu Met Asn Glu Asn Phe Ser Phe Pro Gly Gly Tyr Cys Pro
                165                 170                 175

Thr Val Gly Val Gly Gly His Phe Ser Gly Gly Gly Tyr Gly Ala Leu
```

-continued

```
            180                 185                 190

Met Arg Asn Tyr Gly Leu Ala Ala Asp Asn Ile Ile Asp Ala His Leu
        195                 200                 205

Val Asn Val Asp Gly Lys Val Leu Asp Arg Lys Ser Met Gly Glu Asp
    210                 215                 220

Leu Phe Trp Ala Ile Arg Gly Gly Gly Gly Glu Asn Phe Gly Ile Ile
225                 230                 235                 240

Ala Ala Trp Lys Ile Lys Leu Val Val Val Pro Ser Lys Ala Thr Ile
                245                 250                 255

Phe Ser Val Lys Lys Asn Met Glu Ile His Gly Leu Val Lys Leu Phe
            260                 265                 270

Asn Lys Trp Gln Asn Ile Ala Tyr Lys Tyr Asp Lys Asp Leu Met Leu
        275                 280                 285

Thr Thr His Phe Arg Thr Arg Asn Ile Thr Asp Asn His Gly Lys Asn
    290                 295                 300

Lys Thr Thr Val His Gly Tyr Phe Ser Ser Ile Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Lys Glu Leu Ser Trp Ile Asp Thr Thr Ile Phe
            340                 345                 350

Tyr Ser Gly Val Val Asn Tyr Asn Thr Ala Asn Phe Lys Lys Glu Ile
        355                 360                 365

Leu Leu Asp Arg Ser Ala Gly Lys Lys Thr Ala Phe Ser Ile Lys Leu
    370                 375                 380

Asp Tyr Val Lys Lys Leu Ile Pro Glu Thr Ala Met Val Lys Ile Leu
385                 390                 395                 400

Glu Lys Leu Tyr Glu Glu Glu Val Gly Val Gly Met Tyr Val Leu Tyr
                405                 410                 415

Pro Tyr Gly Gly Ile Met Asp Glu Ile Ser Glu Ser Ala Ile Pro Phe
            420                 425                 430

Pro His Arg Ala Gly Ile Met Tyr Glu Leu Trp Tyr Thr Ala Thr Trp
        435                 440                 445

Glu Lys Gln Glu Asp Asn Glu Lys His Ile Asn Trp Val Arg Ser Val
    450                 455                 460

Tyr Asn Phe Thr Thr Pro Tyr Val Ser Gln Asn Pro Arg Leu Ala Tyr
465                 470                 475                 480

Leu Asn Tyr Arg Asp Leu Asp Leu Gly Lys Thr Asn Pro Glu Ser Pro
                485                 490                 495

Asn Asn Tyr Thr Gln Ala Arg Ile Trp Gly Glu Lys Tyr Phe Gly Lys
            500                 505                 510

Asn Phe Asn Arg Leu Val Lys Val Lys Thr Lys Ala Asp Pro Asn Asn
        515                 520                 525

Phe Phe Arg Asn Glu Gln Ser Ile Pro Pro Leu Pro Pro Arg His His
    530                 535                 540
```

<210> SEQ ID NO 8
<211> LENGTH: 460
<212> TYPE: PRT
<213> ORGANISM: Unknown
<220> FEATURE:
<223> OTHER INFORMATION: Description of Unknown:
      CBCAS sequence

<400> SEQUENCE: 8

-continued

```
Met Pro Ser Asn Val Ser His Ile Gln Ala Ser Ile Leu Cys Ser Lys
1               5                   10                  15

Lys Val Gly Leu Gln Ile Arg Thr Arg Ser Gly Gly His Asp Ala Glu
            20                  25                  30

Gly Leu Ser Tyr Ile Ser Gln Val Pro Phe Ala Ile Val Asp Leu Arg
        35                  40                  45

Asn Met His Thr Val Lys Val Asp Ile His Ser Gln Thr Ala Trp Val
    50                  55                  60

Glu Ala Gly Ala Thr Leu Gly Glu Val Tyr Tyr Trp Ile Asn Glu Met
65                  70                  75                  80

Asn Glu Asn Phe Ser Phe Pro Gly Gly Tyr Cys Pro Thr Val Gly Val
                85                  90                  95

Gly Gly His Phe Ser Gly Gly Gly Tyr Gly Ala Leu Met Arg Asn Tyr
            100                 105                 110

Gly Leu Ala Ala Asp Asn Ile Ile Asp Ala His Leu Val Asn Val Asp
        115                 120                 125

Gly Lys Val Leu Asp Arg Lys Ser Met Gly Glu Asp Leu Phe Trp Ala
    130                 135                 140

Ile Arg Gly Gly Gly Gly Glu Asn Phe Gly Ile Ile Ala Ala Trp Lys
145                 150                 155                 160

Ile Lys Leu Val Val Val Pro Ser Lys Ala Thr Ile Phe Ser Val Lys
                165                 170                 175

Lys Asn Met Glu Ile His Gly Leu Val Lys Leu Phe Asn Lys Trp Gln
            180                 185                 190

Asn Ile Ala Tyr Lys Tyr Asp Lys Asp Leu Met Leu Thr Thr His Phe
        195                 200                 205

Arg Thr Arg Asn Ile Thr Asp Asn His Gly Lys Asn Lys Thr Thr Val
    210                 215                 220

His Gly Tyr Phe Ser Ser Ile Phe Leu Gly Gly Val Asp Ser Leu Val
225                 230                 235                 240

Asp Leu Met Asn Lys Ser Phe Pro Glu Leu Gly Ile Lys Lys Thr Asp
                245                 250                 255

Cys Lys Glu Leu Ser Trp Ile Asp Thr Thr Ile Phe Tyr Ser Gly Val
            260                 265                 270

Val Asn Tyr Asn Thr Ala Asn Phe Lys Lys Glu Ile Leu Leu Asp Arg
        275                 280                 285

Ser Ala Gly Lys Lys Thr Ala Phe Ser Ile Lys Leu Asp Tyr Val Lys
    290                 295                 300

Lys Leu Ile Pro Glu Thr Ala Met Val Lys Ile Leu Glu Lys Leu Tyr
305                 310                 315                 320

Glu Glu Glu Val Gly Val Gly Met Tyr Val Leu Tyr Pro Tyr Gly Gly
                325                 330                 335

Ile Met Asp Glu Ile Ser Glu Ser Ala Ile Pro Phe Pro His Arg Ala
            340                 345                 350

Gly Ile Met Tyr Glu Leu Trp Tyr Thr Ala Thr Trp Glu Lys Gln Glu
        355                 360                 365

Asp Asn Glu Lys His Ile Asn Trp Val Arg Ser Val Tyr Asn Phe Thr
    370                 375                 380

Thr Pro Tyr Val Ser Gln Asn Pro Arg Leu Ala Tyr Leu Asn Tyr Arg
385                 390                 395                 400

Asp Leu Asp Leu Gly Lys Thr Asn Pro Glu Ser Pro Asn Asn Tyr Thr
                405                 410                 415

Gln Ala Arg Ile Trp Gly Glu Lys Tyr Phe Gly Lys Asn Phe Asn Arg
```

```
            420                 425                 430

Leu Val Lys Val Lys Thr Lys Ala Asp Pro Asn Asn Phe Phe Arg Asn
        435                 440                 445

Glu Gln Ser Ile Pro Pro Leu Pro Pro Arg His His
    450                 455                 460


<210> SEQ ID NO 9
<211> LENGTH: 545
<212> TYPE: PRT
<213> ORGANISM: Unknown
<220> FEATURE:
<223> OTHER INFORMATION: Description of Unknown:
      CBCAS sequence

<400> SEQUENCE: 9

Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Val Val Pro Ser Lys Ala Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Met
        275                 280                 285

Leu Thr Thr His Phe Arg Thr Arg Asn Ile Thr Asp Asn His Gly Lys
    290                 295                 300

Asn Lys Thr Thr Val His Gly Tyr Phe Ser Ser Ile Phe Leu Gly Gly
305                 310                 315                 320
```

```
Val Asp Ser Leu Val Asp Leu Met Asn Lys Ser Phe Pro Glu Leu Gly
                325                 330                 335

Ile Lys Lys Thr Asp Cys Lys Glu Leu Ser Trp Ile Asp Thr Thr Ile
            340                 345                 350

Phe Tyr Ser Gly Val Val Asn Tyr Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Leu Ile Pro Glu Thr Ala Met Val Lys Ile
385                 390                 395                 400

Leu Glu Lys Leu Tyr Glu Glu Glu Val Gly Val Gly Met Tyr Val Leu
                405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Leu Trp Tyr Thr Ala Thr
        435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Ala Asp Pro Asn
        515                 520                 525

Asn Phe Phe Arg Asn Glu Gln Ser Ile Pro Pro Leu Pro Pro Arg His
    530                 535                 540

His
545


<210> SEQ ID NO 10
<211> LENGTH: 579
<212> TYPE: PRT
<213> ORGANISM: Streptomyces sp.

<400> SEQUENCE: 10

Met Glu Leu Ala Leu Pro Ala Glu Leu Ala Pro Thr Leu Pro Glu Ala
1               5                   10                  15

Leu Arg Leu Arg Ser Glu Gln Gln Pro Asp Thr Val Ala Tyr Val Phe
            20                  25                  30

Leu Arg Asp Gly Glu Thr Pro Glu Glu Thr Leu Thr Tyr Gly Arg Leu
        35                  40                  45

Asp Arg Ala Ala Arg Ala Arg Ala Ala Ala Leu Glu Ala Ala Gly Leu
    50                  55                  60

Ala Gly Gly Thr Ala Val Leu Leu Tyr Pro Ser Gly Leu Glu Phe Val
65                  70                  75                  80

Ala Ala Leu Leu Gly Cys Met Tyr Ala Gly Thr Ala Gly Ala Pro Val
                85                  90                  95

Gln Val Pro Thr Arg Arg Arg Gly Met Glu Arg Ala Arg Arg Ile Ala
            100                 105                 110

Asp Asp Ala Gly Ala Lys Thr Ile Leu Thr Thr Thr Ala Val Lys Arg
        115                 120                 125

Glu Val Glu Glu His Phe Ala Asp Leu Leu Thr Gly Leu Thr Val Ile
    130                 135                 140
```

-continued

```
Asp Thr Glu Ser Leu Pro Asp Val Pro Asp Asp Ala Pro Ala Val Arg
145                 150                 155                 160

Leu Pro Gly Pro Asp Asp Val Ala Leu Leu Gln Tyr Thr Ser Gly Ser
                165                 170                 175

Thr Gly Asp Pro Lys Gly Val Glu Val Thr His Ala Asn Phe Arg Ala
            180                 185                 190

Asn Val Ala Glu Thr Val Glu Leu Trp Pro Val Arg Ser Asp Gly Thr
        195                 200                 205

Val Val Asn Trp Leu Pro Leu Phe His Asp Met Gly Leu Met Phe Gly
    210                 215                 220

Val Val Met Pro Leu Phe Thr Gly Val Pro Ala Tyr Leu Met Ala Pro
225                 230                 235                 240

Gln Ser Phe Ile Arg Arg Pro Ala Arg Trp Leu Glu Ala Ile Ser Arg
                245                 250                 255

Phe Arg Gly Thr His Ala Ala Ala Pro Ser Phe Ala Tyr Glu Leu Cys
            260                 265                 270

Val Arg Ser Val Ala Asp Thr Gly Leu Pro Ala Gly Leu Asp Leu Ser
        275                 280                 285

Ser Trp Arg Val Ala Val Asn Gly Ala Glu Pro Val Arg Trp Thr Ala
    290                 295                 300

Val Ala Asp Phe Thr Glu Ala Tyr Ala Pro Ala Gly Phe Arg Pro Gln
305                 310                 315                 320

Ala Met Cys Pro Gly Tyr Gly Leu Ala Glu Asn Thr Leu Lys Leu Ser
                325                 330                 335

Gly Ser Pro Glu Asp Arg Pro Pro Thr Leu Leu Arg Ala Asp Ala Ala
            340                 345                 350

Ala Leu Gln Asp Gly Arg Val Val Pro Leu Thr Gly Pro Gly Thr Asp
        355                 360                 365

Gly Val Arg Leu Val Gly Ser Gly Val Thr Val Pro Ser Ser Arg Val
    370                 375                 380

Ala Val Val Asp Pro Gly Thr Gly Thr Glu Gln Pro Ala Gly Arg Val
385                 390                 395                 400

Gly Glu Ile Trp Ile Asn Gly Pro Cys Val Ala Arg Gly Tyr His Gly
                405                 410                 415

Arg Pro Ala Glu Ser Ala Glu Ser Phe Gly Ala Arg Ile Ala Gly Gln
            420                 425                 430

Glu Ala Arg Gly Thr Trp Leu Arg Thr Gly Asp Leu Gly Phe Leu His
        435                 440                 445

Asp Gly Glu Val Phe Val Ala Gly Arg Leu Lys Asp Val Val Ile His
    450                 455                 460

Gln Gly Arg Asn Phe Tyr Pro Gln Asp Ile Glu Leu Ser Ala Glu Val
465                 470                 475                 480

Ser Asp Arg Ala Leu His Pro Asn Cys Ala Ala Ala Phe Ala Leu Asp
                485                 490                 495

Asp Gly Arg Thr Glu Arg Leu Val Leu Leu Val Glu Ala Asp Gly Arg
            500                 505                 510

Ala Leu Arg Asn Gly Gly Ala Asp Ala Leu Arg Ala Arg Val His Asp
        515                 520                 525

Ala Val Trp Asp Arg Gln Arg Leu Arg Ile Asp Glu Ile Val Leu Leu
    530                 535                 540

Arg Arg Gly Ala Leu Pro Lys Thr Ser Ser Gly Lys Val Gln Arg Arg
545                 550                 555                 560
```

-continued

```
Leu Ala Arg Ser Arg Tyr Leu Asp Gly Glu Phe Gly Pro Ala Pro Ala
                565                 570                 575

Arg Glu Ala


<210> SEQ ID NO 11
<211> LENGTH: 543
<212> TYPE: PRT
<213> ORGANISM: Cannabis sativa

<400> SEQUENCE: 11

Met Glu Lys Ser Gly Tyr Gly Arg Asp Gly Ile Tyr Arg Ser Leu Arg
1               5                   10                  15

Pro Pro Leu His Leu Pro Asn Asn Asn Asn Leu Ser Met Val Ser Phe
            20                  25                  30

Leu Phe Arg Asn Ser Ser Ser Tyr Pro Gln Lys Pro Ala Leu Ile Asp
        35                  40                  45

Ser Glu Thr Asn Gln Ile Leu Ser Phe Ser His Phe Lys Ser Thr Val
    50                  55                  60

Ile Lys Val Ser His Gly Phe Leu Asn Leu Gly Ile Lys Lys Asn Asp
65                  70                  75                  80

Val Val Leu Ile Tyr Ala Pro Asn Ser Ile His Phe Pro Val Cys Phe
                85                  90                  95

Leu Gly Ile Ile Ala Ser Gly Ala Ile Ala Thr Thr Ser Asn Pro Leu
            100                 105                 110

Tyr Thr Val Ser Glu Leu Ser Lys Gln Val Lys Asp Ser Asn Pro Lys
        115                 120                 125

Leu Ile Ile Thr Val Pro Gln Leu Leu Glu Lys Val Lys Gly Phe Asn
    130                 135                 140

Leu Pro Thr Ile Leu Ile Gly Pro Asp Ser Glu Gln Glu Ser Ser Ser
145                 150                 155                 160

Asp Lys Val Met Thr Phe Asn Asp Leu Val Asn Leu Gly Gly Ser Ser
                165                 170                 175

Gly Ser Glu Phe Pro Ile Val Asp Asp Phe Lys Gln Ser Asp Thr Ala
            180                 185                 190

Ala Leu Leu Tyr Ser Ser Gly Thr Thr Gly Met Ser Lys Gly Val Val
        195                 200                 205

Leu Thr His Lys Asn Phe Ile Ala Ser Ser Leu Met Val Thr Met Glu
    210                 215                 220

Gln Asp Leu Val Gly Glu Met Asp Asn Val Phe Leu Cys Phe Leu Pro
225                 230                 235                 240

Met Phe His Val Phe Gly Leu Ala Ile Ile Thr Tyr Ala Gln Leu Gln
                245                 250                 255

Arg Gly Asn Thr Val Ile Ser Met Ala Arg Phe Asp Leu Glu Lys Met
            260                 265                 270

Leu Lys Asp Val Glu Lys Tyr Lys Val Thr His Leu Trp Val Val Pro
        275                 280                 285

Pro Val Ile Leu Ala Leu Ser Lys Asn Ser Met Val Lys Lys Phe Asn
    290                 295                 300

Leu Ser Ser Ile Lys Tyr Ile Gly Ser Gly Ala Ala Pro Leu Gly Lys
305                 310                 315                 320

Asp Leu Met Glu Glu Cys Ser Lys Val Val Pro Tyr Gly Ile Val Ala
                325                 330                 335

Gln Gly Tyr Gly Met Thr Glu Thr Cys Gly Ile Val Ser Met Glu Asp
            340                 345                 350
```

Ile Arg Gly Gly Lys Arg Asn Ser Gly Ser Ala Gly Met Leu Ala Ser
355 360 365

Gly Val Glu Ala Gln Ile Val Ser Val Asp Thr Leu Lys Pro Leu Pro
370 375 380

Pro Asn Gln Leu Gly Glu Ile Trp Val Lys Gly Pro Asn Met Met Gln
385 390 395 400

Gly Tyr Phe Asn Asn Pro Gln Ala Thr Lys Leu Thr Ile Asp Lys Lys
405 410 415

Gly Trp Val His Thr Gly Asp Leu Gly Tyr Phe Asp Glu Asp Gly His
420 425 430

Leu Tyr Val Val Asp Arg Ile Lys Glu Leu Ile Lys Tyr Lys Gly Phe
435 440 445

Gln Val Ala Pro Ala Glu Leu Glu Gly Leu Leu Val Ser His Pro Glu
450 455 460

Ile Leu Asp Ala Val Val Ile Pro Phe Pro Asp Ala Glu Ala Gly Glu
465 470 475 480

Val Pro Val Ala Tyr Val Val Arg Ser Pro Asn Ser Ser Leu Thr Glu
485 490 495

Asn Asp Val Lys Lys Phe Ile Ala Gly Gln Val Ala Ser Phe Lys Arg
500 505 510

Leu Arg Lys Val Thr Phe Ile Asn Ser Val Pro Lys Ser Ala Ser Gly
515 520 525

Lys Ile Leu Arg Arg Glu Leu Ile Gln Lys Val Arg Ser Asn Met
530 535 540

<210> SEQ ID NO 12
<211> LENGTH: 720
<212> TYPE: PRT
<213> ORGANISM: Cannabis sativa

<400> SEQUENCE: 12

Met Gly Lys Asn Tyr Lys Ser Leu Asp Ser Val Val Ala Ser Asp Phe
1 5 10 15

Ile Ala Leu Gly Ile Thr Ser Glu Val Ala Glu Thr Leu His Gly Arg
20 25 30

Leu Ala Glu Ile Val Cys Asn Tyr Gly Ala Ala Thr Pro Gln Thr Trp
35 40 45

Ile Asn Ile Ala Asn His Ile Leu Ser Pro Asp Leu Pro Phe Ser Leu
50 55 60

His Gln Met Leu Phe Tyr Gly Cys Tyr Lys Asp Phe Gly Pro Ala Pro
65 70 75 80

Pro Ala Trp Ile Pro Asp Pro Glu Lys Val Lys Ser Thr Asn Leu Gly
85 90 95

Ala Leu Leu Glu Lys Arg Gly Lys Glu Phe Leu Gly Val Lys Tyr Lys
100 105 110

Asp Pro Ile Ser Ser Phe Ser His Phe Gln Glu Phe Ser Val Arg Asn
115 120 125

Pro Glu Val Tyr Trp Arg Thr Val Leu Met Asp Glu Met Lys Ile Ser
130 135 140

Phe Ser Lys Asp Pro Glu Cys Ile Leu Arg Arg Asp Asp Ile Asn Asn
145 150 155 160

Pro Gly Gly Ser Glu Trp Leu Pro Gly Gly Tyr Leu Asn Ser Ala Lys
165 170 175

Asn Cys Leu Asn Val Asn Ser Asn Lys Lys Leu Asn Asp Thr Met Ile
180 185 190

```
Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415

Leu Asn Gly Ala Ser Ile Ala Leu Tyr Asn Gly Ser Pro Leu Val Ser
            420                 425                 430

Gly Phe Ala Lys Phe Val Gln Asp Ala Lys Val Thr Met Leu Gly Val
        435                 440                 445

Val Pro Ser Ile Val Arg Ser Trp Lys Ser Thr Asn Cys Val Ser Gly
    450                 455                 460

Tyr Asp Trp Ser Thr Ile Arg Cys Phe Ser Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605
```

```
Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720


<210> SEQ ID NO 13
<211> LENGTH: 385
<212> TYPE: PRT
<213> ORGANISM: Cannabis sativa

<400> SEQUENCE: 13

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270
```

```
Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380

Tyr
385


<210> SEQ ID NO 14
<211> LENGTH: 101
<212> TYPE: PRT
<213> ORGANISM: Cannabis sativa

<400> SEQUENCE: 14

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Arg Lys
            100


<210> SEQ ID NO 15
<211> LENGTH: 99
<212> TYPE: PRT
<213> ORGANISM: Cannabis sativa

<400> SEQUENCE: 15

Ala Val Lys His Leu Ile Val Leu Lys Phe Lys Asp Glu Ile Thr Glu
1               5                   10                  15

Ala Gln Lys Glu Glu Phe Phe Lys Thr Tyr Val Asn Leu Val Asn Ile
            20                  25                  30

Ile Pro Ala Met Lys Asp Val Tyr Trp Gly Lys Asp Val Thr Gln Lys
        35                  40                  45

Asn Lys Glu Glu Gly Tyr Thr His Ile Val Glu Val Thr Phe Glu Ser
    50                  55                  60

Val Glu Thr Ile Gln Asp Tyr Ile Ile His Pro Ala His Val Gly Phe
65                  70                  75                  80

Gly Asp Val Tyr Arg Ser Phe Trp Glu Lys Leu Leu Ile Phe Asp Tyr
                85                  90                  95
```

Thr Pro Arg

<210> SEQ ID NO 16
<211> LENGTH: 95
<212> TYPE: PRT
<213> ORGANISM: Cannabis sativa

<400> SEQUENCE: 16

```
Ala Val Lys His Leu Ile Val Leu Lys Phe Lys Asp Glu Ile Thr Glu
1               5                   10                  15

Ala Gln Lys Glu Glu Phe Phe Lys Thr Tyr Val Asn Leu Val Asn Ile
            20                  25                  30

Ile Pro Ala Met Lys Asp Val Tyr Trp Gly Lys Asp Val Thr Gln Lys
        35                  40                  45

Asn Lys Glu Glu Gly Tyr Thr His Ile Val Glu Val Thr Phe Glu Ser
    50                  55                  60

Val Glu Thr Ile Gln Asp Tyr Ile Ile His Pro Ala His Val Gly Phe
65                  70                  75                  80

Gly Asp Val Tyr Arg Ser Phe Trp Glu Lys Leu Leu Ile Phe Asp
                85                  90                  95
```

<210> SEQ ID NO 17
<211> LENGTH: 472
<212> TYPE: PRT
<213> ORGANISM: Unknown
<220> FEATURE:
<223> OTHER INFORMATION: Description of Unknown:
      CBDAS sequence

<400> SEQUENCE: 17

```
Met Asn Phe Arg Phe Ser Ser Pro Ser Leu Pro Lys Pro Ser Val Ile
1               5                   10                  15

Ile Thr Pro Phe His Val Ser Gln Ile Lys Ala Thr Leu Met Cys Ser
            20                  25                  30

Lys Lys His Gly Leu Gln Ile Arg Thr Arg Ser Gly Gly His Asp Ser
        35                  40                  45

Asp Gly Leu Ser Tyr Ile Ser Asp Val Pro Tyr Val Val Ile Asp Leu
    50                  55                  60

Arg Asn Leu Ser Lys Val Lys Val Asp Val His Asp Lys Thr Ala Trp
65                  70                  75                  80

Val Gln Ala Gly Ala Thr Ile Gly Glu Val Tyr Tyr Asn Ile Ala Lys
                85                  90                  95

Lys Ser Pro Ile Leu Gly Phe Pro Ala Gly Ile Cys Tyr Thr Val Gly
            100                 105                 110

Val Gly Gly His Phe Ser Gly Gly Gly Tyr Gly Ile Leu Met Arg Lys
        115                 120                 125

Tyr Gly Leu Gly Gly Asp Asn Val Ile Asp Val Arg Ile Leu Leu Ala
    130                 135                 140

Asn Gly Lys Ile Val Asp Arg Lys Ser Met Gly Gly Asp Leu Phe Trp
145                 150                 155                 160

Ala Leu Arg Gly Gly Gly Ala Val Ser Phe Gly Ile Val Leu Ala Trp
                165                 170                 175

Lys Ile Asn Leu Val Asp Ile Pro Ser Thr Ile Thr Ile Ala Asn Val
            180                 185                 190

Gln Met Asp Tyr Glu Gln Asp Ser Thr Lys Arg Leu Val His Gln Trp
        195                 200                 205
```

Gln Thr Ile Ala Asp Lys Phe Asp Lys Asp Leu Leu Leu Phe Val Arg
    210                 215                 220

Leu Gln Thr Gly Asn Ser Thr Thr Pro Gly Ile Thr Lys Pro Ser Leu
225                 230                 235                 240

Gln Ala Ser Phe Ala Val Val Phe Leu Gly Gly Thr Asp Lys Leu Ile
                245                 250                 255

Pro Leu Val Lys Lys Ser Phe Pro Asp Leu Gly Leu Ala Arg Lys Asp
            260                 265                 270

Cys Val Glu Met Ser Trp Ile Gln Ser Ile Leu Leu Phe Asn Gly Phe
        275                 280                 285

Pro Thr Asn Ser Ser Leu Asp Val Leu Leu Asn Arg Thr Gln Ser Val
    290                 295                 300

Met Phe Ser Phe Lys Ala Lys Ala Asp Tyr Val Lys Glu Pro Ile Pro
305                 310                 315                 320

Asp Asp Val Val Asp Lys Leu Ala Lys Ser Leu Tyr Gln Glu Asp Leu
                325                 330                 335

Gly Thr Ala Val Leu Gln Leu Phe Pro Tyr Gly Gly Arg Met Gly Glu
            340                 345                 350

Ile Pro Glu Ser Glu Thr Pro Phe Pro His Arg Ser Gly Asn Leu Tyr
        355                 360                 365

Glu Leu Thr Tyr Leu Ala Arg Trp Val Glu Lys Gly Asn Ala Ser Glu
    370                 375                 380

Thr Glu Asn His Leu Lys Trp Thr Arg Ser Ser Tyr Ser Tyr Met Ala
385                 390                 395                 400

Pro Tyr Val Ser Lys Asn Pro Arg Glu Ala Tyr Leu Asn Tyr Arg Asp
                405                 410                 415

Leu Asp Ile Gly Arg Asn Asn Tyr Asn Gly Ser Thr Thr Tyr Ala Gln
            420                 425                 430

Ala Ser Ile Trp Gly Ser Lys Tyr Tyr Lys Asp Asn Phe Lys Arg Leu
        435                 440                 445

Val Tyr Val Lys Thr Met Val Asp Pro Ser Asn Phe Phe Arg Asn Glu
    450                 455                 460

Gln Ser Ile Pro Ala Tyr Ser Leu
465                 470

<210> SEQ ID NO 18
<211> LENGTH: 557
<212> TYPE: PRT
<213> ORGANISM: Unknown
<220> FEATURE:
<223> OTHER INFORMATION: Description of Unknown:
      CBDAS sequence

<400> SEQUENCE: 18

Met Lys Leu Arg Asp Ser Ser Ile Phe Pro Ser Val Ile Val Phe Met
1               5                   10                  15

Ile Ile Ile Ser Leu Ser Ser Thr Thr Lys Ala Tyr Ala Thr Leu His
            20                  25                  30

Asp Tyr Gln Tyr Thr Lys Thr Asn Phe Ile Gln Cys Leu Ser His His
        35                  40                  45

Ser Ser Ser Asn Ser Ser His Asn Asn Asp Ile Thr Lys Val Val Tyr
    50                  55                  60

Ser Thr Thr Asn Ser Ser Tyr Phe Ser Val Leu Asn Phe Thr Ile Ile
65                  70                  75                  80

Asn Pro Arg Phe Ser Ser Pro Ser Thr Pro Lys Pro Leu Phe Ile Ile
                85                  90                  95

-continued

```
Thr Pro Leu His Glu Ser His Val Gln Ala Ala Val Val Cys Ser Arg
            100                 105                 110

Lys His Gly Val Gln Ile Arg Ile Arg Ser Gly Gly His Asp Tyr Glu
        115                 120                 125

Gly Leu Ser Tyr Val Ser Asp Val Pro Phe Val Val Ile Asp Leu Ile
    130                 135                 140

Asn His Arg Ser Ile Thr Ile Asp Val Glu Lys Arg Thr Ala Trp Val
145                 150                 155                 160

Gln Ala Gly Ala Thr Leu Gly Glu Leu Tyr Tyr Glu Ile Asn Val Lys
                165                 170                 175

Ser Lys Thr Leu Ala Phe Pro Ala Gly Ala Cys Pro Thr Ile Gly Val
            180                 185                 190

Gly Gly His Ile Ser Gly Gly Gly Tyr Gly Ser Ile Phe Arg Lys Tyr
        195                 200                 205

Gly Leu Ala Ala Asp Asn Val Ile Asp Ala Gln Ile Val Asp Val Glu
    210                 215                 220

Gly Arg Val Leu Asp Arg Glu Thr Met Gly Glu Asp Leu Phe Trp Ala
225                 230                 235                 240

Ile Arg Gly Gly Gly Gly Ala Ser Phe Gly Val Ile Leu Ala Trp Lys
                245                 250                 255

Val Arg Leu Val Pro Val Pro Glu Thr Val Thr Val Phe Ala Ile Asn
            260                 265                 270

Arg Asn Leu Glu His Asn Val Thr Lys Leu Val His Arg Trp Gln Tyr
        275                 280                 285

Ile Ala Asp Lys Leu His Lys Asp Leu Leu Leu Ala Val Arg Phe Gln
    290                 295                 300

Thr Val Lys Val Asn Ser Thr Gln Glu Gly Ser Tyr Lys Lys Glu Leu
305                 310                 315                 320

Gln Ala Thr Phe Ile Ser Val Phe Leu Gly Arg Val Asp Gly Leu Leu
                325                 330                 335

Asp Leu Met Gly Lys Arg Phe Pro Glu Leu Gly Leu Ala Arg Glu Asp
            340                 345                 350

Cys Thr Glu Met Ser Trp Ile Glu Ser Ala Leu Phe Val Ala Gly Leu
        355                 360                 365

Pro Arg Glu Gln Ser Pro Glu Ile Leu Leu Asp Arg Thr Pro Gln Ser
    370                 375                 380

Arg Leu Ser Phe Lys Ala Lys Ser Asp Tyr Val Lys Glu Pro Ile Pro
385                 390                 395                 400

Glu Lys Gly Leu Glu Gly Ile Trp Glu Arg Leu Tyr Glu Glu Glu Ile
                405                 410                 415

Gly Arg Gly Val Val Ile Met Ser Pro Tyr Gly Gly Lys Met Ser Glu
            420                 425                 430

Ile Ser Glu Ser Glu Leu Pro Phe Gly His Arg Ala Gly Asn Leu Tyr
        435                 440                 445

Lys Ile Gln Tyr Leu Ile Tyr Trp Glu Glu Glu Gly Asn Ala Thr Val
    450                 455                 460

Met Glu Lys His Ile Ser Trp Ile Arg Arg Leu Tyr Tyr Tyr Met Thr
465                 470                 475                 480

Gln Phe Val Ser Lys Asn Pro Arg Ser Ala Tyr Ile Asn Tyr Arg Asp
                485                 490                 495

Leu Asp Ile Gly Thr Asn Ser Asn Asn Gly Thr Ala Ser Tyr Ala Gln
            500                 505                 510
```

-continued

Ala Ser Ile Trp Gly Val Lys Tyr Phe Gly His Asn Asn Phe Asn Arg
        515                 520                 525

Leu Val His Val Lys Thr Ile Val Asp Pro Thr Asn Phe Phe Arg Asn
    530                 535                 540

Glu Gln Ser Ile Pro Pro Leu Arg Ile Glu Tyr Ser Ser
545                 550                 555

<210> SEQ ID NO 19
<211> LENGTH: 542
<212> TYPE: PRT
<213> ORGANISM: Unknown
<220> FEATURE:
<223> OTHER INFORMATION: Description of Unknown:
      CBDAS sequence

<400> SEQUENCE: 19

Met Lys His Ser Val Phe Ser Tyr Trp Phe Leu Cys Lys Ile Val Asn
1               5                   10                  15

Ile Ser Leu Leu Ser Phe Ser Ile Arg Ser Thr Arg Ala Asp Pro His
            20                  25                  30

Ala Asp Phe Leu Gln Cys Phe Ser Gln Tyr Ile Ser Asn Ser Thr Thr
        35                  40                  45

Ile Ala Lys Leu Ile Tyr Thr Pro Asn Asp Pro Leu Tyr Ile Ser Ile
    50                  55                  60

Leu Asn Ser Thr Ile Gln Asn Asn Arg Phe Ser Ser Pro Ser Thr Pro
65                  70                  75                  80

Lys Pro Leu Ile Ile Ile Thr Pro Leu Asn Ser Phe His Val Gln Ala
                85                  90                  95

Ser Ile Leu Cys Ser Arg Lys Tyr Gly Leu Gln Ile Arg Thr Arg Ser
            100                 105                 110

Gly Gly His Asp Phe Glu Gly Val Ser Tyr Val Ser Glu Val Pro Phe
        115                 120                 125

Val Ile Val Asp Met Arg Asn Leu Arg Ser Ile Thr Ile Asp Val Asp
    130                 135                 140

Asn Lys Thr Ala Trp Val Asp Val Gly Ala Thr Leu Gly Glu Leu Tyr
145                 150                 155                 160

Tyr Arg Ile Ala Glu Lys Asn Glu Asn Leu Ser Phe Pro Ala Gly Tyr
                165                 170                 175

Cys His Thr Val Gly Val Gly Gly His Phe Ser Gly Gly Gly Tyr Gly
            180                 185                 190

Ala Leu Met Arg Lys Tyr Gly Leu Ala Ala Asp Asn Val Ile Asp Ala
        195                 200                 205

His Leu Val Asn Val Asp Gly Glu Val Leu Asp Arg Gln Ser Met Gly
    210                 215                 220

Glu Asp Leu Phe Trp Ala Ile Arg Gly Gly Gly Gly Ala Ser Phe Gly
225                 230                 235                 240

Ile Ile Leu Ala Trp Lys Ile Arg Leu Val Pro Val Pro Ser Lys Val
                245                 250                 255

Thr Ile Val Ser Ile Asn Lys Asn Leu Glu Ile Asn Glu Thr Val Lys
            260                 265                 270

Leu Tyr Asn Lys Trp Gln Asn Ile Ala His Lys Phe Asp Lys Asp Leu
        275                 280                 285

Leu Ile Phe Val Arg Phe Thr Thr Met Asn Ser Thr Asp Gly Gln Gly
    290                 295                 300

Lys Asn Lys Thr Ala Ile Leu Thr Ser Phe Tyr Ser Ile Phe Phe Gly
305                 310                 315                 320

Gly Met Asp Gly Leu Leu Ala Leu Met Glu Lys Ser Phe Pro Glu Leu
325 330 335

Asp Val Lys Arg Lys Asp Cys Phe Glu Ala Ser Trp Ile Glu Met Ile
340 345 350

Phe Tyr Phe Asn Gly Phe Ser Ser Gly Asp Lys Leu Glu Val Leu Leu
355 360 365

Gly Arg Thr Asn Glu Glu Lys Gly Phe Phe Lys Ala Lys Leu Asp Tyr
370 375 380

Val Arg Lys Pro Ile Pro Glu Thr Val Ile Val Lys Leu Leu Glu Lys
385 390 395 400

Leu Tyr Asn Glu Asp Val Gly Leu Gly Leu Ile Gln Met Tyr Pro Tyr
405 410 415

Gly Gly Lys Met Asp Glu Ile Pro Glu Ser Ala Ile Pro Phe Pro His
420 425 430

Arg Val Gly Phe Ile Tyr Lys Ile Leu Tyr Leu Ser Gln Trp Glu Lys
435 440 445

Glu Glu Glu Gly Glu Arg His Leu Asn Trp Val Arg Ser Val Tyr Asn
450 455 460

Tyr Met Thr Pro Phe Val Ser Lys Ser Pro Arg Ala Ser Tyr Leu Asn
465 470 475 480

Tyr Arg Asp Phe Asp Leu Gly Thr Asn Asn Lys Asn Gly Pro Thr Ser
485 490 495

Tyr Gly Gln Ala Ser Ile Trp Gly Lys Lys Tyr Phe Asp Lys Asn Phe
500 505 510

Lys Arg Leu Val His Val Lys Thr Lys Val Asp Pro Thr Asn Phe Phe
515 520 525

Arg Asn Glu Gln Ser Ile Pro Pro Leu Ser Val Arg Gly Leu
530 535 540

<210> SEQ ID NO 20
<211> LENGTH: 446
<212> TYPE: PRT
<213> ORGANISM: Roseburia hominis

<400> SEQUENCE: 20

Met Asp Phe Arg Glu Glu Tyr Lys Gln Lys Leu Val Ser Ala Asp Glu
1 5 10 15

Ala Val Lys Leu Ile Lys Ser Gly Asp Trp Val Asp Tyr Gly Trp Cys
20 25 30

Thr Asn Thr Val Asp Ala Leu Asp Gln Ala Leu Ala Lys Arg Thr Asp
35 40 45

Glu Leu Thr Asp Val Lys Leu Arg Gly Gly Ile Leu Met Lys Pro Leu
50 55 60

Ala Val Phe Ala Arg Glu Asp Ala Gly Glu His Phe Cys Trp Asn Ser
65 70 75 80

Trp His Met Ser Gly Ile Glu Arg Lys Met Ile Asn Arg Gly Val Ala
85 90 95

Tyr Tyr Cys Pro Ile Arg Tyr Ser Glu Leu Pro Arg Tyr Tyr Arg Glu
100 105 110

Leu Asp Cys Pro Asp Asp Val Ala Met Phe Gln Val Ala Pro Met Asp
115 120 125

Ala His Gly Tyr Phe Asn Phe Gly Pro Ser Ala Ser His Leu Gly Ala
130 135 140

Met Cys Glu Arg Ala Lys His Ile Ile Val Glu Val Asn Glu Asn Met

```
145                 150                 155                 160

Pro Arg Cys Leu Gly Gly Thr Glu Cys Gly Ile His Ile Ser Asp Val
                165                 170                 175

Thr Tyr Ile Val Glu Gly Ser Asn Pro Pro Ile Gly Glu Leu Gly Ala
            180                 185                 190

Gly Gly Pro Ala Thr Asp Val Asp Lys Ala Val Ala Lys Leu Ile Val
        195                 200                 205

Asp Glu Ile Pro Asn Gly Ala Cys Leu Gln Leu Gly Ile Gly Gly Met
    210                 215                 220

Pro Asn Ala Val Gly Ser Leu Ile Ala Glu Ser Asp Leu Lys Asp Leu
225                 230                 235                 240

Gly Val His Thr Glu Met Tyr Val Asp Ala Phe Val Asp Ile Ala Lys
                245                 250                 255

Ala Gly Lys Ile Asn Gly Ser Lys Lys Asn Ile Asp Arg Tyr Arg Gln
            260                 265                 270

Thr Tyr Ala Phe Gly Ala Gly Thr Lys Lys Met Tyr Asp Tyr Leu Asp
        275                 280                 285

Asp Asn Pro Glu Leu Met Ser Ala Pro Val Asp Tyr Thr Asn Asp Ile
    290                 295                 300

Arg Ser Ile Ser Ala Leu Asp Asn Phe Ile Ser Ile Asn Asn Ala Val
305                 310                 315                 320

Asp Ile Asp Leu Tyr Gly Gln Val Asn Ala Glu Ser Ala Gly Ile Lys
                325                 330                 335

Gln Ile Ser Gly Ala Gly Gly Gln Leu Asp Phe Val Leu Gly Ala Tyr
            340                 345                 350

Leu Ser Lys Gly Gly Lys Ser Phe Ile Cys Leu Ser Ser Thr Phe Lys
        355                 360                 365

Thr Lys Asp Gly Gln Val Gln Ser Arg Ile Arg Pro Thr Leu Ala Asn
    370                 375                 380

Gly Ser Ile Val Thr Asp Ala Arg Pro Asn Thr His Tyr Val Val Thr
385                 390                 395                 400

Glu Tyr Gly Lys Val Asn Leu Lys Gly Leu Ser Thr Trp Gln Arg Ala
                405                 410                 415

Glu Ala Leu Ile Ser Ile Ala His Pro Asp Phe Arg Asp Asp Leu Ile
            420                 425                 430

Lys Glu Ala Glu Gln Met His Ile Trp Arg Arg Ser Asn Arg
        435                 440                 445


<210> SEQ ID NO 21
<211> LENGTH: 216
<212> TYPE: PRT
<213> ORGANISM: Escherichia coli

<400> SEQUENCE: 21

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80
```

```
Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215


<210> SEQ ID NO 22
<211> LENGTH: 180
<212> TYPE: PRT
<213> ORGANISM: Escherichia coli

<400> SEQUENCE: 22

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu
            180


<210> SEQ ID NO 23
<211> LENGTH: 542
<212> TYPE: PRT
<213> ORGANISM: Cupriavidus necator

<400> SEQUENCE: 23
```

-continued

```
Met Lys Val Ile Thr Ala Arg Glu Ala Ala Ala Leu Val Gln Asp Gly
1               5                   10                  15

Trp Thr Val Ala Ser Ala Gly Phe Val Gly Ala Gly His Ala Glu Ala
            20                  25                  30

Val Thr Glu Ala Leu Glu Gln Arg Phe Leu Gln Ser Gly Leu Pro Arg
        35                  40                  45

Asp Leu Thr Leu Val Tyr Ser Ala Gly Gln Gly Asp Arg Gly Ala Arg
    50                  55                  60

Gly Val Asn His Phe Gly Asn Ala Gly Met Thr Ala Ser Ile Val Gly
65                  70                  75                  80

Gly His Trp Arg Ser Ala Thr Arg Leu Ala Thr Leu Ala Met Ala Glu
                85                  90                  95

Gln Cys Glu Gly Tyr Asn Leu Pro Gln Gly Val Leu Thr His Leu Tyr
            100                 105                 110

Arg Ala Ile Ala Gly Gly Lys Pro Gly Val Met Thr Lys Ile Gly Leu
        115                 120                 125

His Thr Phe Val Asp Pro Arg Thr Ala Gln Asp Ala Arg Tyr His Gly
    130                 135                 140

Gly Ala Val Asn Glu Arg Ala Arg Gln Ala Ile Ala Glu Gly Lys Ala
145                 150                 155                 160

Cys Trp Val Asp Ala Val Asp Phe Arg Gly Asp Glu Tyr Leu Phe Tyr
                165                 170                 175

Pro Ser Phe Pro Ile His Cys Ala Leu Ile Arg Cys Thr Ala Ala Asp
            180                 185                 190

Ala Arg Gly Asn Leu Ser Thr His Arg Glu Ala Phe His His Glu Leu
        195                 200                 205

Leu Ala Met Ala Gln Ala Ala His Asn Ser Gly Gly Ile Val Ile Ala
    210                 215                 220

Gln Val Glu Ser Leu Val Asp His His Glu Ile Leu Gln Ala Ile His
225                 230                 235                 240

Val Pro Gly Ile Leu Val Asp Tyr Val Val Val Cys Asp Asn Pro Ala
                245                 250                 255

Asn His Gln Met Thr Phe Ala Glu Ser Tyr Asn Pro Ala Tyr Val Thr
            260                 265                 270

Pro Trp Gln Gly Glu Ala Ala Val Ala Glu Ala Glu Ala Ala Pro Val
        275                 280                 285

Ala Ala Gly Pro Leu Asp Ala Arg Thr Ile Val Gln Arg Arg Ala Val
    290                 295                 300

Met Glu Leu Ala Arg Arg Ala Pro Arg Val Val Asn Leu Gly Val Gly
305                 310                 315                 320

Met Pro Ala Ala Val Gly Met Leu Ala His Gln Ala Gly Leu Asp Gly
                325                 330                 335

Phe Thr Leu Thr Val Glu Ala Gly Pro Ile Gly Gly Thr Pro Ala Asp
            340                 345                 350

Gly Leu Ser Phe Gly Ala Ser Ala Tyr Pro Glu Ala Val Val Asp Gln
        355                 360                 365

Pro Ala Gln Phe Asp Phe Tyr Glu Gly Gly Gly Ile Asp Leu Ala Ile
    370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Gly Phe Ile
                405                 410                 415

Asn Ile Thr Gln Ser Ala Arg Ala Val Val Phe Met Gly Thr Leu Thr
```

```
            420                 425                 430

Ala Gly Gly Leu Glu Val Arg Ala Gly Asp Gly Gly Leu Gln Ile Val
        435                 440                 445

Arg Glu Gly Arg Val Lys Lys Ile Val Pro Glu Val Ser His Leu Ser
    450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Asp Gly Glu Ala
                485                 490                 495

Arg Leu Thr Leu Val Glu Ile Ala Pro Gly Val Asp Leu Gln Arg Asp
            500                 505                 510

Val Leu Asp Gln Cys Ser Thr Pro Ile Ala Val Ala Gln Asp Leu Arg
        515                 520                 525

Glu Met Asp Ala Arg Leu Phe Gln Ala Gly Pro Leu His Leu
    530                 535                 540


<210> SEQ ID NO 24
<211> LENGTH: 550
<212> TYPE: PRT
<213> ORGANISM: Mycobacterium avium

<400> SEQUENCE: 24

Met Ser Asp Thr Thr Thr Ala Phe Thr Val Pro Ala Val Ala Lys Ala
1               5                   10                  15

Val Ala Ala Ala Ile Pro Asp Arg Glu Leu Ile Ile Gln Gly Asp Arg
            20                  25                  30

Arg Tyr Ser Tyr Arg Gln Val Ile Glu Arg Ser Asn Arg Leu Ala Ala
        35                  40                  45

Tyr Leu His Ser Gln Gly Leu Gly Cys His Thr Glu Arg Glu Ala Leu
    50                  55                  60

Ala Gly His Glu Val Gly Gln Asp Leu Leu Gly Leu Tyr Ala Tyr Asn
65                  70                  75                  80

Gly Asn Glu Phe Val Glu Ala Leu Leu Gly Ala Phe Ala Ala Arg Val
                85                  90                  95

Ala Pro Phe Asn Val Asn Phe Arg Tyr Val Lys Ser Glu Leu His Tyr
            100                 105                 110

Leu Leu Ala Asp Ser Glu Ala Thr Ala Leu Ile Tyr His Ala Ala Phe
        115                 120                 125

Ala Pro Arg Val Ala Glu Ile Leu Pro Asp Leu Pro Arg Leu Arg Val
    130                 135                 140

Leu Ile Gln Ile Ala Asp Glu Ser Gly Asn Glu Leu Leu Asp Gly Ala
145                 150                 155                 160

Val Asp Tyr Glu Asp Ala Leu Ala Ser Val Ser Ala Glu Pro Pro Pro
                165                 170                 175

Val Arg His Cys Pro Asp Asp Leu Tyr Val Leu Tyr Thr Gly Gly Thr
            180                 185                 190

Thr Gly Met Pro Lys Gly Val Leu Trp Arg Gln His Asp Ile Phe Met
        195                 200                 205

Thr Ser Phe Gly Gly Arg Asn Leu Met Thr Gly Glu Pro Ser Ser Ser
    210                 215                 220

Ile Asp Glu Ile Val Gln Arg Ala Ala Ser Gly Pro Gly Thr Lys Leu
225                 230                 235                 240

Met Ile Leu Pro Pro Leu Ile His Gly Ala Ala Gln Trp Ser Val Met
                245                 250                 255
```

```
Thr Ala Ile Thr Thr Gly Gln Thr Val Val Phe Pro Thr Val Val Asp
            260                 265                 270

His Leu Asp Ala Glu Asp Val Val Arg Thr Ile Glu Arg Glu Lys Val
        275                 280                 285

Met Val Val Thr Val Val Gly Asp Ala Met Ala Arg Pro Leu Val Ala
    290                 295                 300

Ala Ile Glu Lys Gly Ile Ala Asp Val Ser Ser Leu Ala Val Val Ala
305                 310                 315                 320

Asn Gly Gly Ala Leu Leu Thr Pro Phe Val Lys Gln Arg Leu Ile Glu
                325                 330                 335

Val Leu Pro Asn Ala Val Val Val Asp Gly Val Gly Ser Ser Glu Thr
            340                 345                 350

Gly Ala Gln Met His His Met Ser Thr Pro Gly Ala Val Ala Thr Gly
        355                 360                 365

Thr Phe Asn Ala Gly Pro Asp Thr Phe Val Ala Ala Glu Asp Leu Ser
    370                 375                 380

Ala Ile Leu Pro Pro Gly His Glu Gly Met Gly Trp Leu Ala Gln Arg
385                 390                 395                 400

Gly Tyr Val Pro Leu Gly Tyr Lys Gly Asp Ala Ala Lys Thr Ala Lys
                405                 410                 415

Thr Phe Pro Val Ile Asp Gly Val Arg Tyr Ala Val Pro Gly Asp Arg
            420                 425                 430

Ala Arg His His Ala Asp Gly His Ile Glu Leu Leu Gly Arg Asp Ser
        435                 440                 445

Val Cys Ile Asn Ser Gly Gly Glu Lys Ile Phe Val Glu Glu Val Glu
    450                 455                 460

Thr Ala Ile Ala Ser His Pro Ala Val Ala Asp Val Val Val Ala Gly
465                 470                 475                 480

Arg Pro Ser Glu Arg Trp Gly Gln Glu Val Val Ala Val Val Ala Leu
                485                 490                 495

Ser Asp Gly Ala Ala Val Asp Ala Gly Glu Leu Ile Ala His Ala Ser
            500                 505                 510

Asn Ser Leu Ala Arg Tyr Lys Leu Pro Lys Ala Ile Val Phe Arg Pro
        515                 520                 525

Val Ile Glu Arg Ser Pro Ser Gly Lys Ala Asp Tyr Arg Trp Ala Arg
    530                 535                 540

Glu Gln Ala Val Asp Gly
545                 550


<210> SEQ ID NO 25
<211> LENGTH: 544
<212> TYPE: PRT
<213> ORGANISM: Arabidopsis thaliana

<400> SEQUENCE: 25

Met Glu Lys Ser Gly Tyr Gly Arg Asp Gly Ile Tyr Arg Ser Leu Arg
1               5                   10                  15

Pro Thr Leu Val Leu Pro Lys Asp Pro Asn Thr Ser Leu Val Ser Phe
            20                  25                  30

Leu Phe Arg Asn Ser Ser Ser Tyr Pro Ser Lys Leu Ala Ile Ala Asp
        35                  40                  45

Ser Asp Thr Gly Asp Ser Leu Thr Phe Ser Gln Leu Lys Ser Ala Val
    50                  55                  60

Ala Arg Leu Ala His Gly Phe His Arg Leu Gly Ile Arg Lys Asn Asp
65                  70                  75                  80
```

```
Val Val Leu Ile Phe Ala Pro Asn Ser Tyr Gln Phe Pro Leu Cys Phe
                85                  90                  95

Leu Ala Val Thr Ala Ile Gly Gly Val Phe Thr Thr Ala Asn Pro Leu
            100                 105                 110

Tyr Thr Val Asn Glu Val Ser Lys Gln Ile Lys Asp Ser Asn Pro Lys
        115                 120                 125

Ile Ile Ile Ser Val Asn Gln Leu Phe Asp Lys Ile Lys Gly Phe Asp
    130                 135                 140

Leu Pro Val Val Leu Leu Gly Ser Lys Asp Thr Val Glu Ile Pro Pro
145                 150                 155                 160

Gly Ser Asn Ser Lys Ile Leu Ser Phe Asp Asn Val Met Glu Leu Ser
                165                 170                 175

Glu Pro Val Ser Glu Tyr Pro Phe Val Glu Ile Lys Gln Ser Asp Thr
            180                 185                 190

Ala Ala Leu Leu Tyr Ser Ser Gly Thr Thr Gly Thr Ser Lys Gly Val
        195                 200                 205

Glu Leu Thr His Gly Asn Phe Ile Ala Ala Ser Leu Met Val Thr Met
    210                 215                 220

Asp Gln Asp Leu Met Gly Glu Tyr His Gly Val Phe Leu Cys Phe Leu
225                 230                 235                 240

Pro Met Phe His Val Phe Gly Leu Ala Val Ile Thr Tyr Ser Gln Leu
                245                 250                 255

Gln Arg Gly Asn Ala Leu Val Ser Met Ala Arg Phe Glu Leu Glu Leu
            260                 265                 270

Val Leu Lys Asn Ile Glu Lys Phe Arg Val Thr His Leu Trp Val Val
        275                 280                 285

Pro Pro Val Phe Leu Ala Leu Ser Lys Gln Ser Ile Val Lys Lys Phe
    290                 295                 300

Asp Leu Ser Ser Leu Lys Tyr Ile Gly Ser Gly Ala Ala Pro Leu Gly
305                 310                 315                 320

Lys Asp Leu Met Glu Glu Cys Gly Arg Asn Ile Pro Asn Val Leu Leu
                325                 330                 335

Met Gln Gly Tyr Gly Met Thr Glu Thr Cys Gly Ile Val Ser Val Glu
            340                 345                 350

Asp Pro Arg Leu Gly Lys Arg Asn Ser Gly Ser Ala Gly Met Leu Ala
        355                 360                 365

Pro Gly Val Glu Ala Gln Ile Val Ser Val Glu Thr Gly Lys Ser Gln
    370                 375                 380

Pro Pro Asn Gln Gln Gly Glu Ile Trp Val Arg Gly Pro Asn Met Met
385                 390                 395                 400

Lys Gly Tyr Leu Asn Asn Pro Gln Ala Thr Lys Glu Thr Ile Asp Lys
                405                 410                 415

Lys Ser Trp Val His Thr Gly Asp Leu Gly Tyr Phe Asn Glu Asp Gly
            420                 425                 430

Asn Leu Tyr Val Val Asp Arg Ile Lys Glu Leu Ile Lys Tyr Lys Gly
        435                 440                 445

Phe Gln Val Ala Pro Ala Glu Leu Glu Gly Leu Leu Val Ser His Pro
    450                 455                 460

Asp Ile Leu Asp Ala Val Val Ile Pro Phe Pro Asp Glu Glu Ala Gly
465                 470                 475                 480

Glu Val Pro Ile Ala Phe Val Val Arg Ser Pro Asn Ser Ser Ile Thr
                485                 490                 495
```

```
Glu Gln Asp Ile Gln Lys Phe Ile Ala Lys Gln Val Ala Pro Tyr Lys
            500                 505                 510

Arg Leu Arg Arg Val Ser Phe Ile Ser Leu Val Pro Lys Ser Ala Ala
        515                 520                 525

Gly Lys Ile Leu Arg Arg Glu Leu Val Gln Gln Val Arg Ser Lys Met
    530                 535                 540


<210> SEQ ID NO 26
<211> LENGTH: 744
<212> TYPE: PRT
<213> ORGANISM: Saccharomyces cerevisiae

<400> SEQUENCE: 26

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220

Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
            260                 265                 270

Glu Gln Val Glu Gln Val Gly Cys Phe Asn Lys Ile Pro Ala Ile Pro
        275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335
```

-continued

```
Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
        355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
            500                 505                 510

Cys Gly Ala Ile Gly Ile Ser Ala Glu Cys Arg Leu Lys Ser Val Pro
        515                 520                 525

Glu Met Gly Tyr His Ala Asp Lys Asp Leu Lys Gly Glu Leu Gln Ile
    530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
            580                 585                 590

Phe Phe Lys Leu Ala His Gly Glu Tyr Ile Ala Pro Glu Lys Ile Glu
        595                 600                 605

Asn Ile Tyr Leu Ser Ser Cys Pro Tyr Ile Thr Gln Ile Phe Val Phe
    610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
            660                 665                 670

Arg Lys Glu Phe Leu Asn Lys Ile Asn Lys Cys Thr Asp Gly Leu Gln
        675                 680                 685

Gly Phe Glu Lys Leu His Asn Ile Lys Val Gly Leu Glu Pro Leu Thr
    690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740
```

<210> SEQ ID NO 27
<211> LENGTH: 566
<212> TYPE: PRT
<213> ORGANISM: Escherichia coli

<400> SEQUENCE: 27

Met His Pro Thr Gly Pro His Leu Gly Pro Asp Val Leu Phe Arg Glu
1 5 10 15

Ser Asn Met Lys Val Thr Leu Thr Phe Asn Glu Gln Arg Arg Ala Ala
20 25 30

Tyr Arg Gln Gln Gly Leu Trp Gly Asp Ala Ser Leu Ala Asp Tyr Trp
35 40 45

Gln Gln Thr Ala Arg Ala Met Pro Asp Lys Ile Ala Val Val Asp Asn
50 55 60

His Gly Ala Ser Tyr Thr Tyr Ser Ala Leu Asp His Ala Ala Ser Cys
65 70 75 80

Leu Ala Asn Trp Met Leu Ala Lys Gly Ile Glu Ser Gly Asp Arg Ile
85 90 95

Ala Phe Gln Leu Pro Gly Trp Cys Glu Phe Thr Val Ile Tyr Leu Ala
100 105 110

Cys Leu Lys Ile Gly Ala Val Ser Val Pro Leu Leu Pro Ser Trp Arg
115 120 125

Glu Ala Glu Leu Val Trp Val Leu Asn Lys Cys Gln Ala Lys Met Phe
130 135 140

Phe Ala Pro Thr Leu Phe Lys Gln Thr Arg Pro Val Asp Leu Ile Leu
145 150 155 160

Pro Leu Gln Asn Gln Leu Pro Gln Leu Gln Gln Ile Val Gly Val Asp
165 170 175

Lys Leu Ala Pro Ala Thr Ser Ser Leu Ser Leu Ser Gln Ile Ile Ala
180 185 190

Asp Asn Thr Ser Leu Thr Thr Ala Ile Thr Thr His Gly Asp Glu Leu
195 200 205

Ala Ala Val Leu Phe Thr Ser Gly Thr Glu Gly Leu Pro Lys Gly Val
210 215 220

Met Leu Thr His Asn Asn Ile Leu Ala Ser Glu Arg Ala Tyr Cys Ala
225 230 235 240

Arg Leu Asn Leu Thr Trp Gln Asp Val Phe Met Met Pro Ala Pro Leu
245 250 255

Gly His Ala Thr Gly Phe Leu His Gly Val Thr Ala Pro Phe Leu Ile
260 265 270

Gly Ala Arg Ser Val Leu Leu Asp Ile Phe Thr Pro Asp Ala Cys Leu
275 280 285

Ala Leu Leu Glu Gln Gln Arg Cys Thr Cys Met Leu Gly Ala Thr Pro
290 295 300

Phe Val Tyr Asp Leu Leu Asn Val Leu Glu Lys Gln Pro Ala Asp Leu
305 310 315 320

Ser Ala Leu Arg Phe Phe Leu Cys Gly Gly Thr Thr Ile Pro Lys Lys
325 330 335

Val Ala Arg Glu Cys Gln Gln Arg Gly Ile Lys Leu Leu Ser Val Tyr
340 345 350

Gly Ser Thr Glu Ser Ser Pro His Ala Val Val Asn Leu Asp Asp Pro
355 360 365

Leu Ser Arg Phe Met His Thr Asp Gly Tyr Ala Ala Ala Gly Val Glu
370 375 380

```
Ile Lys Val Val Asp Asp Ala Arg Lys Thr Leu Pro Pro Gly Cys Glu
385                 390                 395                 400

Gly Glu Glu Ala Ser Arg Gly Pro Asn Val Phe Met Gly Tyr Phe Asp
                405                 410                 415

Glu Pro Glu Leu Thr Ala Arg Ala Leu Asp Glu Glu Gly Trp Tyr Tyr
            420                 425                 430

Ser Gly Asp Leu Cys Arg Met Asp Glu Ala Gly Tyr Ile Lys Ile Thr
        435                 440                 445

Gly Arg Lys Lys Asp Ile Ile Val Arg Gly Gly Glu Asn Ile Ser Ser
    450                 455                 460

Arg Glu Val Glu Asp Ile Leu Leu Gln His Pro Lys Ile His Asp Ala
465                 470                 475                 480

Cys Val Val Ala Met Ser Asp Glu Arg Leu Gly Glu Arg Ser Cys Ala
                485                 490                 495

Tyr Val Val Leu Lys Ala Pro His His Ser Leu Ser Leu Glu Glu Val
            500                 505                 510

Val Ala Phe Phe Ser Arg Lys Arg Val Ala Lys Tyr Lys Tyr Pro Glu
        515                 520                 525

His Ile Val Val Ile Glu Lys Leu Pro Arg Thr Thr Ser Gly Lys Ile
    530                 535                 540

Gln Lys Phe Leu Leu Arg Lys Asp Ile Met Arg Arg Leu Thr Gln Asp
545                 550                 555                 560

Val Cys Glu Glu Ile Glu
                565


<210> SEQ ID NO 28
<211> LENGTH: 4
<212> TYPE: PRT
<213> ORGANISM: Unknown
<220> FEATURE:
<223> OTHER INFORMATION: Description of Unknown:
      "HDEL" sequence

<400> SEQUENCE: 28

His Asp Glu Leu
1


<210> SEQ ID NO 29
<211> LENGTH: 4
<212> TYPE: PRT
<213> ORGANISM: Unknown
<220> FEATURE:
<223> OTHER INFORMATION: Description of Unknown:
      "KDEL" motif peptide

<400> SEQUENCE: 29

Lys Asp Glu Leu
1


<210> SEQ ID NO 30
<211> LENGTH: 5
<212> TYPE: PRT
<213> ORGANISM: Cannabis sativa

<400> SEQUENCE: 30

Tyr Thr Pro Arg Lys
1               5
```

GENETICALLY MODIFIED YEAST FOR THE PRODUCTION OF CANNABIGEROLIC ACID, CANNABICHROMENIC ACID AND RELATED CANNABINOIDS

CROSS-REFERENCE TO RELATED APPLICATIONS

This application is a U.S. National Phase of International Application No. PCT/US2021/014226, filed Jan. 20, 2021, which claims priority benefit of U.S. Provisional Application No. 62/963,448, filed Jan. 20, 2020, each of which applications is herein incorporated by reference in its entirety for all purposes.

SEQUENCE LISTING PROVIDED AS ASCII FORMAT FILE

This application contains a Sequence Listing submitted electronically in ASCII format and is herein incorporated by reference in its entirety. Said ASCII copy, created on Jul. 19, 2022, is named 104059_1339921_SEQ_LST.txt and is 110,044 bytes in size.

FIELD OF THE INVENTION

The present invention relates generally to production methods, enzymes and recombinant yeast strains for the biosynthesis of cannabigerolic acid, cannabichromenic acid and related cannabinoids.

BACKGROUND OF THE INVENTION

*Cannabis sativa* varieties have been cultivated and utilized extensively throughout the world for a number of applications. Currently, cannabinoids are isolated primarily via the cultivation of large acreages of cannabis or hemp plants in agricultural operations throughout the world, with a lower, albeit clinically important level of production methodologies that involve synthetic chemical processes.

Synthetic biology, whereby individual cannabinoids are biosynthesized using isolated genetic pathways in engineered microorganisms, allows for commercial manufacture and large-scale production of naturally occurring cannabinoids and their analogs as highly pure compounds with full biological and pharmacological activities.

BRIEF SUMMARY OF ASPECTS OF THE INVENTION

This summary highlights certain aspects of the invention and does not include a description of all aspects of the invention.

In one aspect, the present disclosure provides methods and materials for producing cannabinoid compounds of interest, for example, cannabigerolic acid (CBGA) and cannabichromenic acid (CBCA) and the decarboxylated derivatives cannabigerol (CBG) and cannabichromene (CBC). In one aspect, provided herein is a method of obtaining enantiomerically pure CBC. In further aspects, provided herein are methods for producing cannabidiolic acid (CBDA), tetrahydrocannabinolic acid (THCA), and related compounds, such as the decarboxylated derivatives tetrahydrocannabinol (THC), and cannabidiol (CBD). The disclosure further provides methods and materials for producing cannabigerovarinic acid (CBGVA), cannabichromevarinic acid (CBCVA), tetrahydrocannabivarinic acid (THCVA), and cannabidiolvarinic acid (CBDVA), and the corresponding decarboxylated derivatives.

In another aspect, provided herein is a method of obtaining a high yield of CBG from chemical decarboxylation of CBGA in a reaction comprising an organic solvent, e.g., alcohol or alcohol-water mixture in the presence of a metal catalyst. In a further aspect, provided herein is a method of obtaining a high yield of CBG and additional cannabinoids using decarboxylase enzymes.

In some embodiments, olivetolic acid is fed to the yeast culture preparation that has been genetically modified to express a prenyltransferase, e.g., a polypeptide of amino acid SEQ ID NO:1; or a polypeptide that comprises the amino acid sequence of SEQ ID NO:2, and a CBCA synthetase, and is additionally modified to overexpress members of the mevalonate pathway family. Such cells produce enantiomerically pure, e.g., greater than 90%, greater than 95%, or greater than 99% pure, CBCA. The CBCA can, in turn, be decarboxylated, either enzymatically or chemically, to produce CBC. In some embodiments, chemical decarboxylation is performed as in the preceding paragraph. In further embodiments, enzymatically pure CBDA or THCA can be prepared using a yeast culture preparation modified to express CBDA synthase or THCA synthase, rather than CBCA synthase.

Olivetolic acid from any source can be used as the feedstock. In some embodiments, the olivetolic acid is produced from a genetically engineered host cell, e.g., a genetically engineered yeast cell modified to produce olivetolic acid. Such cells are described in WO 2018/209143. In some embodiments, the yeast culture preparation has been modified to produce olivetolic or divarinic acid, e.g., modified to express an acyl-CoA synthetase, e.g., that converts hexanoic acid or butanoic acid to hexanoyl-CoA or butanoyl-CoA, an olivetolic acid synthase, and an olivetolic acid cyclase.

BRIEF DESCRIPTION OF THE DRAWINGS

FIG. 1 depicts a biosynthesis scheme to generate CBGA and CBCA.

DETAILED DESCRIPTION OF THE INVENTION

Terminology

Figure 2:
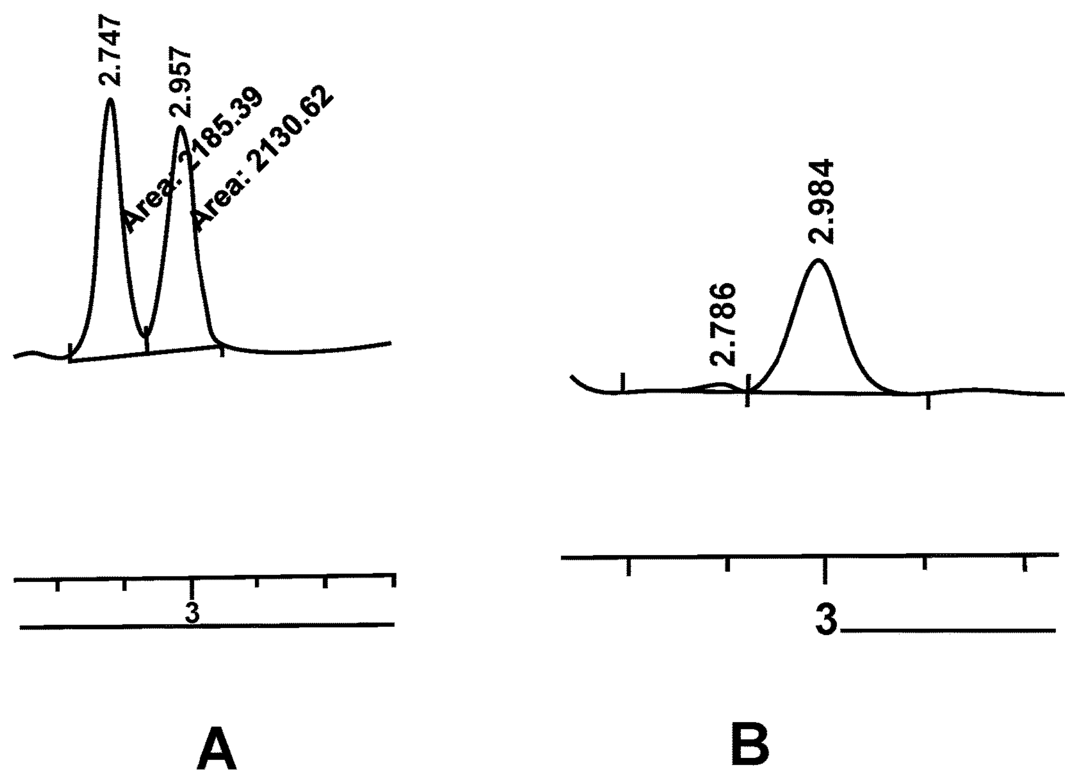
FIG. 2 depicts analytical and preparative HPLC procedures for identifying the biologically active CBC enantiomer.

Unless otherwise defined, all terms of art, notations and other scientific terminology used herein are intended to have the meanings commonly understood by those of ordinary skill in the art to which the present application pertains. In some cases, terms with commonly understood meanings are defined herein for clarity and/or for ready reference, and the inclusion of such definitions herein should not necessarily be construed to represent a substantial difference over what is generally understood in the art.

As used herein, the terms “cannabinoid,” “cannabinoid compound,” and “cannabinoid product” are used interchangeably to refer to a molecule containing a polyketide moiety, e.g., olivetolic acid or another 2-alkyl-4,6-dihydroxybenzoic acid, e.g., divarinic acid, and a terpene-derived moiety e.g., a geranyl group. Geranyl groups are derived from the diphosphate of geraniol, known as geranyl pyrophosphate, which can react with olivetolic acid type compounds to form the acidic cannabinoid cannabigerolic acid (CBGA) and CBGA analogs. CBGA can be converted to further bioactive cannabinoids both enzymatically (e.g., by decarboxylation via enzyme treatment in vivo or in vitro) and chemically (e.g., decarboxylation formed using metal catalysts and heat). Similarly, the 19-carbon precursor CBGVA and CBGVA analogs can be generated in accordance with the disclosure and converted to further bioactive cannabinoids in accordance with the methods described herein. Halogenated, e.g., fluorinated or chlorinated; deuterated; or tritiated analogs can be generated using the methods of the invention using substrates and reagents described in PCT application no. PCT/US2019/059237, which is herein incorporated by reference.

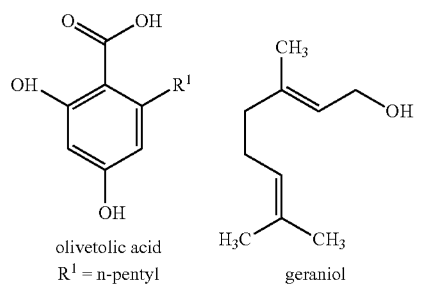

olivetolic acid
$R^1$ = n-pentyl geraniol

The term cannabinoid includes acid cannabinoids and neutral cannabinoids. The term "acidic cannabinoid" refers to a cannabinoid having a carboxylic acid moiety. The carboxylic acid moiety may be present in a protonated form (i.e., as —COOH) or in a deprotonated form (i.e., as carboxylate —COO$^-$). Examples of acidic cannabinoids include, but are not limited to, cannabigerolic acid, cannabidiolic acid, cannabichromenic acid and Δ9-tetrahydrocannabinolic acid. The term "neutral cannabinoid" refers to a cannabinoid that does not contain a carboxylic acid moiety (i.e., does not contain a moiety —COOH or —COO$^-$). Examples of neutral cannabinoids include, but are not limited to, cannabigerol, cannabidiol, cannabichromene and Δ9-tetrahydrocannabinol.

The term "2-alkyl-4,6-dihydroxybenzoic acid" refers to a compound having the structure:

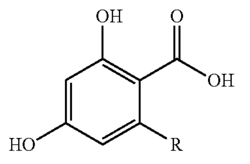

wherein R is a $C_1$-$C_{20}$ alkyl group, which in some embodiments, can be halogenated, hydroxylated, deuterated, and/or tritiated. Examples of 2-alkyl-4,6-dihydroxybenzoic acids include, but are not limited to olivetolic acid (i.e., 2-pentyl-4,6-dihydroxybenzoic acid; CAS Registry No. 491-72-5) and divarinic acid (i.e., 2-propyl-4,6-dihydroxybenzoic acid; CAS Registry No. 4707-50-0). Olivetolic acid analogs include other 2-alkyl-4,6-dihydroxybenzoic acids and substituted resorcinols including, but not limited to, 5-halomethylresorcinols, 5-haloethylresorcinols, 5-halopropylresorcinols, 5-halohexylresorcinols, 5-haloheptylresorcinols, 5-halooctylresorcinols, and 5-halononylresorcinols. Other analogs include deuterated or tritated froms.

The term "prenyl moiety" refers to a substituent containing at least one methylbutenyl group (e.g., a 2-methylbut-2-ene-1-yl group). In many instances, prenyl moieties are synthesized biochemically from isopentenyl pyrophosphate and/or isopentenyl diphosphate giving rise to terpene natural products and other compounds. Examples of prenyl moieties include, but are not limited to, prenyl, geranyl, myrcenyl, ocimenyl, farnesyl, and geranylgeranyl.

The term "geraniol" refers to (2E)-3,7-dimethyl-2,6-octadien-1-ol (CAS Registry No. 106-24-1). The term "geranylating" refers to the covalent bonding of a 3,7-dimethyl-2,6-octadien-1-yl radical to a molecule such as a 2-alkyl-4,6-hydroxybenzoic acid. Geranylation can be conducted chemically or enzymatically, as described herein.

The term "2-alkyl-4,6-dihydroxybenzoic acid" refers to a compound having the structure:

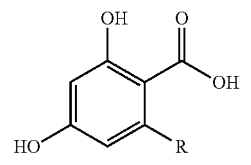

wherein R is a $C_1$-$C_{20}$ alkyl group. Examples of 2-alkyl-4,6-dihydroxybenzoic acids include, but are not limited to olivetolic acid (i.e., 2-pentyl-4,6-dihydroxybenzoic acid; CAS Registry No. 491-72-5) and divarinic acid (i.e., 2-propyl-4,6-dihydroxybenzoic acid; CAS Registry No. 4707-50-0). Olivetolic acid analogs include other 2-alkyl-4,6-dihydroxybenzoic acids and substituted resorcinols such as 5-methylresorcinol, 5-ethylresorcinol, 5-propylresorcinol, 5-hexylresorcinol, 5-heptylresorcinol, 5-octylresorcinol, and 5-nonylresorcinol.

The term "alkyl," by itself or as part of another substituent, refers to a straight or branched, saturated, aliphatic radical. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

The term "alkenyl," by itself or as part of another substituent, refers to an alkyl group, as defined herein, having one or more carbon-carbon double bonds. Examples of alkenyl groups include, but are not limited to, vinyl (i.e., ethenyl), crotyl (i.e., but-2-en-1-yl), penta-1,3-dien-1-yl, and the like. Alkenyl moieties may be further substituted, e.g., with aryl substituents (such as phenyl or hydroxyphenyl, in the case of 4-hydroxystyryl).

The terms "halogen" and "halo," by themselves or as part of another substituent, refer to a fluorine, chlorine, bromine, or iodine atom.

The term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

The term "hydroxyalkyl," by itself or as part of another substituent, refers to an alkyl group where some or all of the hydrogen atoms are replaced with hydroxyl groups (i.e., —OH groups). As for alkyl and haloalkyl groups, hydroxyalkyl groups can have any suitable number of carbon atoms, such as $C_{1-6}$.

The term "deuterated" refers to a substituent (e.g., an alkyl group) having one or more deuterium atoms (i.e., $^2$H atoms) in place of one or more hydrogen atoms.

The term "tritiated" refers to a substituent (e.g., an alkyl group) having one or more tritium atoms (i.e., $^3$H atoms) in place of one or more hydrogen atoms.

An "organic solvent" refers to a carbon-containing substance that is liquid at ambient temperature and pressure and is substantially free of water. Examples of organic solvents include, but are not limited to alcohols, toluene, methylene chloride, ethyl acetate, acetonitrile, tetrahydrofuran, benzene, chloroform, diethyl ether, dimethyl formamide, dimethyl sulfoxide, and petroleum ether.

The term "acid" refers to a substance that is capable of donating a proton (i.e., a hydrogen cation) to form a conjugate base of the acid. Examples of acids include, but are not limited to, mineral acids (e.g., hydrochloric acid, sulfuric acid, and the like), carboxylic acids (e.g., acetic acid, formic acid, and the like), and sulfonic acids (e.g., methanesulfonic acid, p-toluenesulfonic acid, and the like).

Throughout this specification and claims, the word "comprise," or variations such as "comprises" or "comprising," will be understood to imply the inclusion of a stated integer or group of integers but not the exclusion of any other integer or group of integers.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region. Alignment for purposes of determining percent amino acid sequence identity can be performed with various methods, including those using publicly available computer software such as BLAST, BLAST-2, ALIGN, Geneious, or Megalign (DNASTAR) software, among others. Examples of algorithms that are suitable for determining percent sequence identity and sequence similarity include the BLAST 2.0 algorithms, which are described in Altschul et al., Nuc. Acids Res. 25:3389-3402 (1977) and Altschul et al., J. Mol. Biol. 215:403-410 (1990). EMBOSS-Water, as can be found on the European Molecular Biology Laboratory-European Bioinformatics Institute (EMBL-EBI) may also be used for increased accuracy of alignment. The program uses a Smith-Waterman based algorithm for global pairwise sequence alignments. In the alignment options, the gap-opening penalty can be increased to prohibit the introduction of spurious gaps. For purposes of this application, EMBOSS-Water is the preferred algorithm for sequence alignments for determining percent identity.

A "conservative" substitution as used herein refers to a substitution of an amino acid such that charge, hydrophobicity, and/or size of the side group chain is maintained. Illustrative sets of amino acids that may be substituted for one another include (i) positively-charged amino acids Lys, Arg and His; (ii) negatively charged amino acids Glu and Asp; (iii) aromatic amino acids Phe, Tyr and Trp; (iv) nitrogen ring amino acids His and Trp; (v) aliphatic amino acids Gly, Ala, Val, Leu and Ile; (vi) slightly polar amino acids Met and Cys; (vii) small-side chain amino acids Ser, Thr, Asp, Asn, Gly, Ala, Glu, Gln and Pro; (viii) small hydroxyl amino acids Ser and Thr; and sulfur-containing amino acids Cys and Met. Reference to the charge of an amino acid in this paragraph refers to the charge at pH 7.0.

In specific cases, abbreviated terms are used. For example, the term "CBGA" refers to cannabigerolic acid. Likewise: "OA" refers to olivetolic acid; "CBG" refers to cannabigerol; "CBDA" refers to cannabidiolic acid; "CBD" refers to cannabidiol; "THC" refers to $\Delta^9$-tetrahydrocannabinol ($\Delta^9$-THC); "$\Delta^8$-THC" refers to $\Delta^8$-tetrahydrocannabinol; "THCA" refers to $\Delta^9$-tetrahydrocannabinolic acid ($\Delta^9$-THCA); "$\Delta^8$-THCA" refers to $\Delta^8$-tetrahydrocannabinolic acid; "CBCA" refers to cannabichromenic acid; "CBC" refers to cannabichromene; "CBGV" refers to cannabigerovarin; "CBGVA" refers to cannabigerovarinic acid; "CBCV" refers to cannabichromevarin; "CBCVA" refers to cannabichromevarinic acid; "THCV" refers to $\Delta^9$-tetrahydrocannabivarin ($\Delta^9$-THCV); "THCVA" refers to $\Delta^9$-tetrahydrocannabivarinic acid ($\Delta^9$-THCV); "GOT" refers to geranyl pyrophosphate olivetolate geranyl transferase; "YAC" refers to yeast artificial chromosome; "IRES" or "internal ribosome entry site" means a specialized sequence that directly promotes ribosome binding and mRNA translation, independent of a cap structure; and "HPLC" refers to high performance liquid chromatography.

As used herein and in the appended claims, the singular forms "a," "and," and "the" include plural referents unless the context clearly dictates otherwise.

As used herein, the terms "about" and "around" indicate a close range around a numerical value when used to modify that specific value. If "X" were the value, for example, "about X" or "around X" would indicate a value from 0.9X to 1.1X, e.g., a value from 0.95X to 1.05X, or a value from 0.98X to 1.02X, or a value from 0.99X to 1.01X. Any reference to "about X" or "around X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X, and values within this range The techniques and procedures described or referenced herein are generally well understood and commonly employed using conventional methodology by those skilled in the art, such as, for example, methodologies described in Green et al., Molecular Cloning: A Laboratory Manual 4th. edition (2012) Cold Spring Harbor Laboratory Press, Cold Spring Harbor, N. Y.; and Ausubel, et al., Current Protocols in Molecular Biology, through December 2019, John Wiley & Sons, Inc. As appropriate, procedures involving the use of commercially available kits and reagents are generally carried out in accordance with manufacturer defined protocols and/or parameters unless otherwise noted. Before the present methods, expression systems, and uses thereof are described, it is to be understood that this invention is not limited to the particular methodology, protocols, host cell strains, species or genera, constructs, and reagents described as such may, of course, vary.

Brief Overview

In one aspect, described herein is a method of producing an enantiomerically pure form of CBC, or alternatively, CBD or THC. In some embodiments, an enantiomerically pure form hast at least about 96%, 97%, 98%, 99%, or greater, active CBC enantiomer. In preferred embodiments, the method comprises coupling of geranyl-pyrophosphate to olivetolic acid in a yeast cell culture comprising yeast that are genetically modified to express members of the mevalonic acid pathway to produce CBGA. In some embodiments, CBGA is produced at a level of greater than about one gram/L. In some embodiments, the yeast cell is further engineered to convert CBGA to CBCA. CBGA or CBCA (or CBDA or THCA) can also be converted to the corresponding neutral cannabinoid, e.g., CBG or CBC (or CBD or THC), either enzymatically or chemically. In some embodiments, CBCA is decarboxylated to provide an enantiomerically pure preparation of the active form of CBC. An illustrative pathway for producing CBCA is depicted in FIG. 1. In some embodiments, the same modifications are made to produce the varinic forms of the cannabinoids using either exogenously-supplied divarinic acid or divarinic acid biosynthesized in the same strain, instead of olivetolic acid. In some embodiments, halogenated or otherwise-modified olivetolic or divarinic acids may be used.

In a further aspect, described herein is a method of decarboxylating CBGA, which method comprises incubating CBGA in a reaction, e.g., conducted at a temperature of about 20° C. to about 100° C., or about 30° C. to about 60 or 80° C., comprising an aqueous solution or an organic solvent, e.g., an alcohol or alcohol-water solution, in the presence of a metal catalyst. In some embodiments, CBGA is decarboxylated at a high efficiency in which at least 70%, or at least 80%, or at least 90% of the CBGA is converted to CBG.

Providing Olivetolic Acid or Divarinic Acid

In some embodiments, olivetolic acid is coupled to geranyl pyrophosate enzymatically by a prenyltransferase, e.g., a GOT (such as amino acid sequence SEQ ID NO:1 or a prenyltransferase polypeptide comprising the amino acid sequence of SEQ ID NO:2) to produce CBGA as analog compound. In some embodiments, the prenyltransferase comprises region In some embodiments, olivetolic acid is fed to recombinant yeast host cells, e.g., at a concentration of ranging from about 1 to about 6 mM. In other embodiments, the yeast host cells are modified to biosynthesize olivetolic acid, e.g., by engineering the cells to express an acyl-CoA synthetase, e.g., a hexanoyl-CoA synthase; a type III PKS, such as olivetolic acid synthase or an engineered variant thereof; and a cyclase enzyme, such as olivetolic acid cyclase, or an engineered variant thereof. Such enzymes are described in WO 2018/209143, which is incorporated by reference.

In some embodiments, divarinic acid is coupled to geranyl pyrophosate enzymatically by a prenyltransferase, e.g., a GOT (such as amino acid sequence SEQ ID NO:1 or a prenyltransferase polypeptide comprising the amino acid sequence of SEQ ID NO:2) to produce CBGVA. In some embodiments, the prenyltransferase comprises region 80-398 of the mature GOT3 sequence. In some embodiments, divarinic acid is fed to recombinant yeast host cells, e.g., at a concentration of ranging from about 1 to about 6 mM. In other embodiments, the yeast host cells are modified to biosynthesize divarinic acid, e.g., by engineering the cells to express an acyl-coA synthetase, e.g. a butanoyl-CoA synthase; a type III PKS, such as olivetolic acid synthase or an engineered variant thereof; and a cyclase enzyme, such as olivetolic acid cyclase, or an engineered variant thereof. Such enzymes are described in WO 2018/209143, which is incorporated by reference.

Acyl-CoA Synthase for Expression in Recombinant Host Cell

As used herein, the term "acyl-activating enzyme" refers to either a "CoA transferase" or a "CoA ligase". The term "acyl-CoA synthase" is used synonymously with "acyl-activating enzyme". Such enzymes can convert an In some embodiments, a host cell is genetically modified to express an exogenous polynucleotide that encodes a revS polypeptide from a *Streptomyces* sp. (see, e.g., Miyazawa et al, *J. Biol. Chem.* 290:26994-27001, 2015), or variant thereof, e.g., a native homolog, ortholog or non-naturally occurring variant that has acyl-CoA synthetase activity. In some embodiments, the polynucleotide encodes a polypeptide that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:10. In some embodiments, the polynucleotide encodes a RevS polypeptide that has about 75%, 80%, 85%, 90%, 95%, or greater identity to the sequence set forth in SEQ ID NO:10. In some embodiments, a non-naturally occurring variant comprises one or more modifications, e.g., substitutions such as conservative substitutions, e.g., in regions outside the AMP binding motif or catalytic site.

In some embodiments, a host cell is genetically modified to express an exogenous polynucleotide that encodes an acyl-activating enzyme from *Cannabis sativa* (CsAAE3) or variant thereof, e.g., a native homolog, ortholog or non-naturally occurring variant that has acyl-CoA synthetase activity. In some embodiments, the CsAAE3 polypeptide encoded by the polynucleotide comprises an amino acid sequence that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:11. In some embodiments, the acyl-CoA synthetase polynucleotide encodes a CsAAE3, or a homolog or non-naturally occurring thereof, comprising an amino acid sequence that has about 75%, 80%, 85%, 90%, 95%, or greater identity to the sequence set forth in SEQ ID NO:11. In some embodiments, a non-naturally occurring variant comprises one or more modifications, e.g., substitutions such as conservative substitutions, in comparison to SEQ ID NO:11, e.g., in regions outside the AMP binding motif or catalytic site.

In some embodiments, a host cell is genetically modified to express an exogenous polynucleotide that encodes an acyl activating enzyme from *Cannabis sativa* (CsAAE1) or variant thereof, e.g., a native homolog, ortholog or non-naturally occurring variant that has acyl-CoA synthetase activity. In some embodiments, the CsAAE1 polypeptide encoded by the polynucleotide comprises an amino acid sequence that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:12. In some embodiments, the acyl-CoA synthetase polynucleotide encodes a CsAAE1, or a homolog thereof, comprising an amino acid sequence that has about 75%, 80%, 85%, 90%, 95%, or greater identity to the sequence set forth in SEQ ID NO:12. In some embodiments, the CsAAE1 polynucleotide encodes a polypeptide from which the transmembrane domain is deleted. In some embodiments, a non-naturally occurring variant comprises one or more modifications, e.g., substitutions such as conservative substitutions, in comparison to SEQ ID NO:12, e.g., in regions outside the AMP binding motif or catalytic site.

In some embodiments, e.g., for the production of olivetolic acid or divarinic acid, a host cell is genetically modified to express an exogenous polynucleotide that encodes a butyryl CoA-transferase from *Roseburia hominis*(see, e.g., Charrier, et al, *Microbiology* 152:179-185, 2006), or variant thereof, e.g., a native homolog, ortholog or non-naturally occurring variant that has butyryl CoA transferase activity. In some embodiments, the polynucleotide encodes a polypeptide that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:20. In some embodiments, the polynucleotide encodes a RevS polypeptide that has about 75%, 80%, 85%, 90%, 95%, or greater identity to the sequence set forth in SEQ ID NO:20. In some embodiments, a non-naturally occurring variant comprises one or more modifications, e.g., substitutions such as conservative substitutions, e.g., in regions outside the AMP binding motif or catalytic site Additional examples of organisms that express CoA-transferases for use in the methods can be found in the Comprehensive Enzyme Information System (BRENDA) under Enzyme Commission numbers EC 2.8.3.8 (acetate CoA-transferase), EC 2.8.3.1 (propionate CoA-transferase), and EC 2.8.3.9 (butyrate-acetoacetate CoA-transferase). These organisms include, but are not limited to: *Anaerostipes* species and strains (e.g., *A. caccae; A. caccae* DSM 14662), *Anaerobutyricum* species and strains (e.g., *A. hallii; A. hallii* M72/1), *Anaerotignum* species and strains (e.g., *A. propionicum*), *Aspergillus* species and strains (e.g., *A. nidulans*), *Butyrivibrio* species and strains (e.g., *B. fibrisolvens; B. fibrisolvens* 16/4), *Clostridium* species and strains (e.g., *C. kluyveri*), *Coprococcus* species and strains (e.g., *Coprococcus* sp. L2-50), *Cupriavidus* species (e.g., *C. necator* H16), *Escherichia* species and strains (e.g., *E. coli* K-12); *Eubacterium* species and strains (e.g., *E. rectale, E. rectale* DSM 17629), *Faecalibacterium* species and strains (e.g., *F. prausnitzii; F. prausnitzii* A2-165; *F. prausnitzii* L2-6; *F. prausnitzii* M21/2), Megasphaera species and strains (e.g., *M. elsdenii*), *Propionibacterium* strains and species (e.g., *P. freudenreichii*), and *Roseburia* species and strains (e.g., *R. hominis, R. intestinalis; R. intestinalis* L1-82; *R. inulinivorans; R. inulinivorans* A2-194; and *Roseburia* sp. A2-181).

Non-limiting examples of specific CoA-transferases are listed below.

| Organism | CoA-transferase | UniProt Accession No. |
|---|---|---|
| *A. caccae* DSM 14662 | Butyryl-CoA: acetate CoA-transferase | B0MC58 |
| *A. hallii* | Butyryl-CoA: acetate CoA-transferase | D2WEY8 |
| *A. propionicum* | Propionate CoA-transferase | Q9L3F7 |
| *A. nidulans* | Propionate CoA-transferase | |
| *B. fibrisolvens* | Butyryl-CoA: acetate CoA-transferase | D2WEY7 |
| *C. kluyveri* | Propionate CoA-transferase | |
| *C. necator* | Propionate CoA-transferase | |
| *C. necator* H16 | Acetate CoA-transferase YdiF | Q0K874 |
| *E. coli* K-12 | Acetyl-CoA: acetoacetate CoA-transferase subunit beta (AtoA) | P76459 |
| *E. coli* K-12 | Acetyl-CoA: acetoacetate-CoA transferase subunit alpha (AtoD) | P76458 |
| *E. rectale* DSM 17629 | Butyryl-CoA: acetate CoA-transferase | D2WEY1 |
| *F. prausnitzii* | Butyryl-CoA: acetate CoA-transferase | D2WEZ2 |
| *F. prausnitzii* M21/2 | Butyryl-CoA: acetate CoA-transferase | A8SFP6 |
| *F. prausnitzii* A2-165 | Butyryl-CoA: acetate CoA-transferase | C7H5K4 |
| *M. elsdenii* | Propionate CoA-transferase | |
| *P. freudenreichii* | Propionate CoA-transferase | |
| *R. hominis* DSM 16839 | Butyryl-CoA: acetate CoA-transferase | G2SYC0 |
| *R. intestinalis* L1-82 | Butyryl-CoA: acetate CoA-transferase | C7GB37 |
| *R. inulinivorans* | Butyryl-CoA: acetate CoA-transferase | D2WEY6 |

In some embodiments, the CoA transferase comprises an *E. coli* acetyl-CoA:acetoacetyl-CoA transferase polypeptide sequence, e.g., SEQ ID NO:21 and SEQ ID NO:22. In some embodiments, the CoA transferase comprises a *C. necator* H16 propionate CoA-transferase polypeptide sequence, e.g., as set forth in SEQ ID NO:23. In some embodiments, the CoA transferase comprises an amino acid sequence that has at least 60% or greater identity (e.g., at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, identity) to the sequence set forth in SEQ ID NO:21, 22, or 23. In some embodiments, the CoA transferase has at least 70%, 75%, 80%, 85%, 90%, 95%, or greater identity to the sequence set forth in SEQ ID NO:21, 22, or 23. In some embodiments, the CoA transferase comprises the amino acid sequence of SEQ ID NO:21, 22, or 23.

In some embodiments, an acyl CoA ligase is employed to convert at aliphatic carboxylic acid to an acyl CoA thoester. In some embodiments, the CoA ligase is selected from the group consisting of *Mycobacterium avium* mig medium chain acyl-CoA ligase, *A. thaliana* AT4g05160 coumarate acyl-CoA ligase, *S. cerevisiae* FAA2 medium chain acyl-CoA ligase, and *E. coli* FADK acyl-CoA ligase.

In some embodiments, the CoA ligase comprises an *M. avium* mig medium chain acyl-CoA ligase polypeptide sequence, e.g., as set forth in SEQ ID NO:24. In some embodiments, the CoA ligase comprises an *A. thaliana* AT4g05160 coumarate acyl-CoA ligase polypeptide sequence, e.g., as set forth in SEQ ID NO:25. In some embodiments, the CoA ligase comprises a *S. cerevisiae* FAA2 medium chain acyl-CoA ligase polypeptide sequence, e.g., as set forth in SEQ ID NO:26. In some embodiments, the CoA ligase comprises an *E. coli* FADK acyl-CoA ligase polypeptide sequence, e.g., as set forth in SEQ ID NO:27. In some embodiments, the CoA ligase comprises an amino acid sequence that has at least 60% or greater identity (e.g., at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, identity) to the sequence set forth in any one of SEQ ID NO:24, 25, 26, or 27. In some embodiments, the CoA ligase has at least 70%, 75%, 80%, 85%, 90%, 95%, or greater identity to the sequence set forth in SEQ ID NO:24, 25, 26, or 27. In some embodiments, the CoA ligase comprises the amino acid sequence of SEQ ID NO:24, 25, 26, or 7. In some embodiments, In the some embodiments, the aliphatic carboxylic acid is a $C_{1-5}$ carboxylic acid.

In the some embodiments, the aliphatic carboxylic acid is a $C_{6-20}$ carboxylic acid.

In the some embodiments, the aliphatic carboxylic acid comprises a carbon-carbon double bond, a hydroxy group, a halogen, deuterium, tritium, or a combination thereof.

Olivetolic Acid Synthase for Expression in Recombinant Host Cell

In some embodiments, a host cell is additionally genetically modified to express an exogenous polynucleotide that encodes olivetolic acid synthase or variant thereof e.g., a native homolog or ortholog, or a non-naturally occurring variant that has polyketide synthase activity. Olivetolic acid synthase (Taura et al. *FEBS Letters* 583:2061-2066, 2009), also referred to as 3, 5, 7,-trioxododecanoyl-CoA synthase, UniProtKB-B1Q2B6, is a type III PKS that that catalyzes the condensation of acyl-CoAs with three molecules of malonyl-CoA to form a 3,5,7-trioxoalkanoyl-CoA tetraketide as shown below:

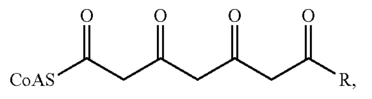

wherein "CoA" is coenzyme A and "R" is an alkyl group. For example, when hexanoic acid is used as the starting feed for cannabinoid production, the hexanoyl-CoA formed by the acyl-CoA synthetase, e.g., revS or CsAAE3, as described above is condensed with three molecules of malonyl-CoA to form 3,5,7-trioxododecanoyl-CoA (i.e., "R" is an n-pentyl group).

In some embodiments, an olivetolic acid synthase polynucleotide encodes a polypeptide that comprises an amino acid sequence that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:13. In some embodiments, the olivetolic acid synthase polynucleotide encodes a type III PKS comprising an amino acid sequence that has about 75%, 80%, 85%, 90%, 95%, or greater identity to the sequence set forth in SEQ ID NO:13.

2-Alkyl-4,6-Dihydroxybenzoic Acid Cyclase Expressed in Recombinant Host Cells

A host cell in accordance with the invention may be further modified to express an exogenous polynucleotide that encodes a 2-alkyl-4,6-dihydroxybenzoic acid cyclase (e.g., olivetolic acid cyclase). In some embodiments, the 2-alkyl-4,6-dihydroxybenzoic acid cyclase is a dimeric $\alpha+\beta$ barrel (DABB) protein domain that resembles DABB-type polyketide cyclases from *Streptomyces*. Olivetolic acid cyclase is described, for example, by Gagne et al. (*Proc. Nat. Acad. Sci. USA* 109 (31): 12811-12816; 2012).

In some embodiments, the polynucleotide encoding the 2-alkyl-4,6-dihydroxybenzoic acid cyclase encodes a polypeptide that has at least 70% identity or at least 75%, identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:14, 15, or 16. In some embodiments, the polypeptide has about 75%, 80%, 85%, 90%, 95%, or greater identity to the sequence set forth in SEQ ID NO:14, 15, or 16.

In some embodiments, a chemically-synthesized thioester is used as a starting material instead of employing an acyl-CoA synthase to enzymatically produce the thioester from a carboxylic acid.

Exogenous prenyl species, such as geraniol, can also be supplied to the host cells during culture and production of the prenylated compounds. Alternatively, the host cells can be cultured in media containing high levels of prenyl precursors, e.g., prenol, isoprenol, geraniol, and the like. In procedures including multiple precursor feeding (MPF), 5-carbon prenol and isoprenol can be enzymatically converted to the monophosphate level (i.e., to dimethylallyl monophosphate and isopentenyl monophosphate) and then to the diphosphate level (i.e., to dimethylallyl pyrophosphate and isopentenyl pyrophosphate) prior to coupling to form the 10-carbon geranyl pyrophosphate.

In some embodiments, the starting carboxylic acid is hexanoic acid or butanoic acid, giving rise to precursors for the eventual production of cannabigerolic or cannabinogerovarinic acid-type molecules, and their decarboxylated, and otherwise chemically transformed, derivatives. In some embodiments, the starting carboxylic acids are analog compounds that are fluorinated or chlorinated at various positions; or deuterated or tritiated at various positions.

Production of CBGA, CBCA, CBDA, THCA

In typical embodiments, a recombinant yeast host cell provided herein may be genetically modified to express a prenyltransferase that catalyzes coupling of geranyl-pyrophosphate to olivetolic acid or divarinic acid (or an analog of said acid) to form a cannabinoid compound, e.g., CBGA or CBGVA (or CBGA or CBGVA analog compound). Examples of prenyltransferases include geranylpyrophosphate:olivetolate geranyltransferase (GOT; EC 2.5.1.102) as described by Fellermeier & Zenk (FEBS Letters 427:283-285; 1998), as well as *Cannabis sativa* prenyltransferases described in WO 2018/200888 and WO 2019/071000. *Streptomyces* prenyltransferases including NphB, as described by Kumano et al. (Bioorg Med Chem. 16(17): 8117-8126; 2008), can also be used in accordance with the invention. In some embodiments, the prenyltransferase is fnq26, i.e., flaviolin linalyltransferase from *Streptomyces cinnamonensis.*

In some embodiments, the yeast host cells are modified to express a GOT for catalyzing the coupling of geranyl-pyrophosphate to olivetolic acid (or an olivetolic acid analog compound, e.g., a fluorinated or chlorinated analog). In some embodiments, the amino acid sequence of the GOT is SEQ ID NO:1. In some embodiments, the GOT polypeptide comprises an amino acid sequence of SEQ ID NO:2.1

In some embodiments, divarinic acid (or an analog compound of divarinic acid, e.g., a fluorinated or chlorinated analog) is used as the intermediate compound to which geranyl-pyrophosphate is coupled to produce CBGVA (or the corresponding analog).

In some embodiments, yeast host strains are further modified to convert CBGA, CBGVA, or an analog of CBGA or CBGVA to a second acidic cannabinoid. In some such embodiments, the expression system is on the same vector or on a separate vector, or is integrated into the host cell genome. In other embodiments, the expression system for the conversion activity encodes one of the *C. sativa* enzymes CBCA synthase, THCA synthase, or CBDA synthase. In some embodiments, the synthase is a homolog from hops, e.g., a CBDA synthase homolog from hops. In some embodiments, the expression system encode a hops CBDA homolog that has at least 70% identity or at least 75%, identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:17, 19, or 19. In some embodiments, the polypeptide has about 75%, 80%, 85%, 90%, 95%, or greater identity to the sequence set forth in SEQ ID NO:17, 18, or 19.

CBCAS can be expressed as a fusion protein lacking its own signal peptide, or can be expressed with its own signal peptide or a heterologous signal peptide or hydrophobic domain at its amino terminus.

In other embodiments, an HDEL or KDEL endoplasmic reticulum-retention sequence is fused to the expressed GOT, CBCAS or GOT/CBCAS mutant enzymes. In some embodiments, the GOT and CBCAS constructs may be modified to introduce targeted mutations, or random mutations in the expressed enzymes, such that the expressed enzyme has favorable properties for cannabinoid acid production.

In some embodiments, the CBCAS signal peptide is the endogenous signal peptide used by the cannabis plant, or it may be replaced by a yeast or a heterologous targeting sequence such as the yeast alpha-factor pre- or pre-pro-sequence, the yeast proteinase A pre- or pre-pro-sequence, or sequences derived from the *Cannabis* GOT (which is also referred to here an "CsPT4") enzyme such as for example, the hydrophobic region(s) starting around amino acid 80 of the mature GOT3 enzyme. Other preferred signal peptides include the *S. cerevisiae* pdi1 signal sequence or the berberine bridge-associated easE signal sequence from *Aspergillus japonica*. The CBCAS gene construct may be modified by changing the sequence to remove N-linked glycosylation sites in the protein. All permutations and combinations of glycosylation site modifications may be examined for increased or optimal activities. In other embodiments, a fusion protein, such as hSOD may be incorporated into the constructs to be expressed. CBCA, THCA or CBDA synthase gene constructs may be similarly modified.

Illustrative CBCAS polypeptide sequences are provided in SEQ ID NOS:3-9. In some embodiments, the polynucleotide encoding the CBCAS encodes a polypeptide that has at least 70% identity, or at least 75% identity, or at least about 80% or greater identity (e.g., about 81%, 82%, 83%, 84%, 85%, 86%, 87%, 88%, 89%, 90%, 91%, 92%, 93%, 94%, 95%, 96%, 97%, 98%, 99%, or 100% identity) to the regions of the CBCAS polypeptide of any one of SEQ ID NOS:3-9 that excludes the signal sequence or ER-retention sequence. In some embodiments, the polypeptide has about 75%, 80%, 85%, 90%, 95%, or greater identity to the sequence set forth in any one of SEQ ID NOS:3-9.

In some embodiments, an acidic cannabinoid, e.g., CBGA or CBCA, may be decarboxylated to form a neutral cannabinoid compound, e.g., CBG or CBC, using a decarboxylase, e.g., *Aspergillus nidulans* orsB decarboxylase, or a homolog or engineered variant thereof. Alternatively, an acidic cannabinoid can be decarboxylated by maintaining the acidic cannabinoid at an elevated temperature (e.g., around 40° C., 50° C., or 100° C.) using a metal catalyst. Thus, in a further aspect, provided herein are chemical and biochemical methods for the decarboxylation of cannabinoid acids such as THCA, CBDA, CBGA, CBCA, THCVA, CBDVA, CBGVA and CBCVA, as well as additional cannabinoid acid analogs. In some embodiments, CBGA is converted to CBG using an organic solvent and metal catalyst.

In some embodiments, decarboxylation is performed using metal catalysts and heat and may utilize whole centrifuged yeast cells that are expressing and retain the cannabinoid acid or, alternatively, may use as substrates cannabinoid acids extracted from the yeast cells using an extraction reagent that comprises an organic solvent, water/aqueous buffer, or a mixture thereof. In preferred embodiments, such organic solvents comprise an alcohol such as ethanol, propanol, isopropanol or butanol. Metal catalysts include any metal catalyst suitable for decarboxylating acidic cannabinoids. In some embodiments, the metal catalyst contains zinc, magnesium, molybdenum, nickel, copper, platinum, palladium, or iron. The catalyst may further include one or more metal ligands including, but not limited to, hydroxide (—OH), amines (—$NR_3$, wherein each R group is independently H, optionally substituted alkyl, or optionally substituted aryl), thiols (—SR, wherein R is optionally substituted alkyl or optionally substituted aryl), halides (e.g., $F^-$, $Cl^-$, $Br^-$, and $I^-$), organic acids (e.g., acetoacetic acids, hydroxamic acids, and the like), chelators (e.g., aminopolycarboxylates such as ethylenediaminetetraacetic acid (EDTA) and nitrilotriacetic acid (NTA), and heterocycles (e.g., phenanthrolines, bipyridines, and the like). In some embodiments, the metal catalyst is a metal salt. In some embodiments, the metal salt is a zinc salt. In some embodiments, the metal salt is a palladium or platinum salt. The metal catalyst may be in solution, in solid form, e.g., as zinc dust or zinc oxide, or may be in the form of a metal-doped zeolite catalyst, such as HZSM-5 loaded with a metal such as zinc, magnesium, molybdenum, nickel, copper, platinum, palladium, or iron. Similarly, zeolite catalysts may be used either alone or in the presence of the aforementioned metal salt solutions or in non-aqueous organic solvents, including anhydrous organic solvents. The decarboxylation reaction is typically conducted at temperatures ranging from around 25° C. to about 100° C. and a pH ranging from about 3 to about 12 for a period of time ranging from a few minutes to several hours, e.g., 2 to 6 hours, or longer, e.g., up to 12, 18, 24, 36, or 48 hours. Various decarboxylation methods are also described, e.g., in US Pat. Application Publication No. 20180016216 and Wang et al., *Cannabis and Cannabinoid Res. Volume* 1.1, 2016).

Any suitable organic solvent can be used in the methods of the invention. Suitable solvents include, but are not limited to, an alcohol, e.g., methanol, ethanol, propanol, isopropanol, butanol and the like. In some embodiments the organic solvent is hexane or heptane. In some embodiments the organic solvent is hexane or heptane. In some embodiments, the solvent is toluene, methylene chloride, ethyl acetate, acetonitrile, tetrahydrofuran, benzene, ethylbenzene, xylenes (i.e., m-xylene, o-xylene, p-xylene, or any combination thereof), chloroform, diethyl ether, dimethyl formamide, dimethyl sulfoxide, petroleum ether, and mixtures thereof. Aqueous organic solvent mixtures (i.e., a mixture of water and a water-miscible organic solvent such as tetrahydrofuran or dimethyl formamide) can also be employed. In general, the ratio of the solvent to the 2-alkyl-4,6-dihydroxybenzoic acid ranges from about 1:1 to about 1000:1 by weight. The ratio of the solvent to the 2-alkyl-4,6-dihydroxybenzoic acid can be, for example, about 100:1 by weight, or about 10:1 by weight, or about 5:1 weight. In certain embodiments, the 2-alkyl-4,6-dihydroxybenzoic acid is present in a yeast mixture (e.g., dried yeast cells, or a wet yeast cell pellet collected from culture). In some such embodiments, the reaction mixture comprises the host cell (e.g., dried yeast cells). The ratio of solvent to yeast mixture (e.g., dried yeast cells) can range from about 1:1 to about 1000:1 by weight. The ratio of the solvent to the yeast mixture can be, for example, about 100:1 by weight, or about 10:1 by weight, or about 5:1 by weight, or about 2:1 by weight.

Enzymatic methods for the decarboxylation of cannabinoid acids include the use of recombinant aromatic decarboxylase enzymes such as described by Payer et al., Advanced Synth. & Catal. 361:2402-2420, 2019. In some embodiments, a PatG enzyme from *Aspergillus clavatus*, an orsB orsellinic acid decarboxylase from *Aspergillus nidulans* or a 3,4-dihydroxybenzoic acid decarboxylase from *Enterobacter cloacae* may be employed. In some embodiments, the decarboxylase is a wild-type enzyme. In other embodiments, such enzymes are variants that have been engineered through amino acid mutations to have greater decarboxylase activities or to have other optimal parameters, such as modified thermal or pH optima. In some embodiments, the decarboxylase contacts the target cannabinoid acid as a lysate from the engineered microorganism or as whole cells in the presence of zymolyase. In some embodiments, decarboxylase enzymes are expressed by genetically modified host cells, e.g., a *S. cerevisiae* yeast strain.

In still other embodiments, conversion of a first intermediate cannabinoid to a second cannabinoid through the action of a wild type or a mutant cannabinoid or cannabinoid acid synthase, either within the same engineered host cell or through co-culturing with two or more recombinant host cell strains, e.g., yeast strains.

As explained above, in some embodiments, host cells, e.g., yeast strains, transformed or genomically integrated with polynucleotide segments, plasmids or vectors containing each of the above genes are transformed together with another expression system for the conversion of CBGA or a CBGA analog to a second acidic cannabinoid. In some such embodiments, the expression system is on the same vector or on a separate vector, or is integrated into the host cell genome. In other embodiments, the expression system for the conversion activity encodes one of the *C. sativa* enzymes CBCA synthase, THCA synthase, or CBDA synthase.

For downstream processing at scale, producing yeast cells may be centrifuged and the media-localized cannabinoid acid may be separated and purified to give a highly purified cannabinoid acid, such as by ion-exchange chromatography, hydrophobic or chelation chromatography, or by selective extraction procedures. Similarly, the yeast-associated cannabinoid acid may be purified using such techniques or may be decarboxylated prior to the use of such techniques.

Cannabinoid compounds of interest and cannabinoid compound intermediates are produced using an expression system as described herein. Such compounds include, without limitation, CBGA, CBG, CBCA, CBC, THCA, THC, CBDA, and CBD as well as analog compounds including, e.g., halogenated or deuterated or tritiated compounds. In some embodiments, each step of a metabolic pathway that produces the cannabinoid compound of interests occurs in a modified recombinant cell described herein. In other embodiments, at least one step of the metabolic pathway occurs in a modified recombinant cell described herein, and at least one step of the metabolic pathway occurs extracellularly, e.g., in a host cell extract or within a co-cultured modified recombinant cell. The compounds produced at each step of the metabolic pathway may be referred to as "intermediates" or "intermediate compounds" or "compound intermediates".

Host Cells

In some embodiments, the methods of the invention are performed using a yeast, or a filamentous fungus host cell such as an *Aspergillus* host cell. Genera of yeast that can be employed as host cells include, but are not limited to, cells of *Saccharomyces, Schizosaccharomyces, Candida, Hansenula, Pichia, Kluyveromyces, Yarrowia* and Phaffia. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus, Kluyveromyces lactis*, Phaffia rhodozyma and, *Yarrowia lipolytica*. Filamentous fungal genera that can be employed as host cells include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Illustrative species of filamentous fungal species include *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride.*

In some embodiments, the host cell is selected from the group consisting of *Saccharomyces cerevisiae, Kluyveromyces lactis, Kluyveromyces marxianus, Pichia pastoris, Yarrowia hpolytica, Hansenula polymorpha* and *Aspergillus.*

In the above embodiments, the genes may be encoded by chemically synthesized genes, with yeast codon optimization, that encode a wild-type or mutant enzyme from *C. sativa, Arabidopsis thaliana, Pseudomonas* spp., or Dictyostelium spp.

In one aspect, the invention provides vectors and modified recombinant host cells for the expression of polypeptides having the enzymatic activities as described herein. In some embodiments, vectors of the invention include a selection gene, a yeast 2-micron sequence, and a polynucleotide encoding a polypeptide, where the polynucleotide is operably linked to an alcohol dehydrogenase 2 promoter. In some of these embodiments, the polynucleotide includes one or more yeast-preferred codons substituted for naturally occurring codons. In some embodiments, the vector does not propagate and/or amplify in a bacterial host cell. In some embodiments, the selection gene is a URA3, HIS3, TRP1, or a LEU2 gene.

As detailed above, in some embodiments, the polypeptide comprises a geranyl-pyrophosphate-olivetolic acid geranyltransferase (EC 2.5.1.102, GOT) or a functionally active portion thereof. In some of the latter embodiments the GOT may be truncated at the amino- and/or the carboxy-termini. In some of the embodiments the GOT may be expressed directly using a suitably placed methionine initiation codon and a suitably placed stop codon. In yet further embodiments, the GOT may be expressed as a fusion protein with partners that confer enhanced expression of the active GOT. Suitable fusion partners include human superoxide dismutase (hSOD) or any other superoxide dismutase, yeast maltose binding protein (MBP), human or yeast ubiquitin (Ub), human catalase (hCAT), *S. cerevisiae* catalase T (CTT1), *S. cerevisiae* peroxisomal catalase A (CTA1), transferrin, human serum albumin (HSA), or any other SOD, catalase, or fusion partner. Additional fusion partners include human galectin, *E. coli* MBP, yeast prepro alpha factor and GB1.

In some embodiments, the yeast cell is $cir^0$. In some of these embodiments, the yeast cell is protease-deficient and/or is strain BJ2168 (ATCC 208287). In some embodiments, the yeast strain is a modified industrial ethanol producing strain and/or is strain "Super alcohol active dry yeast" (Angel Yeast Co., Ltd. Yichang, Hubei 443003, P.R.China). Such strains are modified by curing to $cir^0$ and have selectable marker mutations (e.g. URA3, HIS3, TRP1 and LEU2) in the genome that are well-known to those skilled in the art.

In some embodiments the final concentration in the yeast culture of the desired cannabinoid-producing enzyme is at least about 0.1 gram per liter, 1 gram per liter, 2 grams per liter, or 4 grams per liter. In some embodiments, the desired polypeptide is a fusion polypeptide. In some embodiments of the methods of the invention, the nucleotide sequence encoding the desired polypeptide is further operably linked to an alcohol dehydrogenase 2 terminator. In some embodiments, dissolved oxygen is continually present in the culture medium at a concentration of greater than or equal to about 50%. In some embodiments, the polynucleotide further includes a polynucleotide encoding a yeast URA3 polypeptide. In some embodiments, the yeast cell is of the genus *Saccharomyces*, such as the strain BJ2168[$cir^0$] TRP revertant. In some embodiments, the glucose provides about 100% of the oxidizable substrate for respiration. In one embodiment of the methods of the invention, the polynucleotide further encodes a signal sequence or a prepro-secretory sequence operably linked to the yeast alcohol dehydrogenase-2 promoter.

The invention concerns compositions and methods for production of polypeptides in yeast transformed with a plasmid, where the plasmid to be used is an episomal expression plasmid and includes a yeast promoter and terminator, a selection gene, the gene for the polypeptide desired to be produced, optionally containing one or more yeast-preferred codons that replace naturally-occurring native codons, and an origin of replication such as the 2-micron DNA sequence of endogenous yeast plasmids. Preferably, the yeast promoter is a regulated promoter, e.g., the ADH2 promoter; generally the terminator will match the promoter, e.g., the ADH2 terminator, but need not be matching. In other embodiments, terminators such as, but not limited to, those of the *S. cerevisiae* CYC, GPD, PYK, PGK, or ADH1 genes may be used. In some embodiments the plasmid may also contain a yeast pre- or prepro-signal (leader) sequence, if it is desired that the polypeptide be secreted extracellularly or targeted to a yeast vacuole or membrane; however, for many polypeptides, e.g., GOT or fusion proteins of GOT with a leader sequence is not used as it is desirable that the polypeptide be maintained intracellularly in order for it to be available to catalyze the conversion of soluble substrates. In some embodiments, the plasmid may also be unable to propagate and/or amplify in a bacterial host cell, e.g., because it is substantially free of bacterial sequences required for propagation and/or amplification in a bacterial cell. The plasmid is introduced into an appropriate yeast strain; in some embodiments this is a circle-zero)($cir^0$, protease-deficient yeast strain; in some embodiments the original strain contains endogenous yeast plasmid and is subsequently cured of endogenous plasmids before transformation. The transformed yeast may be selected by growth on a medium appropriate for the selectable marker of the plasmid, for example, a leucine- or uracil-deficient medium. In productive fermentation, if a regulated promoter is used, e.g., the ADH2 promoter, the promoter can be regulated to repress recombinant polypeptide synthesis. In embodiments in which the ADH2 promoter is used, production of the protein under control of the promoter is repressed in high glucose levels, providing for continuous expression under glucose-limited growth conditions. The fed batch fermentation process described here allows for regulation of the amount of glucose provided to the yeast culture and thus, control of protein expression.

Plasmids of the invention contain an origin of replication. In one embodiment, a 2-micron DNA sequence required for autonomous replication in yeast is utilized, allowing the plasmid to be maintained as an extrachromosomal element capable of stable maintenance in a host yeast. In some embodiments, the full-length yeast 2-micron sequence may be used, although functional fragments are contemplated. The full-length yeast 2-micron sequence may be cloned from, e.g., an *S. cerevisiae* genomic DNA preparation containing 2-micron DNA; see, e.g., Barr et al. (eds), Chapters 9 and 10.

In further embodiments, strains that produce CBGA are transformed with plasmids that express a cannabichromenic acid synthase (CBCAS) as described above. In embodiments in which CBCA, THCA or CBDA are produced, strains are transformed with plasmids that express the corresponding synthase. The synthase can similarly be expressed as a fusion protein or with a native or heterologous signal peptide, as desired, and may be modified to give targeted mutations, or random mutations in the expressed enzymes, such that the enzyme has favorable properties for cannabinoid acid production.

Promoters used for driving transcription of genes in *S. cerevisiae* and other yeasts are well known in the art and include DNA elements that are regulated by glucose concentration in the growth media, such as the alcohol dehydrogenase-2 (ADH2) promoter. Other regulated promoters or inducible promoters, such as those that drive expression of the GAL1, MET25 and CUP1 genes, are used when conditional expression is required. GAL1 and CUP1 are induced by galactose and copper, respectively, whereas MET25 is induced by the absence of methionine.

In some embodiments, one or more of the exogenous polynucleotides are operably linked to a glucose-regulated promoter. In some embodiments, expression of one or more of the exogenous polynucleotides is driven by an alcohol dehydrogenase-2 promoter.

Other promoters drive strong transcription in a constitutive manner. Such promoters include, without limitation, the control elements for highly expressed yeast glycolytic enzymes, such as glyceraldehyde-3-phosphate dehydrogenase (GPD), phosphoglycerate kinase (PGK), pyruvate kinase (PYK), triose phosphate isomerase (TPI) and alcohol dehydrogenase-1 (ADH1). Another strong constitutive promoter that may be used is that from the *S. cerevisiae* transcription elongation factor EF-1 alpha gene (TEF1) (Partow et al., Yeast. 2010, (11):955-64).

In other embodiments, the host cells can increase cannabinoid production by increasing precursor pools and the like. Heterologous natural or chemically synthesized genes for enzymes such as malonyl-CoA synthase, acetyl-CoA carboxylase, acetyl-CoA synthases-1 and -2, gene products in the mevalonate pathway, e.g., acetoacetyl-CoA thiolase, HMG-CoA synthase, HMG-CoA reductase, mevalonate kinase, phosphomevalonate kinase, mevalonate pyrophosphate decarboxylase, isopentenyl diphosphate isomerase, mutant farnesyl-pyrophosphate synthase (ERG20; Zhao et al., 2016) from *Saccharomyces* or other eukaryotic or prokaryotic species may be introduced on high-level expression plasmid vectors or through genomic integration using methods well known to those skilled in the art. Thus, in some embodiments, an enzyme may occur naturally in a cell, but the cell is engineered to produce higher levels than wild-type cells, whereas in some embodiments, the enzyme does not occur naturally in the host cell, but is heterologous to the host cell, e.g., from another species. Such methods may involve CRISPR Cas-9 technology, yeast artificial chromosomes (YACs) or the use of retrotransposons. Alternatively, if natural to the host organism, such genes may be upregulated by genetic element integration methods known to those skilled in the art.

In yet other aspects, similar engineering may be employed to reduce the production of natural products, e.g., ethanol that utilize carbon sources that lead to reduced utilization of that carbon source for cannabinoid production. Such genes may be completely "knocked out" of the genome by deletion, or may be reduced in activity through reduction of promoter strength, mutation, or the like. Such genes include those for the enzymes ADH1 and/or ADH6. Other gene "knockouts" include genes involved in the ergosterol pathway, such as ERG9, wild-type ERG20, and the two most prominent aromatic decarboxylase genes of yeast, PAD1 and FDC1.

In certain aspects of the invention, yeast strains that overexpress integrated genes or modified genes of the mevalonate pathway are utilized to biosynthesize geranyl-diphosphate for attachment to the aromatic polyketide precursors, olivetolic acid, divarinic acid and analogs, to produce cannabinoid acids. In one exemplar embodiment, strain Y385 coupled with plasmid pBM308L was used for CBGA production. Strain Y385 has the following integrations using *S. cerevisiae*-based sequences unless otherwise noted:

At the HO locus: pTEF1-IDI1; pADH2-tHMGR; pADH2-ERG13; pTEF2-ERG20 (F96W, N127W); at the ROX1 locus: pTEF2-ERG8; pADH2-ERG10; pADH2-tHMGR; pTDH3-MVD1; at the YFLO41W locus: pMLS1-ERG20 (F96W, N127W); pICL1-ERG13; pADH2 (S. para)-tHMGR; pFBA1-MatB (S. co); at the REI1 locus: pMLS1-ERG12; pFBA1-MVD1; pADH2-mvaE (E. fa); pICL1-mvaS (E. fa); pTEF1-ERG8; at the PRB1 locus: pURA3-URA3; pTEF1-ADR1; pFBA1-PDC (Z. mo).

In some embodiments, the host cells, e.g., yeast cells that produce CBGA, or a halogenated, deuterated, or tritated analog thereof, is engineered to overexpress enzymes of the mevalonic acid pathway. Such enzymes, includes, for example, Erg10, Erg13, HMGR, Erg 12, Erg8, Mvd1, Idi1, and Erg 20. See, e.g., U.S. Pat. No. 6,689,593, which is incorporated by reference.

Further embodiments include genes for accessory enzymes aimed at assisting in the production of the final product cannabinoids. One such enzyme, catalase, is able to neutralize hydrogen peroxide produced by certain enzymes involved in the oxido-cyclization of CBGA and analogs, such as cannabidiolic acid synthase (Taura et al., 2007), $\Delta^9$-tetrahydrocannabinolic acid synthase (Sirikantaramas et al., 2004) and cannabichromenic acid synthase (Morimoto et al., 1998).

In further embodiments, the engineered host cells contain up-regulated or down-regulated endogenous or heterologous genes to optimize, for example, the precursor pools for cannabinoid biosynthesis. Additional, further heterologous gene products may be expressed to give "accessory" functions within the cell. For example, overexpressed catalase may be expressed in order to neutralize hydrogen peroxide formed in the oxido-cyclization step to important acidic cannabinoids such as CBDA, $\Delta^9$-THCA and CBCA. "Accessory" genes and their expressed products may be provided through integration into the yeast genome through techniques well known in the art, or may be expressed from plasmids (also known as yeast expression vectors), yeast artificial chromosomes (YACs) or yeast transposons.

In some embodiments, host cells, e.g., yeast strains, transformed or genomically integrated with plasmids or vectors containing each of the above genes are transformed together with another expression system for the conversion of CBGA or a CBGA analog to a second acidic cannabinoid, as further explained below. In some such embodiments, the expression system is on the same vector or on a separate vector, or is integrated into the host cell genome.

The cannabinoid-producing engineered cells of the invention may be made by transforming a host cell, either through genomic integration or using episomal plasmids (also referred to as expression vectors, or simply vectors) with at least one nucleotide sequence encoding enzymes involved in the engineered metabolic pathways. As used herein the term "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In some embodiments, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., either increase or decrease the level of expression). Accordingly, described are nucleic sequences encoding the enzymes involved in the engineered metabolic pathways. In some embodiments, a metabolically engineered cell may express one or more polypeptides having an enzymatic activity necessary to perform the steps described below. In some embodiments, the nucleotide sequences are synthesized and codon-optimized for expression in yeast according to methods described in U.S. Pat. No. 7,561,972.

For example a particular cell may comprise one, two, three, four, five or more than five nucleic acid sequences, each one encoding the polypeptide(s) necessary to produce a cannabinoid compound, or cannabinoid compound intermediate described herein. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequences, DNA libraries, de novo synthesis, or excision of genomic segments. The sequences obtained from such sources may then be modified using standard molecular biology and/or recombinant DNA technology to produce nucleic sequences having desired modifications. Exemplary methods for modification of nucleic acid sequences include, for example, site directed mutagenesis, PCR mutagenesis, deletion, insertion, substitution, swapping portions of the sequence using restriction enzymes, optionally in combination with ligation, homologous recombination, site specific recombination or various combination thereof. In other embodiments, the nucleic acid sequences may be a synthetic nucleic acid sequence. Synthetic polynucleotide sequences may be produced using a variety of methods described in U.S. Pat. No. 7,323,320, as well as U.S. Pat. Appl. Pub. Nos. 2006/0160138 and 2007/0269870. Methods of transformation of yeast cells are well known in the art.

Fermentation Conditions

Cannabinoid production according to the methods provided herein generally includes the culturing of host cells (e.g., yeast or filamentous fungi) that have been engineered to contain the expression systems described above. In some embodiments, the carbon sources for yeast growth are sugars such as glucose, sucrose, xylose, or other sustainable feedstock sugars such as those derived from cellulosic sources, for example. In other embodiments, the carbon sources used may be methanol, glycerol, ethanol or acetate. In some embodiments, feedstock compositions are refined by experimentation to provide for optimal yeast growth and final cannabinoid production levels, as measured using analytical techniques such as HPLC. In such embodiments, methods include utilization of glucose/ethanol or glucose/acetate mixtures wherein the molar ratio of glucose to the 2-carbon source (ethanol or acetate) is between the ranges of 50/50, 60/40, 80/20, or 90/10. Feeding may be optimized to both induce glucose-regulated promoters and to maximize the production of acetyl-CoA and malonyl-CoA precursors in the production strain.

Fermentation methods may be adapted to a particular yeast strain due to differences in their carbon utilization pathway or mode of expression control. For example, a *Saccharomyces* yeast fermentation may require a single glucose feed, complex nitrogen source (e.g., casein hydrolysates), and multiple vitamin supplementation. This is in contrast to the methylotrophic yeast *Pichia pastoris* which may require glycerol, methanol, and trace mineral feeds, but only simple ammonium (nitrogen) salts, for optimal growth and expression. See, e.g., Elliott et al. J. Protein Chem. (1990) 9:95 104, U.S. Pat. No. 5,324,639 and Fieschko et al. Biotechnol. Bioeng. (1987) 29:1113 1121. Culture media may contain components such as yeast extract, peptone, and the like. The microorganisms can be cultured in conventional fermentation modes, which include, but are not limited to, batch, fed-batch, and continuous flow.

In some embodiments, the rate of glucose addition to the fermenter is controlled such that the rate of glucose addition is approximately equal to the rate of glucose consumption by the yeast; under such conditions, the amount of glucose or ethanol does not accumulate appreciably. The rate of glucose addition in such instances can depend on factors including, but not limited to, the particular yeast strain, the fermentation temperature, and the physical dimensions of the fermentation apparatus.

Using multiple precursor feeding (MPF) procedures (see, WO 2018/209143, which is incorporated by reference), in batch mode, the precursors olivetolic acid (or an olivetolic acid analog such as another 2-alkyl-4,6-dihydroxybenzoic acid, e.g., divarinic acid), prenol, isoprenol or geraniol may be present in concentrations of between 0.1 and 50 grams/L (e.g., between 1 and 10 g/L). In fed-batch mode, the precursors may be fed slowly into the fermentation over between 2 and 20 hours, such that a final addition of between 1 and 100 grams/L (e.g., between 1 and 10 grams/L, or between 10 and 100 grams/L) of each requisite precursor occurs.

Similarly, carboxylic acid starting materials such as hexanoic acid, butanoic acid, pentanoic acid, and the like may be present in concentrations of between 0.1 and 50 grams/L (e.g., between 1 and 10 g/L). In fed-batch mode, the carboxylic acid may be fed slowly into the fermentation over between 2 and 20 hours, such that a final addition of between 1 and 100 grams/L (e.g., between 1 and 10 grams/L, or between 10 and 100 grams/L) of the carboxylic acid occurs.

Culture conditions such as expression time, temperature, and pH can be controlled so as to afford target cannabinoid intermediates (e.g., olivetolic acid or divarinic acid) and/or target cannabinoid products (e.g., CBGA, CBGVA) in high yield. Host cells are generally cultured in the presence of starting materials, such as olivetolic acid, hexanoic acid, prenol, isoprenol, or the like, for periods of time ranging from a few hours to a day or longer (e.g., 24 hours, 30 hours, 36 hours, or 48 hours) at temperatures ranging from about 20° C. to about 40° C. depending on the particular host cells employed. For example, *S. cerevisiae* may be cultured at 25-32° C. for 24-40 hours (e.g., 30 hours). The pH of culture medium can be maintained at a particular level via the addition of acids, bases, and/or buffering agents. In certain embodiments, culturing yeast at a pH of 6 or higher can reduce the production of unwanted side products such as olivetol. In some embodiments, the pH of the yeast culture ranges from about 6 to about 8. In some embodiments, the pH of the yeast culture is about 6.5. In some embodiments, the pH of the yeast culture is about 7. In some embodiments, the pH of the yeast culture is about 8.

In some embodiments, a recombinant yeast cell is genetically modified such that it produces, when cultured in vivo in a suitable precursor-containing media as described above, the cannabinoid or cannabinoid acid product of interest or an intermediate at a level of at least about 0.1 g/L, at least about 0.5 g/L, at least about 0.75 g/L, at least about 1 g/L, at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 7 g/L, at least about 8 g/L, at least about 9 g/L, or at least 10 g/L. In some embodiments, a recombinant yeast cell is genetically modified such that it produces, when cultured in vivo in a suitable medium, the cannabinoid product of interest or an intermediate at a level of at least about 20 g/L, at least about 30 g/L, at least about 50 g/L, or at least about 80 g/L.

Cannabinoid production may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermenter, or other vessel for cell growth or incubation. Biologically produced products of interest may be isolated from the fermentation medium or cell extract using methods known in the art. For example, solids or cell debris may be removed by centrifugation or filtration. Products of interest may be isolated, for example, by distillation, liquid-liquid extraction, membrane evaporation, adsorption, or other methods.

The invention illustratively described herein suitably may be practiced in the absence of any element or elements, limitation or limitations that are not specifically disclosed herein. Thus, for example, in each instance herein any of the terms "comprising", "consisting essentially of" and "consisting of" may be replaced with either of the other two terms. Thus, for example, some embodiments may encompass a host cell "comprising" a number of components, other embodiments would encompass a host cell "consisting essentially of" the same components, and still other embodiments would encompass a host cell "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art. All patents, patent applications, and literature references cited in the present specification are hereby incorporated by reference in their entirety.

EXAMPLES

Example 1. Construction of Plasmids Expressing a Truncated GOT3 Gene and Production of CBGA This example describes the construction and use of the plasmid pBM308L. This plasmid is an episomal expression plasmid that was constructed using ADH2 promoter and terminator sequences flanking a gene for human superoxide dismutase (hSOD) fused in-frame to a GOT3 mini-gene that encodes amino acids 80-398 of the CsPT4 sequence, the LEU2 gene and 2-micron sequences cloned de novo by PCR from yeast genomic DNA. The CsP *C. sativa* CsPT4 gene was chemically synthesized by GenScript Corporation using yeast-preferred codons.

The 2-micron sequence in this plasmid contains the origin for autonomous replication in yeast. The LEU2 gene facilitates selection of transformed cells and retention of the plasmid during growth in leucine-deficient medium. The expression of GOT3 is controlled by the glucose-regulated ADH2 promoter. Growth of cells under glucose-limiting conditions induces continuous expression of the hSOD/GOT3 fusion protein and expression is inhibited when cells are grown in excess glucose. The ADH2 terminator is required to terminate transcription of the rAAT gene in yeast.

The plasmid pBM308L was transformed into strain Y385. The Y385 strain is a derivative of "Super alcohol active dry yeast" (Angel Yeast Co., Ltd. Yichang, Hubei 443003, P.R.China). In addition to introduced selectable markers (URA3 and LEU2), the strain also includes the entire mevalonate pathway for the biosynthesis of geranyl-pyrophosphate, and ADR1 transcription factor and pyruvate decarboxylase (PDC) genes.

An overnight culture was grown in 3 mL of Leu-minimal media. 500 ul of the overnight culture was then inoculated into 5 mL of YPD (2% D, 10 mM riboflavin and 50 uM pantothenic acid). After an additional 24 h, where the optical density reached 15, 2.69 mg olivetolic acid (OA) (150 ul of 80 mM OA (75% EtOH)) was fed into the culture. Additional OA was added at 44 h and 81 h for a total of 6.2 mg OA (350 ul of 80 mM).

Figure 3:
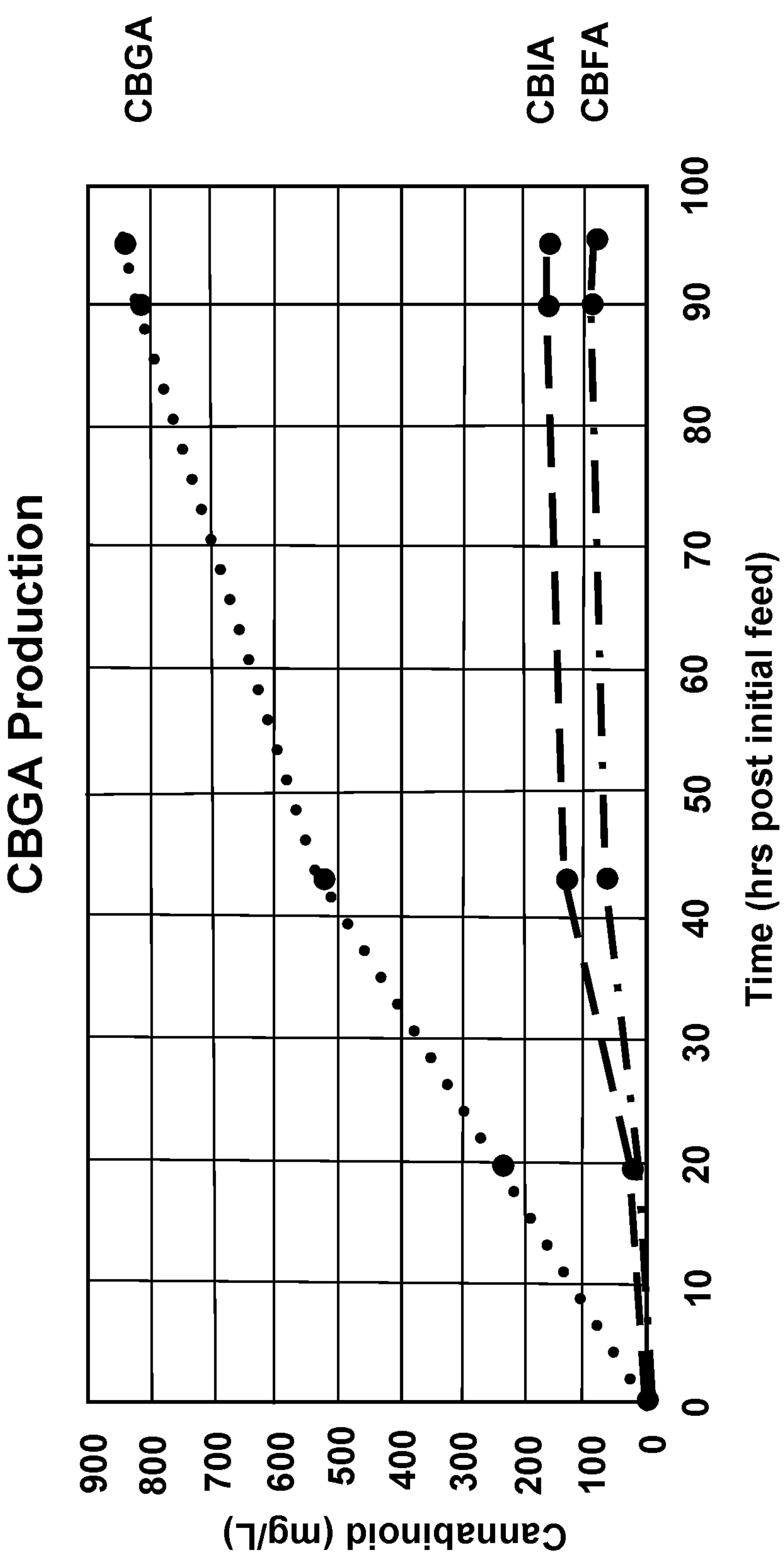
FIG. 3 depicts the fermentation results for production of CBGA for conversion to CBCA using CBCA synthase.

CBGA, CBFA, and CBIA production was recorded over time (FIG. 3). At 90 hours post-inoculation, the flask was placed at 4° C. and sampled. CBGA was measured at 820 mg/L. The final $OD_{600}$ was 21.2. A whole flask extraction was performed and CBGA was measured at 843 mg/L. In addition, lower levels of the minor products CBFA and CBIA were detected. CBFA and CBIA are longer and shorter side-chain homologs of CBGA in which the geranyl group is replaced by a farnesyl or an isopentenyl group respectively (Pollastro et al., *J. Natural Products* 74:2019-2022, 2011).

Example 2. Extraction and Purification of CBGA from Recombinant *S. cerevisiae* Cells Cell cultures prepared as described in Example 1 were centrifuged and extracted with 50% isopropanol/water. The yeast media supernatants were collected and subjected to ion-exchange chromatography, followed by further downstream processing steps to give >98% pure CBGA. The isopropanol/water extracts were converted to CBG as described in Example 6.

Example 3. Production of Enantiomerically Pure CBCA in *S. cerevisiae*

The yeast cell strain described in Example 1 was co-transformed with the plasmid pBM703U, which contains a synthetic DNA sequence encoding, with yeast-preferred codons, the full-length CBCA synthase gene (encoding the CBCAS sequence of SEQ ID NO:9) under the control of the ADH2 promoter. Cells were grown as described in Example 1, and whole culture extracts (50% isopropanol/media) were analyzed by HPLC. Under normal reversed-phase HPLC conditions, CBCA was found to be synthesized in good yields. When the CBCA was decarboxylated and analyzed using a chiral (amylose-based) HPLC column, it was found, surprisingly, that the only enantiomer biosynthesized was the active CBC molecule. Previous work had shown that the CBC isolated from the cannabis plant was composed of both enantiomers of CBC. In contrast, FIG. 2 shows that the CBCAS enzyme, when expressed in yeast gives CBCA at an enantiomeric purity of greater than 96% and most likely close to 100% enantiomeric purity, when allowing for the known epimerization under the conditions used for decarboxylation of CBCA to CBC in this experiment.

Example 4. Decarboxylation of CBGA in CBGA-Containing Yeast Cells in the Presence of Metal Salts Decarboxylation of CBGA from centrifuged yeast as described in Example 1 was accomplished at small scale by centrifugation of 1 mL of total yeast cell culture, followed by resuspension in a 10 mM, 50 mM or 100 mM metal salt solution, with or without the addition of zeolite (10 mg). Suspensions, using 50 mM zinc sulfate and 5 mM sodium hydroxide, were heated at 70° C. overnight and yields of CBG, as determined by HPLC were found to be greater than 90%.

Example 5. Decarboxylation of CBCA in CBCA-Containing Yeast Cells in the Presence of Metal Salts Enantiomerically pure CBC is similarly prepared, as in Example 4, using the cells described in Example 3. Reactions proceed in a similar fashion to CBGA decarboxylation, except that CBCA decarboxylation is both faster and higher yielding.

Example 6. Increased Yields of CBGA by Providing Ethanol as an Extra Carbon Source In an experiment similar to Example 1, ethanol was added as an extra carbon source (as a 1.5 mM bolus of olivetolic acid in 50% ethanol). Following growth overnight, six such additions were made at 12 h intervals. The media also included Tween 20 (1%). In this experiment, an increased yield, relative to the yield in Example 1, of 1.40 g/L CBGA was observed by extraction and HPLC analysis.

Example 7. Fusion of an Truncated GOT3 to SOD Increases Yields

A small-scale, non-glucose fed, shake-flask experiment was used to compare an hSOD-GOT3 fusion construct containing truncated GOT3 (80-398) fusion construct directly with the same truncated enzyme lacking the hSOD fusion partner. The results showed that there was a pronounced increase in the level of CBGA using the hSOD fusion construct (346.5 mg/L versus 73.2 mg/L).

Example 8. Additional GOT3 Truncations

The GOT3 enzyme is known to contain several putative transmembrane domains. In this experiment, additional GOT3 constructs that have alternative truncations, relative to GOT3 (80-398) were evaluated. In this set of experiments, plasmid 308L (Example 1) was replaced with plasmids pBM309L, pBM316L, and pBM318L, which contain GOT3 genes as follows: a longer N-terminal deletion, pBM309L, encoding GOT3 amino acids 113-398; pBM316L, encoding GOT3 amino acids 80-269 (pBM316L); and pBM318L, encoding GOT3 amino acids 80-339. Barely detectable or undetectable CBGA expression levels were observed by HPLC analysis.

Example 9. Decarboxylation of Cannabinoid Acids CBGA and CBCA Following Extraction from Yeast Cells Decarboxylation in isopropanol/water was also shown to proceed in a similar fashion when the cannabinoid acids were separated from the yeast cells by vortexing in a 50% isopropanol/water mixture, centrifugation, and treatment of the clear solution with metals or metal salts as described above.

Example 10. Production of CBGVA

An overnight culture of yeast cells expressing the *C. sativa* olivetolic acid PKS system (the *C. sativa* tetraketide synthase (TKS) and an engineered C. *Sativa* cyclase) and transformed with a DNA construct for the production of butanoyl-CoA using the *Roseburia hominis* butanoylCoA transferase, or transformed with constructs encoding CsAAE3 or revS, was grown in 3 mL of Leu-, Ura-minimal media. 300 ul of the overnight culture was then inoculated into 3 mL culture tubes of YPD (2% D, 10 mM riboflavin and 50 uM pantothenic acid). The cells were grown overnight at 30 C and 250 rpm. In the morning and evening, a 2 mM butanoic acid bolus was fed from a 1M ethanol solution and the culture grown overnight. The next morning and evening 2 mM butanoic acid was fed from a 0.3M butanoic acid stock diluted in ethanol, and the culture grown overnight. 2 mM butanoic acid feeds (0.3M stock in ethanol) were repeated for a third day. The culture was extracted as above and divarinic acid (dVA) and divarinol (dVL) production were measured by HPLC at the 72 h time point. The yield of dVA was 628 mg/L and that of dVL, 93 mg/L. When this experiment was repeated in a 2 L (2 liter) glucose-fed fermenter, the yield of dVA was increased to around 1.4 g/L. This yield was higher than yields obtained using revS or CsAAE3 constructs.

Example 11. Production of CBGVA Using GOT3 Truncation (80-398)

Strain Y371, transformed with plasmid 308L, expressing GOT3 (amino acids 80-398) was grown as an overnight culture in 3 mL of Leu-minimal media. 500 ul of the overnight culture was then inoculated into 5 mL flasks of YPD (2% D, 10 mM riboflavin, 50 uM pantothenic acid, 1% Tween20). The cells were grown overnight at 30° C. and 250 rpm. In the morning and evening, 0.5 mM crude dVA extract dissolved in EtOH was added (1 mM dVA total). The cells were grown for an additional 48-72 hrs and CBGVA production was measured by HPLC. CBGVA was obtained in an amount of 148 mg/L.

Example 12. Production of THCA, CBCA, CBDA, THCVA, CBCVA, CBDVA

Overnight cultures of yeast strains expressing the appropriate cannabinoid acid synthases were grown in 3 mL of the appropriate dropout minimal media. 500 ul of the overnight culture was then inoculated into 5 mL flasks of YPD (2% D, 10 mM riboflavin, 50 uM pantothenic acid, 1% Tween 20). The cells were grown at 15 C for 72 hrs, 250 rpm. The cells were then transferred to 30 C and fed 2 mM OA or dVA dissolved in 50% EtOH. The cells were grown for an additional 48-72 hrs at 30 C, the cultures were extracted and cannabinoid acid production was measured by HPLC. Yields of the cannabinoid acids from these small-scale shake-flask experiments were 301 mg/L (THCA), 309 mg/L (CBCA), 163 mg/L (CBDA), 84 mg/L (THCVA), 56 mg/L (CBCVA), and 16 mg/L (CBDVA).

Example 13. Production of Olivetolic Acid Analogs and Olivetol Analogs in Recombinant Yeast Yeast cells expressing the *C. sativa* olivetolic acid PKS system were transformed with DNA constructs for various CoA transferases or CoA ligases and cultured as described in Example 10, feeding with a range of fatty acid substrates in addition to butanoic acid. As shown in the following table, *R. hominis* butyryl-CoA:acetate CoA-transferase was found to be particular useful in the production of a variety of olivetolic acid analogs and olivetol analogs.

TABLE 1

Production of olivetolic acid, olivetol and their analogs, including divarinic acid and divarinol using selected acyl-CoA transferases and ligases.

| | CsAAE3 [1] | | revS [2] | | Mig [3] | | FAA2 [4] | | A.th [5] | | FADK [6] | | R.ho [7] | | PCT [8] | |
|---|---|---|---|---|---|---|---|---|---|---|---|---|---|---|---|---|
| Fatty acid substrate | OA [a] analog | OL [b] analog | OA analog | OL analog | OA analog | OL analog | OA analog | OL analog | OA analog | OL analog | OA analog | OL analog | OA analog | OL analog | OA analog | OL analog |
| Octanoic acid | 4 | 9 | 5 | 8 | 4 | 4 | 2 | 1 | 4 | 5 | 5 | 9 | 5 | 11 | 4 | 9 |
| Heptanoic acid | 34 | 34 | 73 | 43 | 8 | 3 | 55 | 59 | 41 | 45 | 60 | 55 | 58 | 50 | 53 | 49 |
| Hexanoic acid | 133 | 72 | 119 | 66 | 10 | 2 | 231 | 102 | 215 | 102 | 265 | 114 | 393 | 136 | n/d | n/d |
| 6-Fluoro-hexanoic acid | 118 | 80 | 92 | 53 | 13 | 0 | 144 | 85 | 100 | 64 | 79 | 93 | n/d | n/d | n'd | n/d |
| 5-Chloro=pentanoic acid | 55 | 16 | 60 | 6 | 9 | 0 | 92 | 24 | 58 | 12 | 24 | 9 | 153 | 35 | n/d | n/d |
| Butanoic acid | 25 | 3 | 11 | 0 | 13 | 3 | 58 | 9 | 42 | 5 | 12 | 0 | 314 | 51 | n/d | n/d |
| 4-Fluoro-butanoic acid | 53 | 19 | 0 | 0 | 29 | 8 | 7 | 1 | 32 | 9 | 0 | 0 | 228 | 70 | 154 | 45 |
| 3-Methyl=butanoic acid | 0 | 0 | 3 | 0 | 6 | 0 | 0 | 0 | 13 | 0 | 0 | 0 | 287 | 26 | n/d | n/d |
| 2-Methyl-propanoic acid | 0 | 0 | 0 | 0 | 24 | 36 | 0 | 0 | 0 | 0 | 0 | 0 | 156 | 224 | 114 | 168 |

[1] *C. sativa* CsAAE3

[2] *Streptomyces* sp. SN-593 revS medium chain fatty acid acyl-CoA ligase

[3] *M. avium* mig medium chain Acyl-CoA ligase

[4] *S. cerevisiae* FAA2 medium chain acyl-CoA ligase

[5] *A. thaliana* AT4g05160 coumarate acyl-CoA ligase

[6] *E. coli* FADK acyl-CoA ligase

[7] *R. hominis* butyryl-CoA: acetate CoA-transferase

[8] *C. necator* propionate-CoA transferase

[a] OA analog = olivetolic acid analog yield (mg/L)

[b] OL analog = olivetol analog yield (mg/L)

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

ILLUSTRATIVE SEQUENCES

SEQ ID NO: 1 GOT truncated sequence; amino acids 80-398 of CsPT4 GOT protein; the M at position 1 of SEQ ID NO: 1 is the starting methionine encoded by a polynucleotide construct that expresses the polypeptide, position 80 of amino acids 80-398 of the mature GQT sequence corresponds to position 2 residue "S" of SEQ ID NO: 1.

MSDQIEGSPHHESDNSIATKILNFGHTCWKLQRPYVVKGMISIACGLFGRELFNNRHL
FSWGLMWKAFFALVPILSFNFFAAIMNQIYDVDIDRINKPDLPLVSGEMSIETAWILSII
VALTGLIVTIKLKSAPLFVFIYIFGIFAGFAYSVPPIRWKQYPFTNFLITISSHVGLAFTS
YSATTSALGLPFVWRPAFSFIIAFMTVMGMTIAFAKDISDIEGDAKYGVSTVATKLGA
RNMTFVVSGVLLLNYLVSISIGIIWPQVFKSNIMILSHAILAFCLIFQTRELALANYASA
PSRQFFEFIWLLYYAEYFVYVFI

SEQ ID NO: 2 hSQD-GOT3 amino acid sequence fused to region 80-398 of GOT protein sequence. The hSQD sequence is underlined.

MATKAVCVLKGDGPVQGIINFEQKESNGPVKVWGSIKGLTEGLHGFHVHEFGDNTA
GCTSAGPHFNPLSRKHGGPKDEERHVGDLGNVTADKDGVADVSIEDSVISLSGDHCII
GRTLVVHEKADDLGKGGNEESTKTGNAGSRLACGVIGIAQPRSDQIEGSPHHESDNSI
ATKILNFGHTCWKLQRPYVVKGMISIACGLFGRELFNNRHLFSWGLMWKAFFALVPI
LSFNFFAAIMNQIYDVDIDRINKPDLPLVSGEMSIETAWILSIIVALTGLIVTIKLKSAPL
FVFIYIFGIFAGFAYSVPPIRWKQYPFTNFLITISSHVGLAFTSYSATTSALGLPFVWRP
AFSFIIAFMTVMGMTIAFAKDISDIEGDAKYGVSTVATKLGARNMTFVVSGVLLLNY
LVSISIGIIWPQVFKSNIMILSHAILAFCLIFQTRELALANYASAPSRQFFEFIWLLYYAE
YFVYVFI

SEQ ID NO: 3 Prepro alpha-CBCAS Protein Sequence; the prepro sequence is underlined. The start of the mature polypeptide sequence is shown in bold.

MRFPSIFTTVLFAASSALAAPVNTTTEDETAQIPAEAVIGYLDLEGDFDVAVLPFSNST
NNGLLFINTTIASIAAKEEGVSLDKRANPQENFLKCFSEYIPNNPANPKFIYTQHDQLY
MSVLNSTIQNLRFTSDTTPKPLVIVTPSNVSHIQASILCSKKVGLQIRTRSGGHDAEGL
SYISQVPFAIVDLRNMHTVKVDIHSQTAWVEAGATLGEVYYWINEMNENFSFPGGY
CPTVGVGGHFSGGGYGALMRNYGLAADNIIDAHLVNVDGKVLDRKSMGEDLFWAI
RGGGGENFGIIAAWKIKLVVVPSKATIFSVKKNMEIHGLVKLFNKWQNIAYKYDKDL
MLTTHFRTRNITDNHGKNKTTVHGYFSSIFLGGVDSLVDLMNKSFPELGIKKTDCKE
LSWIDTTIFYSGVVNYNTANFKKEILLDRSAGKKTAFSIKLDYVKKLIPETAMVKILE
KLYEEEVGVGMYVLYPYGGIMDEISESAIPFPHRAGIMYELWYTATWEKQEDNEKHI
NWVRSVYNFTTPYVSQNPRLAYLNYRDLDLGKTNPESPNNYTQARIWGEKYFGKNF
NRLVKVKTKADPNNFFRNEQSIPPLPPRHH

SEQ ID NO: 4 Prepro alpha-CBCAS-HDEL (Protein sequence). The prepro sequence and HDEL sequences are underlined.

MRFPSIFTTVLFAASSALAAPVNTTTEDETAQIPAEAVIGYLDLEGDFDVAVLPFSNST
NNGLLFINTTIASIAAKEEGVSLDKRANPQENFLKCFSEYIPNNPANPKFIYTQHDQLY
MSVLNSTIQNLRFTSDTTPKPLVIVTPSNVSHIQASILCSKKVGLQIRTRSGGHDAEGL
SYISQVPFAIVDLRNMHTVKVDIHSQTAWVEAGATLGEVYYWINEMNENFSFPGGY
CPTVGVGGHFSGGGYGALMRNYGLAADNIIDAHLVNVDGKVLDRKSMGEDLFWAI
RGGGGENFGIIAAWKIKLVVVPSKATIFSVKKNMEIHGLVKLFNKWQNIAYKYDKDL
MLTTHFRTRNITDNHGKNKTTVHGYFSSIFLGGVDSLVDLMNKSFPELGIKKTDCKE
LSWIDTTIFYSGVVNYNTANFKKEILLDRSAGKKTAFSIKLDYVKKLIPETAMVKILE
KLYEEEVGVGMYVLYPYGGIMDEISESAIPFPHRAGIMYELWYTATWEKQEDNEKHI
NWVRSVYNFTTPYVSQNPRLAYLNYRDLDLGKTNPESPNNYTQARIWGEKYFGKNF
NRLVKVKTKADNNFFRNEQSIPPLPPRHHHDEL

SEQ ID NO: 5 Pdi1- CBCAS Protein sequence The *Saccharomyces cerevisiae* Pdi1 signal sequence is underlined MKFSAGAVLSWSSLLLASSVFAQQANPQENFLKCFSEYIPNNPANPKFIYTQHDQLY
MSVLNSTIQNLRFTSDTTPKPLVIVTPSNVSHIQASILCSKKVGLQIRTRSGGHDAEGL
SYISQVPFAIVDLRNMHTVKVDIHSQTAWVEAGATLGEVYYWINEMNENFSFPGGY
CPTVGVGGHFSGGGYGALMRNYGLAADNIIDAHLVNVDGKVLDRKSMGEDLFWAI
RGGGGENFGIIAAWKIKLVVVPSKATIFSVKKNMEIHGLVKLFNKWQNIAYKYDKDL
MLTTHFRTRNITDNHGKNKTTVHGYFSSIFLGGVDSLVDLMNKSFPELGIKKTDCKE
LSWIDTTIFYSGVVNYNTANFKKEILLDRSAGKKTAFSIKLDYVKKLIPETAMVKILE
KLYEEEVGVGMYVLYPYGGIMDEISESAIPFPHRAGIMYELWYTATWEKQEDNEKHI
NWVRSVYNFTTPYVSQNPRLAYLNYRDLDLGKTNPESPNNYTQARIWGEKYFGKNF
NRLVKVKTKADPNNFFRNEQSIPPLPPRHH SEQ ID NO: 6 EasE-CBCAS Protein sequence. The berberine bridge-associated easE signal sequence from *Aspergillus japonica* is underlined MGQSRGILGGVRQLILVILVGAYLSRLSAVDANPQENFLKCFSEYIPNNPANPKFIYT
QHDQLYMSVLNSTIQNLRFTSDTTPKPLVIVTPSNVSHIQASILCSKKVGLQIRTRSGG
HDAEGLSYISQVPFAIVDLRNMHTVKVDIHSQTAWVEAGATLGEVYYWINEMNENF
SFPGGYCPTVGVGGHFSGGGYGALMRNYGLAADNIIDAHLVNVDGKVLDRKSMGE
DLFWAIRGGGGENFGIIAAWKIKLVVVPSKATIFSVKKNMEIHGLVKLFNKWQNIAY
KYDKDLMLTTHFRTRNITDNHGKNKTTVHGYFSSIFLGGVDSLVDLMNKSFPELGIK -continued

| ILLUSTRATIVE SEQUENCES |
|---|

KTDCKELSWIDTTIFYSGVVNYNTANFKKEILLDRSAGKKTAFSIKLDYVKKLIPETA
MVKILEKLYEEEVGVGMYVLYPYGGIMDEISESAIPFPHRAGIMYELWYTATWEKQE
DNEKHINWVRSVYNFTTPYVSQNPRLAYLNYRDLDLGKTNPESPNNYTQARIWGEK
YFGKNFNRLVKVKTKADPNNFFRNEQSIPPLPPRHH

SEQ ID NO: 7 Prepro alpha-CBCAS (amino acids 87 to 545 of SEQ ID NO: 9) protein sequence. The prepro sequence is underlined.
MRFPSIFTTVLFAASSALAAPVNTTTEDETAQIPAEAVIGYLDLEGDFDVAVLPFSNST
NNGLLFINTTIASIAAKEEGVSLDKRPSNVSHIQASILCSKKVGLQIRTRSGGHDAEGL
SYISQVPFAIVDLRNMHTVKVDIHSQTAWVEAGATLGEVYYWINEMNENFSFPGGY
CPTVGVGGHFSGGGYGALMRNYGLAADNIIDAHLVNVDGKVLDRKSMGEDLFWAI
RGGGGENFGIIAAWKIKLVVVPSKATIFSVKKNMEIHGLVKLFNKWQNIAYKYDKDL
MLTTHFRTRNITDNHGKNKTTVHGYFSSIFLGGVDSLVDLMNKSFPELGIKKTDCKE
LSWIDTTIFYSGVVNYNTANFKKEILLDRSAGKKTAFSIKLDYVKKLIPETAMVKILE
KLYEEEVGVGMYVLYPYGGIMDEISESAIPFPHRAGIMYELWYTATWEKQEDNEKHI
NWVRSVYNFTTPYVSQNPRLAYLNYRDLDLGKTNPESPNNYTQARIWGEKYFGKNF
NRLVKVKTKADPNNFFRNEQSIPPLPPRHH*

SEQ ID NO: 8 CBCAS; amino acids 87-545 (of SEQ ID NO: 9) with methionine initiation codon
MPSNVSHIQASILCSKKVGLQIRTRSGGHDAEGLSYISQVPFAIVDLRNMHTVKVDIH
SQTAWVEAGATLGEVYYWINEMNENFSFPGGYCPTVGVGGHFSGGGYGALMRNY
GLAADNIIDAHLVNVDGKVLDRKSMGEDLFWAIRGGGGENFGIIAAWKIKLVVVPS
KATIFSVKKNMEIHGLVKLFNKWQNIAYKYDKDLMLTTHFRTRNITDNHGKNKTTV
HGYFSSIFLGGVDSLVDLMNKSFPELGIKKTDCKELSWIDTTIFYSGVVNYNTANFKK
EILLDRSAGKKTAFSIKLDYVKKLIPETAMVKILEKLYEEEVGVGMYVLYPYGGIMD
EISESAIPFPHRAGIMYELWYTATWEKQEDNEKHINWVRSVYNFTTPYVSQNPRLAY
LNYRDLDLGKTNPESPNNYTQARIWGEKYFGKNFNRLVKVKTKADPNNFFRNEQSIP
PLPPRHH*

SEQ ID NO: 9 CBCAS synthase full-length amino acid sequence
MNCSTFSFWFVCKIIFFFLSFNIQISIANPQENFLKCFSEYIPNNPANPKFIYTQHDQLY
MSVLNSTIQNLRFTSDTTPKPLVIVTPSNVSHIQASILCSKKVGLQIRTRSGGHDAEGL
SYISQVPFAIVDLRNMHTVKVDIHSQTAWVEAGATLGEVYYWINEMNENFSFPGGY
CPTVGVGGHFSGGGYGALMRNYGLAADNIIDAHLVNVDGKVLDRKSMGEDLFWAI
RGGGGENFGIIAAWKIKLVVVPSKATIFSVKKNMEIHGLVKLFNKWQNIAYKYDKDL
MLTTHFRTRNITDNHGKNKTTVHGYFSSIFLGGVDSLVDLMNKSFPELGIKKTDCKE
LSWIDTTIFYSGVVNYNTANFKKEILLDRSAGKKTAFSIKLDYVKKLIPETAMVKILE
KLYEEEVGVGMYVLYPYGGIMDEISESAIPFPHRAGIMYELWYTATWEKQEDNEKHI
NWVRSVYNFTTPYVSQNPRLAYLNYRDLDLGKTNPESPNNYTQARIWGEKYFGKNF
NRLVKVKTKADPNNFFRNEQSIPPLPPRHH SEQ ID NO: 10 Illustrative RevS polypeptide sequence GenBank BAK64635.1
MELALPAELAPTLPEALRLRSEQQPDTVAYVFLRDGETPEETLTYGRLDRAARARAA
ALEAAGLAGGTAVLLYPSGLEFVAALLGCMYAGTAGAPVQVPTRRRGMERARRIA
DDAGAKTILTTTAVKREVEEHFADLLTGLTVIDTESLPDVPDDAPAVRLPGPDDVAL
LQYTSGSTGDPKGVEVTHANFRANVAETVELWPVRSDGTVVNWLPLFHDMGLMFG
VVMPLFTGVPAYLMAPQSFIRRPARWLEAISRFRGTHAAAPSFAYELCVRSVADTGL
PAGLDLSSWRVAVNGAEPVRWTAVADFTEAYAPAGFRPQAMCPGYGLAENTLKLS
GSPEDRPPTLLRADAAALQDGRVVPLTGPGTDGVRLVGSGVTVPSSRVAVVDPGTG
TEQPAGRVGEIWINGPCVARGYHGRPAESAESFGARIAGQEARGTWLRTGDLGFLH
DGEVFVAGRLKDVVIHQGRNFYPQDIELSAEVSDRALHPNCAAAFALDDGRTERLV
LLVEADGRALRNGGADALRARVHDAVWDRQRLRIDEIVLLRRGALPKTSSGKVQRR
LARSRYLDGEFGPAPAREA SEQ ID NO: 11 Illustrative *Cannabis sativa* CsAAE3 polypeptide sequence; GenBank AFD33347.1
MEKSGYGRDGIYRSLRPPLHLPNNNNLSMVSFLFRNSSSYPQKPALIDSETNQILSFSH
FKSTVIKVSHGFLNLGIKKNDVVLIYAPNSIHFPVCFLGIIASGAIATTSNPLYTVSELS
KQVKDSNPKLIITVPQLLEKVKGFNLPTILIGPDSEQESSSDKVMTFNDLVNLGGSSGS
EFPIVDDFKQSDTAALLYSSGTTGMSKGVVLTHKNFIASSLMVTMEQDLVGEMDNV
FLCFLPMFHVFGLAIITYAQLQRGNTVISMARFDLEKMLKDVEKYKVTHLWVVPPVI
LALSKNSMVKKFNLSSIKYIGSGAAPLGKDLMEECSKVVPYGIVAQGYGMTETCGIV
SMEDIRGGKRNSGSAGMLASGVEAQIVSVDTLKPLPPNQLGEIWVKGPNMMQGYFN
NPQATKLTIDKKGWVHTGDLGYFDEDGHLYVVDRIKELIKYKGFQVAPAELEGLLV
SHPEILDAVVIPFPDAEAGEVPVAYVVRSPNSSLTENDVKKFIAGQVASFKRLRKVTFI
NSVPKSASGKILRRELIQKVRSNM SEQ ID NO: 12 Illustrative *Cannabis sativa* CSAAE1 polypeptide sequence; GenBank AFD33345.1 A transmembrane domain is underlined
MGKNYKSLDSVVASDFIALGITSEVAETLHGRLAEIVCNYGAATPQTWINIANHILSP
DLPFSLHQMLFYGCYKDFGPAPPAWIPDPEKVKSTNLGALLEKRGKEFLGVKYKDPI
SSFSHFQEFSVRNPEVYWRTVLMDEMKISFSKDPECILRRDDINNPGGSEWLPGGYLN
SAKNCLNVNSNKKLNDTMIVWRDEGNDDLPLNKLTLDQLRKRVWLVGYALEEMG
LEKGCAIAIDMPMHVDAVVIYLAIVLAGYVVVSIADSFSAPEISTRLRLSKAKAIFTQD
HIIRGKKRIPLYSRVVEAKSPMAIVIPCSGSNIGAELRDGDISWDYFLERAKEFKNCEF
TAREQPVDAYTNILFSSGTTGEPKAIPWTQATPLKAAADGWSHLDIRKGDVIVWPTN -continued

| ILLUSTRATIVE SEQUENCES |
|---|
| LGWMMGPWLVYASLLNGASIALYNGSPLVSGFAKFVQDAKVTMLGVVPSIVRSWK<br>STNCVSGYDWSTIRCFSSSGEASNVDEYLWLMGRANYKPVIEMCGGTEIGGAFSAGS<br>FLQAQSLSSFSSQCMGCTLYILDKNGYPMPKNKPGIGELALGPVMFGASKTLLNGNH<br>HDVYFKGMPTLNGEVLRRHGDIFELTSNGYYHAHGRADDTMNIGGIKISSIEIERVCN<br>EVDDRVFETTAIGVPPLGGGPEQLVIFFVLKDSNDTTIDLNQLRLSFNLGLQKKLNPLF<br>KVTRVVPLSSLPRTATNKIMRRVLRQQFSHFE |
| SEQ ID NO: 13 Illustrative olivetolic acid synthase polypeptide sequence;<br>UniProtKB/Swiss-Prot: B1Q2B6.1<br>MNHLRAEGPASVLAIGTANPENILLQDEFPDYYFRVTKSEHMTQLKEKFRKICDKSM<br>IRKRNCFLNEEHLKQNPRLVEHEMQTLDARQDMLVVEVPKLGKDACAKAIKEWGQ<br>PKSKITHLIFTSASTTDMPGADYHCAKLLGLSPSVKRVMMYQLGCYGGGTVLRIAKD<br>IAENNKGARVLAVCCDIMACLFRGPSESDLELLVGQAIFGDGAAAVIVGAEPDESVG<br>ERPIFELVSTGQTILPNSEGTIGGHIREAGLIFDLHKDVPMLISNNIEKCLIEAFTPIGISD<br>WNSIFWITHPGGKAILDKVEEKLHLKSDKFVDSRHVLSEHGNMSSSTVLFVMDELRK<br>RSLEEGKSTTGDGFEWGVLFGFGPGLTVERVVVRSVPIKY |
| SEQ ID NO: 14 Illustrative olivetolic acid cyclase polypeptide sequence;<br>UniProtKB/Swiss-Prot: I6WU39.1<br>MAVKHLIVLKFKDEITEAQKEEFFKTYVNLVNIIPAMKDVYWGKDVTQKNKEEGYT<br>HIVEVTFESVETIQDYIIHPAHVGFGDVYRSFWEKLLIFDYTPRK |
| SEQ ID NO: 15 olivetolic acid cyclase polypeptide sequence lacking the N-terminal<br>methionine and C-terminal lysine relative to SEQ ID NO: 14<br>AVKHLIVLKFKDEITEAQKEEFFKTYVNLVNIIPAMKDVYWGKDVTQKNKEEGYTHI<br>VEVTFESVETIQDYIIHPAHVGFGDVYRSFWEKLLIFDYTPR |
| SEQ ID NO: 16 Truncated version of cyclase, 95 aa, lacking the N-terminal methionine<br>and five amino acid sequence YTPRK at the C-terminal end relative to SEQ ID NO: 5<br>AVKHLIVLKFKDEITEAQKEEFFKTYVNLVNIIPAMKDVYWGKDVTQKNKEEGYTHI<br>VEVTFESVETIQDYIIHPAHVGFGDVYRSFWEKLLIFD |
| SEQ ID NO: 17 protein sequence translation from hops CBDAS homolog nucleotide<br>sequence HL.Tea.v1.0.G019551<br>MNFRFSSPSLPKPSVIITPFHVSQIKATLMCSKKHGLQIRTRSGGHDSDGLSYISDVPY<br>VVIDLRNLSKVKVDVHDKTAWVQAGATIGEVYYNIAKKSPILGFPAGICYTVGVGG<br>HFSGGGYGILMRKYGLGGDNVIDVRILLANGKIVDRKSMGGDLFWALRGGGAVSFG<br>IVLAWKINLVDIPSTITIANVQMDYEQDSTKRLVHQWQTIADKFDKDLLLFVRLQTG<br>NSTTPGITKPSLQASFAVVFLGGTDKLIPLVKKSFPDLGLARKDCVEMSWIQSILLFNG<br>FPTNSSLDVLLNRTQSVMFSFKAKADYVKEPIPDDVVDKLAKSLYQEDLGTAVLQLF<br>PYGGRMGEIPESETPFPHRSGNLYELTYLARWVEKGNASETENHLKWTRSSYSYMA<br>PYVSKNPREAYLNYRDLDIGRNNYNGSTTYAQASIWGSKYYKDNFKRLVYVKTMV<br>DPSNFFRNEQSIPAYSL |
| SEQ ID NO: 18 protein sequence translation from nucleotide sequence<br>HL.Tea.v1.0.G019636.1 CBDAS homolog in hops<br>MKLRDSSIFPSVIVFMIIISLSSTTKAYATLHDYQYTKTNFIQCLSHHSSSNSSHNNDIT<br>KVVYSTTNSSYFSVLNFTIINPRFSSPSTPKPLFIITPLHESHVQAAVVCSRKHGVQIRIR<br>SGGHDYEGLSYVSDVPFVVIDLINHRSITIDVEKRTAWVQAGATLGELYYEINVKSKT<br>LAFPAGACPTIGVGGHISGGGYGSIFRKYGLAADNVIDAQIVDVEGRVLDRETMGED<br>LFWAIRGGGGASFGVILAWKVRLVPVPETVTVFAINRNLEHNVTKLVHRWQYIADK<br>LHKDLLLAVRFQTVKVNSTQEGSYKKELQATFISVFLGRVDGLLDLMGKRFPELGLA<br>REDCTEMSWIESALFVAGLPREQSPEILLDRTPQSRLSFKAKSDYVKEPIPEKGLEGIW<br>ERLYEEEIGRGVVIMSPYGGKMSEISESELPFGHRAGNLYKIQYLIYWEEEGNATVME<br>KHISWIRRLYYYMTQFVSKNPRSAYINYRDLDIGTNSNNGTASYAQASIWGVKYFGH<br>NNFNRLVHVKTIVDPTNFFRNEQSIPPLRIEYSS |
| SEQ ID NO: 19 protein sequence translation from nucleotide sequence<br>HL.Tea.v1.0.G037793.1 CBDAS homolog in hops<br>MKHSVFSYWFLCKIVNISLLSFSIRSTRADPHADFLQCFSQYISNSTTIAKLIYTPNDPL<br>YISILNSTIQNNRFSSPSTPKPLIIITPLNSFHVQASILCSRKYGLQIRTRSGGHDFEGVSY<br>VSEVPFVIVDMRNLRSITIDVDNKTAWVDVGATLGELYYRIAEKNENLSFPAGYCHT<br>VGVGGHFSGGGYGALMRKYGLAADNVIDAHLVNVDGEVLDRQSMGEDLFWAIRG<br>GGGASFGIILAWKIRLVPVPSKVTIVSINKNLEINETVKLYNKWQNIAHKFDKDLLIFV<br>RFTTMNSTDGQGKNKTAILTSFYSIFFGGMDGLLALMEKSFPELDVKRKDCFEASWI<br>EMIFYFNGFSSGDKLEVLLGRTNEEKGFFKAKLDYVRKPIPETVIVKLLEKLYNEDVG<br>LGLIQMYPYGGKMDEIPESAIPFPHRVGFIYKILYLSQWEKEEEGERHLNWVRSVYN<br>YMTPFVSKSPRASYLNYRDFDLGTNNKNGPTSYGQASIWGKKYFDKNFKRLVHVKT<br>KVDPTNFFRNEQSIPPLSVRGL |
| SEQ ID NO: 20 *Roseburia hominis* UniProtKB-G@SYC0 protein sequence<br>MDFREEYKQKLVSADEAVKLIKSGDWVDYGWCTNTVDALDQALAKRTDELTDVK<br>LRGGILMKPLAVFAREDAGEHFCWNSWHMSGIERKMINRGVAYYCPIRYSELPRYY<br>RELDCPDDVAMFQVAPMDAHGYFNFGPSASHLGAMCERAKHIIVEVNENMPRCLG<br>GTECGIHISDVTYIVEGSNPPIGELGAGGPATDVDKAVAKLIVDEIPNGACLQLGIGG<br>MPNAVGSLIAESDLKDLGVHTEMYVDAFVDIAKAGKINGSKKNIDRYRQTYAFGAG<br>TKKMYDYLDDNPELMSAPVDYTNDIRSISALDNFISINNAVDIDLYGQVNAESAGIKQ |

-continued

ILLUSTRATIVE SEQUENCES

ISGAGGQLDFVLGAYLSKGGKSFICLSSTFKTKDGQVQSRIRPTLANGSIVTDARPNT
HYVVTEYGKVNLKGLSTWQRAEALISIAHPDFRDDLIKEAEQMHIWRRSNR

SEQ ID NO: 21 *E. coli* acetyl-CoA: acetoacetyl-CoA transferase AtoA
MDAKQRIARRVAQELRDGDIVNLGIGLPTMVANYLPEGIHITLQSENGFLGLGPVTT
AHPDLVNAGGQPCGVLPGAAMFDSAMSFALIRGGHIDACVLGGLQVDEEANLANW
VVPGKMVPGMGGAMDLVTGSRKVIIAMEHCAKDGSAKILRRCTMPLTAQHAVHML
VTELAVFRFIDGKMWLTEIADGCDLATVRAKTEARFEVAADLNTQRGDL SEQ ID NO: 22 *E. coli* acetyl-CoA: acetoacetyl-CoA transferase AtoA
MKTKLMTLQDATGFFRDGMTIMVGGFMGIGTPSRLVEALLESGVRDLTLIANDTAF
VDTGIGPLIVNGRVRKVIASHIGTNPETGRRMISGEMDVVLVPQGTLIEQIRCGGAGL
GGFLTPTGVGTVVEEGKQTLTLDGKTWLLERPLRADLALIRAHRCDTLGNLTYQLSA
RNFNPLIAL SEQ ID NO: 23 *C. necator* H16 propionate CoA-transferase
MKVITAREAAALVQDGWTVASAGFVGAGHAEAVTEALEQRFLQSGLPRDLTLVYS
AGQGDRGARGVNHFGNAGMTASIVGGHWRSATRLATLAMAEQCEGYNLPQGVLT
HLYRAIAGGKPGVMTKIGLHTFVDPRTAQDARYHGGAVNERARQAIAEGKACWVD
AVDFRGDEYLFYPSFPIHCALIRCTAADARGNLSTHREAFHHELLAMAQAAHNSGGI
VIAQVESLVDHHEILQAIHVPGILVDYVVVCDNPANHQMTFAESYNPAYVTPWQGE
AAVAEAEAAPVAAGPLDARTIVQRRAVMELARRAPRVVNLGVGMPAAVGMLAHQ
AGLDGFTLTVEAGPIGGTPADGLSFGASAYPEAVVDQPAQFDFYEGGGIDLAILGLAE
LDGHGNVNVSKFGEGEGASIAGVGGFINITQSARAVVFMGTLTAGGLEVRAGDGGL
QIVREGRVKKIVPEVSHLSFNGPYVASLGIPVLYITERAVFEMRAGADGEARLTLVEI
APGVDLQRDVLDQCSTPIAVAQDLREMDARLFQAGPLHL SEQ ID NO: 24 *M. avium* mig medium chain acyl-CoA ligase
MSDTTTAFTVPAVAKAVAAAIPDRELIIQGDRRYSYRQVIERSNRLAAYLHSQGLGC
HTEREALAGHEVGQDLLGLYAYNGNEFVEALLGAFAARVAPFNVNFRYVKSELHYL
LADSEATALIYHAAFAPRVAEILPDLPRLRVLIQIADESGNELLDGAVDYEDALASVS
AEPPPVRHCPDDLYVLYTGGTTGMPKGVLWRQHDIFMTSFGGRNLMTGEPSSSIDEI
VQRAASGPGTKLMILPPLIHGAAQWSVMTAITTGQTVVFPTVVDHLDAEDVVRTIER
EKVMVVTVVGDAMARPLVAAIEKGIADVSSLAVVANGGALLTPFVKQRLIEVLPNA
VVVDGVGSSETGAQMHHMSTPGAVATGTFNAGPDTFVAAEDLSAILPPGHEGMGW
LAQRGYVPLGYKGDAAKTAKTFPVIDGVRYAVPGDRARHHADGHIELLGRDSVCIN
SGGEKIFVEEVETAIASHPAVADVVVAGRPSERWGQEVVAVVALSDGAAVDAGELI
AHASNSLARYKLPKAIVFRPVIERSPSGKADYRWAREQAVDG SEQ ID NO: 25 *A. thaliana* AT4g05160 coumarate acyl-CoA ligase
MEKSGYGRDGIYRSLRPTLVLPKDPNTSLVSFLFRNSSSYPSKLAIADSDTGDSLTFSQ
LKSAVARLAHGFHRLGIRKNDVVLIFAPNSYQFPLCFLAVTAIGGVFTTANPLYTVNE
VSKQIKDSNPKIIISVNQLFDKIKGFDLPVVLLGSKDTVEIPPGSNSKILSFDNVMELSE
PVSEYPFVEIKQSDTAALLYSSGTTGTSKGVELTHGNFIAASLMVTMDQDLMGEYHG
VFLCFLPMFHVFGLAVITYSQLQRGNALVSMARFELELVLKNIEKFRVTHLWVVPPV
FLALSKQSIVKKFDLSSLKYIGSGAAPLGKDLMEECGRNIPNVLLMQGYGMTETCGI
VSVEDPRLGKRNSGSAGMLAPGVEAQIVSVETGKSQPPNQQGEIWVRGPNMMKGY
LNNPQATKETIDKKSWVHTGDLGYFNEDGNLYVVDRIKELIKYKGFQVAPAELEGL
LVSHPDILDAVVIPFPDEEAGEVPIAFVVRSPNSSITEQDIQKFIAKQVAPYKRLRRVSF
ISLVPKSAAGKILRRELVQQVRSKM SEQ ID NO: 26 *S. cerevisiae* FAA2 medium chain acyl-CoA ligase
MAAPDYALTDLIESDPRFESLKTRLAGYTKGSDEYIEELYSQLPLTSYPRYKTFLKKQ
AVAISNPDNEAGFSSIYRSSLSSENLVSCVDKNLRTAYDHFMFSARRWPQRDCLGSRP
IDKATGTWEETFRFESYSTVSKRCHNIGSGILSLVNTKRKRPLEANDFVVAILSHNNPE
WILTDLACQAYSLTNTALYETLGPNTSEYILNLTEAPILIFAKSNMYHVLKMVPDMK
FVNTLVCMDELTHDELRMLNESLLPVKCNSLNEKITFFSLEQVEQVGCFNKIPAIPPTP
DSLYTISFTSGTTGLPKGVEMSHRNIASGIAFAFSTFRIPPDKRNQQLYDMCFLPLAHIF
ERMVIAYDLAIGFGIGFLHKPDPTVLVEDLKILKPYAVALVPRILTRFEAGIKNALDKS
TVQRNVANTILDSKSARFTARGGPDKSIMNFLVYHRVLIDKIRDSLGLSNNSFIITGSA
PISKDTLLFLRSALDIGIRQGYGLTETFAGVCLSEPFEKDVGSCGAIGISAECRLKSVPE
MGYHADKDLKGELQIRGPQVFERYFKNPNETSKAVDQDGWFSTGDVAFIDGKGRIS
VIDRVKNFFKLAHGEYIAPEKIENIYLSSCPYITQIFVFGDPLKTFLVGIVGVDVDAAQ
PILAAKHPEVKTWTKEVLVENLNRNKKLRKEFLNKINKCTDGLQGFEKLHNIKVGLE
PLTLEDDVVTPTFKIKRAKASKFFKDTLDQLYAEGSLVKTEKL SEQ ID NO: 27 *E. coli* FADK acyl-CoA ligase
MHPTGPHLGPDVLFRESNMKVTLTFNEQRRAAYRQQGLWGDASLADYWQQTARA
MPDKIAVVDNHGASYTYSALDHAASCLANWMLAKGIESGDRIAFQLPGWCEFTVIY
LACLKIGAVSVPLLPSWREAELVWVLNKCQAKMFFAPTLFKQTRPVDLILPLQNQLP
QLQQIVGVDKLAPATSSLSLSQIIADNTSLTTAITTHGDELAAVLFTSGTEGLPKGVML
THNNILASERAYCARLNLTWQDVFMMPAPLGHATGFLHGVTAPFLIGARSVLLDIFT -continued

| ILLUSTRATIVE SEQUENCES |
|---|
| PDACLALLEQQRCTCMLGATPFVYDLLNVLEKQPADLSALRFFLCGGTTIPKKVARE<br>CQQRGIKLLSVYGSTESSPHAVVNLDDPLSRFMHTDGYAAAGVEIKVVDDARKTLPP<br>GCEGEEASRGPNVFMGYFDEPELTARALDEEGWYYSGDLCRMDEAGYIKITGRKKD<br>IIVRGGENISSREVEDILLQHPKIHDACVVAMSDERLGERSCAYVVLKAPHHSLSLEE<br>VVAFFSRKRVAKYKYPEHIVVIEKLPRTTSGKIQKFLLRKDIMRRLTQDVCEEIE |

What is claimed is:

1. A modified recombinant yeast host cell comprising a first exogenous polynucleotide that encodes a prenyltransferase and a second exogenous polynucleotide that encodes a cannabichromenic acid (CBCA) synthase, a cannabidiolic acid (CBDA) synthase, or a tetrahydrocannabinolic acid (THCA) synthase, wherein the prenyltransferase comprises a geranyl-pyrophosphate-olivetolic acid geranyltransferase (GOT), and wherein the GOT is expressed as a fusion protein with a partner that confers enhanced expression of the active GOT.

2. The modified recombinant yeast host cell of claim 1, wherein the prenyltransferase amino acid sequence comprises SEQ ID NO:2.

3. The modified recombinant yeast host cell of claim 1, wherein the second exogenous polynucleotide encodes a CBCA synthase and the CBCA synthase comprises an amino acid sequence having at least 95% identity to any one of SEQ ID NOS:3-9.

4. The modified recombinant yeast host cell of claim 1, wherein the prenyltransferase amino acid sequence comprises SEQ ID NO:2; and the second exogenous polynucleotide encodes a CBDA synthase or THCA synthase.

5. The modified recombinant yeast host cell of claim 1, wherein the yeast cell is genetically modified to overexpress mevalonate pathway enzymes.

6. The modified recombinant yeast host cell of claim 5, wherein one or more mevalonate pathway enzymes is an endogenous enzyme.

7. The modified recombinant yeast host cell of claim 5, wherein one or more mevalonate pathway enzymes is an exogenous enzyme not natively expressed in the yeast host cell.

8. The modified recombinant yeast host cell of claim 1, wherein the yeast host cell is modified to overexpress erg10, erg13, thmgr, erg12, erg8, mvd1, idi1, and erg20 F96WN127W, and the mvaE, mvaS genes from *Enterococcus faecalis*.

9. A method of producing a cannabinoid, the method comprising:

providing olivetolic acid or divarinic acid, or a fluorinated or chlorinated analog thereof to a modified recombinant yeast host cell according to claim 1 to produce the corresponding acidic cannabinoid CBCA, CBDA, or THCA, or fluorinated or chlorinated analog thereof, said acidic cannabinoid generated by prenylation of olivetolic acid or divarinic acid, or analog thereof;

decarboxylating the acidic cannabinoid enzymatically or chemically to produce the corresponding compound CBC, CBD, or THC, or analog thereof.

10. The method of claim 9, wherein the recombinant yeast host cell expresses a polynucleotide that encodes a CBCA synthase.

11. The method of claim 10, wherein CBCA produced is of greater than 96% enantiomeric purity.

12. The method of claim 9, wherein the decarboxylation step is performed on an extract of the yeast host cell prepared using an extraction reagent comprising an organic solvent or organic solvent/water mixture.

13. The method of claim 9, wherein the decarboxylation step comprises incubating the extract at a temperature of 20° to 100° C. in the presence of a metal catalyst.

14. The method of claim 13, wherein the metal catalyst is zinc, molybdenum, nickel, copper, platinum, palladium, or iron.

15. The method of claim 13, wherein the metal catalyst is provided as a metal-loaded zeolite catalyst.

16. The method of claim 9, wherein the decarboxylation step is performed with a decarboxylase enzyme.

17. The method of claim 16, wherein the decarboxylase is an *Aspergillus nidulans* orsB decarboxylase, a PatG enzyme from *Aspergillus clavatus*, or a 3,4-dihydroxybenzoic acid decarboxylase from *Enterobacter cloacae*.

18. The method of claim 9, wherein, the olivetolic acid or divarinic acid, or analog thereof, is produced by the host cell, which is genetically modified to express a polynucleotide that encodes an acyl-CoA synthase selected from the group consisting of *Roseburia hominis* butanoylCoA transferase, revS, CsAAE3, and CsAAE1; to express a polynucleotide that encodes olivetolic acid synthase; and to express a polynucleotide that encodes olivetolic acid cyclase.

19. The method of claim 18, wherein the acyl-CoA synthase is *Roseburia hominis* butanoylCoA transferase.

20. The method of claim 18, wherein the acyl-CoA synthase comprises an amino acid sequence having at least 95% identity to SEQ ID NO:20; the olivetolic acid synthase comprises an amino acid sequence having at least 95% amino acid sequence identity to SEQ ID NO:13; and the olivetolic acid cyclase comprises an amino acid sequence having at least 95% identity to SEQ ID NO:14, SEQ ID NO:15, or SEQ ID NO:16.

21. A modified recombinant yeast host cell comprising an exogenous polynucleotide that encodes a prenyltransferase, wherein the amino acid sequence of the prenyltransferase is SEQ ID NO:1; or comprising an exogenous polynucleotide that encodes a prenyltransferase polypeptide, wherein the prenyltransferase polypeptide comprises the amino acid sequence of SEQ ID NO:2.

22. The modified recombinant yeast host cell of claim 21, further comprising a second exogenous polynucleotide that encodes a cannabichromenic acid (CBCA) synthase, a cannabidiolic acid (CBDA) synthase, or a tetrahydrocannabinolic acid (THCA) synthase.

23. The modified recombinant yeast host cell of claim 1, wherein the partner that confers enhanced expression of the active GOT is selected from the group consisting of a superoxide dismutase, a yeast maltose binding protein (MBP), a human or yeast ubiquitin (Ub), a catalase, *Saccharomyces cerevisiae* catalase T (CTT1), or *Saccharomyces cerevisiae* peroxisomal catalase A (CTA1), transferrin, and human serum albumin (HSA).

24. The modified recombinant yeast host cell of claim 23, wherein the superoxide dismutase is human superoxide dismutase (hSOD).

25. The modified recombinant yeast host cell of claim 23, wherein the catalase is human catalase (hCAT).

26. The modified recombinant yeast host cell of claim 1, wherein the partner that confers enhanced expression of the active GOT is selected from the group consisting of human galectin, *Escherichia coli* maltose binding protein (MBP), yeast prepro alpha factor, and GB 1.

* * * * *